US012570701B2

(12) United States Patent
Tokatlian et al.

(10) Patent No.: US 12,570,701 B2
(45) Date of Patent: Mar. 10, 2026

(54) FERRITIN NANOPARTICLE DISPLAYING AN HIV TRIMER

(71) Applicants: International AIDS Vaccine Initiative, Inc., New York, NY (US); The Scripps Research Institute, La Jolla, CA (US); Massachusetts Institute of Technology, Cambridge, MA (US)

(72) Inventors: Talar Tokatlian, Cambridge, MA (US); Benjamin J. Read, Cambridge, MA (US); Daniel W. Kulp, New York, NY (US); Sergey Menis, New York, NY (US); Jon M. Steichen, New York, NY (US); William R. Schief, La Jolla, CA (US); Darrell J. Irvine, Cambridge, MA (US)

(73) Assignees: International AIDS Vaccine Initiative, Inc., New York, NY (US); The Scripps Research Institute, La Jolla, CA (US); Massachusetts Institute of Technology, Cambridge, MA (US)

( * ) Notice: Subject to any disclaimer, the term of this patent is extended or adjusted under 35 U.S.C. 154(b) by 924 days.

(21) Appl. No.: 17/255,408

(22) PCT Filed: Jun. 5, 2019

(86) PCT No.: PCT/US2019/035635
§ 371 (c)(1),
(2) Date: Dec. 22, 2020

(87) PCT Pub. No.: WO2019/236736
PCT Pub. Date: Dec. 12, 2019

(65) Prior Publication Data
US 2021/0363194 A1 Nov. 25, 2021

Related U.S. Application Data

(60) Provisional application No. 62/681,051, filed on Jun. 5, 2018.

(51) Int. Cl.
| | |
|---|---|
| *C07K 14/16* | (2006.01) |
| *A61K 39/12* | (2006.01) |
| *C12N 7/00* | (2006.01) |
| *A61K 38/00* | (2006.01) |
| *A61K 39/00* | (2006.01) |

(52) U.S. Cl.
CPC ............ *C07K 14/162* (2013.01); *A61K 39/12* (2013.01); *C12N 7/00* (2013.01); *A61K 38/00* (2013.01); *A61K 2039/55555* (2013.01); *A61K 2039/6031* (2013.01); *C12N 2740/16022* (2013.01); *C12N 2740/16034* (2013.01); *C12N 2740/16134* (2013.01)

(58) Field of Classification Search
CPC ...... C07K 14/162; A61K 39/12; A61K 38/00; A61K 2039/55555; A61K 2039/6031; A61K 2039/5555; C12N 7/00; C12N 2740/16022; C12N 2740/16034; C12N 2740/16134
See application file for complete search history.

(56) References Cited

U.S. PATENT DOCUMENTS

| | | | |
|---|---|---|---|
| 7,939,083 B2 | 5/2011 | Dey et al. | |
| 2006/0251679 A1 | 11/2006 | Carter et al. | |
| 2011/0076298 A1 | 3/2011 | Olson et al. | |
| 2017/0233441 A1 | 8/2017 | Kwong et al. | |

FOREIGN PATENT DOCUMENTS

WO 2017/165674 A1 9/2017

OTHER PUBLICATIONS

Anna-Janinabehrens, CompositionandAntigenicEffectsofIndividual GlycanSitesofaTrimericHIV-1Envelope Glycoprotein, Cell Rep. Mar. 22, 2016; 14(11): 2695-2706.*
Rogier, W. Sanders, et al., A Next-Generation Cleaved, Soluble HIV-1 Env Trimer, BG505 SOSIP.664 gp140, Expresses Multiple Epitopes for Broadly Neutralizing but Not Non-Neutralizing Antibodies, PLOS Pathogens, (Sep. 2013) vol. 9, Issue 9, e1003618, pp. 1-20.
International Search Report and Written Opinion dated Oct. 2, 2019 issued in PCT/US2019/035635.
IRPR dated Dec. 8, 2020 issued in PCT/US2019/035635.

* cited by examiner

*Primary Examiner* — Julie Ha
*Assistant Examiner* — Erinne R Dabkowski
(74) *Attorney, Agent, or Firm* — Duane Morris LLP; Thomas J. Kowalski

(57) ABSTRACT
The present invention relates to glycosylate HIV timer nanoparticles fused to self-assembling ferritin proteins which may be utilized as immunogens to enhance trafficking to lymph nodes and germinal centers and to heighten immune responses.

22 Claims, 26 Drawing Sheets
Specification includes a Sequence Listing.

A

EDC coupling
MES buffer, pH 6

Latex Beads
(40, 100, 200 nm)

4-aminophenyl
1,3-α-1,6-α-D-
mannotrioside

SEQUENCE LISTING

<160> NUMBER OF SEQ ID NOS: 10

<210> SEQ ID NO 1
<211> LENGTH: 811
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
            100                 105                 110

Arg Gly Glu Leu Lys Asn Cys Ser Phe Asn Met Thr Thr Glu Leu Arg
        115                 120                 125

Asp Lys Lys Gln Lys Val Tyr Ser Leu Phe Tyr Arg Leu Asp Val Val
    130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
        195                 200                 205
```

-continued

```
Cys Pro Ser Val Ser Thr Val Gln Cys Thr His Gly Ile Lys Pro Val
    210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
                260                 265                 270

Thr Val Lys Ser Ile Arg Ile Gly Pro Gly Gln Ala Phe Tyr Tyr Thr
            275                 280                 285

Gly Asp Ile Ile Gly Asp Ile Arg Gln Ala His Cys Asn Val Ser Lys
    290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
            355                 360                 365

Ser Val Gln Gly Ser Asn Ser Thr Gly Ser Asn Asp Ser Ile Thr Leu
    370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
            435                 440                 445

Ser Glu Leu Tyr Lys Tyr Lys Val Val Lys Ile Glu Pro Leu Gly Val
    450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
                500                 505                 510

Asn Leu Leu Ser Gly Ile Val Gln Gln Gln Ser Asn Leu Leu Arg Ala
            515                 520                 525

Pro Glu Pro Gln Gln His Leu Leu Lys Asp Thr His Trp Gly Ile Lys
    530                 535                 540

Gln Leu Gln Ala Arg Val Leu Ala Val Glu His Tyr Leu Arg Asp Gln
545                 550                 555                 560

Gln Leu Leu Gly Ile Trp Gly Cys Ser Gly Lys Leu Ile Cys Cys Thr
                565                 570                 575

Asn Val Pro Trp Asn Ser Ser Trp Ser Asn Arg Asn Leu Ser Glu Ile
                580                 585                 590

Trp Asp Asn Met Thr Trp Leu Gln Trp Asp Lys Glu Ile Ser Asn Tyr
            595                 600                 605

Thr Gln Ile Ile Tyr Gly Leu Leu Glu Glu Ser Gln Asn Gln Gln Glu
    610                 615                 620

Lys Asn Glu Gln Asp Leu Leu Ala Leu Asp Gly Ser Gly Gly Leu Ser
```

-continued

```
625                   630                   635                   640

Glu Arg Met Leu Lys Ala Leu Asn Asp Gln Leu Asn Arg Glu Leu Tyr
                  645                   650                   655

Ser Ala Tyr Leu Tyr Phe Ala Met Ala Ala Tyr Phe Glu Asp Leu Gly
                  660                   665                   670

Leu Glu Gly Phe Ala Asn Trp Met Lys Ala Gln Ala Glu Glu Glu Ile
              675                   680                   685

Gly His Ala Leu Arg Phe Tyr Asn Tyr Ile Tyr Asp Lys Asn Gly Arg
          690                   695                   700

Val Glu Leu Asp Glu Ile Pro Lys Pro Lys Glu Trp Glu Ser Pro
705                   710                   715                   720

Leu Lys Ala Phe Glu Ala Ala Tyr Glu His Glu Lys Phe Ile Ser Lys
                  725                   730                   735

Ser Ile Tyr Glu Leu Ala Ala Leu Ala Glu Glu Glu Lys Asp Tyr Ser
                  740                   745                   750

Thr Arg Ala Phe Leu Glu Trp Phe Ile Asn Glu Gln Val Glu Glu Glu
                  755                   760                   765

Ala Ser Val Lys Lys Ile Leu Asp Lys Leu Lys Phe Ala Lys Asp Ser
          770                   775                   780

Pro Gln Ile Leu Phe Met Leu Asp Lys Glu Leu Ser Ala Arg Ala Pro
785                   790                   795                   800

Lys Leu Pro Gly Leu Leu Met Gln Gly Gly Glu
                  805                   810

<210> SEQ ID NO 2
<211> LENGTH: 811
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Ala Glu Asn Leu Trp Val Thr Val Tyr Tyr Gly Val Pro Val Trp Lys
1                   5                   10                   15

Asp Ala Glu Thr Thr Leu Phe Cys Ala Ser Asp Ala Lys Ala Tyr Glu
                  20                   25                   30

Thr Glu Lys His Asn Val Trp Ala Thr His Ala Cys Val Pro Thr Asp
          35                   40                   45

Pro Asn Ser Ser Glu Ile His Leu Glu Asn Val Thr Glu Glu Phe Asn
      50                   55                   60

Met Trp Lys Asn Asn Met Val Glu Gln Met His Glu Asp Ile Ile Ser
65                   70                   75                   80

Leu Trp Asp Gln Ser Leu Lys Pro Cys Val Lys Leu Thr Pro Leu Cys
                  85                   90                   95

Val Thr Leu Gln Cys Thr Asn Val Thr Asn Asn Ile Thr Asp Asp Met
                  100                   105                   110

Arg Gly Glu Leu Lys Asn Cys Ser Phe Asn Met Thr Thr Glu Leu Arg
              115                   120                   125

Asp Lys Lys Gln Lys Val Tyr Ser Leu Phe Tyr Arg Leu Asp Val Val
          130                   135                   140

Gln Ile Asn Glu Asn Gln Gly Asn Arg Ser Asn Asn Ser Asn Lys Glu
145                   150                   155                   160

Tyr Arg Leu Ile Asn Cys Asn Thr Ser Ala Ile Thr Gln Ala Cys Pro
                  165                   170                   175
```

-continued

```
Lys Val Ser Phe Glu Pro Ile Pro Ile His Tyr Cys Ala Pro Ala Gly
            180             185             190

Phe Ala Ile Leu Lys Cys Lys Asp Lys Lys Phe Asn Gly Thr Gly Pro
            195             200             205

Cys Gln Asn Val Ser Thr Val Gln Cys Thr His Gly Ile Lys Pro Val
        210             215             220

Val Ser Thr Gln Leu Leu Leu Asn Gly Ser Leu Ala Glu Glu Glu Val
225             230             235             240

Ile Ile Arg Ser Glu Asn Ile Thr Asn Asn Ala Lys Asn Ile Leu Val
                245             250             255

Gln Leu Asn Thr Ser Val Gln Ile Asn Cys Thr Arg Pro Asn Asn Asn
            260             265             270

Thr Val Lys Ser Ile Arg Ile Gly Pro Gly Gln Ala Phe Tyr Tyr Thr
            275             280             285

Gly Asp Ile Ile Gly Asp Ile Arg Gln Ala His Cys Asn Val Ser Lys
        290             295             300

Ala Thr Trp Asn Glu Thr Leu Gly Lys Val Val Lys Gln Leu Arg Lys
305             310             315             320

His Phe Gly Asn Asn Thr Ile Ile Arg Phe Ala Gln Ser Ser Gly Gly
                325             330             335

Asp Leu Glu Val Thr Thr His Ser Phe Asn Cys Gly Gly Glu Phe Phe
            340             345             350

Tyr Cys Asn Thr Ser Gly Leu Phe Asn Ser Thr Trp Ile Ser Asn Thr
            355             360             365

Ser Val Gln Gly Ser Asn Ser Thr Gly Ser Asn Asp Ser Ile Thr Leu
            370             375             380

Pro Cys Arg Ile Lys Gln Ile Ile Asn Met Trp Gln Arg Ile Gly Gln
385             390             395             400

Ala Met Tyr Ala Pro Pro Ile Gln Gly Val Ile Arg Cys Val Ser Asn
                405             410             415

Ile Thr Gly Leu Ile Leu Thr Arg Asp Gly Gly Ser Thr Asn Ser Thr
            420             425             430

Thr Glu Thr Phe Arg Pro Gly Gly Gly Asp Met Arg Asp Asn Trp Arg
            435             440             445

Ser Glu Leu Tyr Lys Tyr Lys Val Val Lys Ile Glu Pro Leu Gly Val
        450             455             460

Ala Pro Thr Arg Cys Lys Arg Arg Val Val Gly Arg Arg Arg Arg Arg
465             470             475             480

Arg Ala Val Gly Ile Gly Ala Val Ser Leu Gly Phe Leu Gly Ala Ala
                485             490             495

Gly Ser Thr Met Gly Ala Ala Ser Met Thr Leu Thr Val Gln Ala Arg
            500             505             510

Asn Leu Leu Ser Gly Ile Val Gln Gln Ser Asn Leu Leu Arg Ala
            515             520             525

Pro Glu Pro Gln Gln His Leu Leu Lys Asp Thr His Trp Gly Ile Lys
            530             535             540

Gln Leu Gln Ala Arg Val Leu Ala Val Glu His Tyr Leu Arg Asp Gln
545             550             555             560

Gln Leu Leu Gly Ile Trp Gly Cys Ser Gly Lys Leu Ile Cys Cys Thr
                565             570             575

Asn Val Pro Trp Asn Ser Ser Trp Ser Asn Arg Asn Leu Ser Glu Ile
            580             585             590

Trp Asp Asn Met Thr Trp Leu Gln Trp Asp Lys Glu Ile Ser Asn Tyr
```

-continued

```
                595                 600                 605
Thr Gln Ile Ile Tyr Gly Leu Leu Glu Glu Ser Gln Asn Gln Gln Glu
    610                 615                 620

Lys Asn Glu Gln Asp Leu Leu Ala Leu Asp Gly Ser Gly Gly Leu Ser
625                 630                 635                 640

Glu Arg Met Leu Lys Ala Leu Asn Asp Gln Leu Asn Arg Glu Leu Tyr
                645                 650                 655

Ser Ala Tyr Leu Tyr Phe Ala Met Ala Ala Tyr Phe Glu Asp Leu Gly
                660                 665                 670

Leu Glu Gly Phe Ala Asn Trp Met Lys Ala Gln Ala Glu Glu Glu Ile
                675                 680                 685

Gly His Ala Leu Arg Phe Tyr Asn Tyr Ile Tyr Asp Lys Asn Gly Arg
    690                 695                 700

Val Glu Leu Asp Glu Ile Pro Lys Pro Pro Lys Glu Trp Glu Ser Pro
705                 710                 715                 720

Leu Lys Ala Phe Glu Ala Ala Tyr Glu His Glu Lys Phe Ile Ser Lys
                725                 730                 735

Ser Ile Tyr Glu Leu Ala Ala Leu Ala Glu Glu Glu Lys Asp Tyr Ser
                740                 745                 750

Thr Arg Ala Phe Leu Glu Trp Phe Ile Asn Glu Gln Val Glu Glu Glu
                755                 760                 765

Ala Ser Val Lys Lys Ile Leu Asp Lys Leu Lys Phe Ala Lys Asp Ser
    770                 775                 780

Pro Gln Ile Leu Phe Met Leu Asp Lys Glu Leu Ser Ala Arg Ala Pro
785                 790                 795                 800

Lys Leu Pro Gly Leu Leu Met Gln Gly Gly Glu
                805                 810
```

```
<210> SEQ ID NO 3
<211> LENGTH: 819
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
                20                  25                  30

Thr Glu Lys His Asn Val Trp Ala Thr His Ala Cys Val Pro Thr Asp
                35                  40                  45

Pro Asn Pro Gln Glu Ile His Leu Glu Asn Val Thr Glu Glu Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
                100                 105                 110

Arg Gly Glu Leu Lys Asn Cys Ser Phe Asn Met Thr Thr Glu Leu Arg
                115                 120                 125

Asp Lys Lys Gln Lys Val Tyr Ser Leu Phe Tyr Arg Leu Asp Val Val
    130                 135                 140
```

-continued

```
Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
            195                 200                 205

Cys Pro Ser Val Ser Thr Val Gln Cys Thr His Gly Ile Lys Pro Val
        210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
                260                 265                 270

Thr Val Lys Ser Ile Arg Ile Gly Pro Gly Gln Ala Phe Tyr Tyr Thr
            275                 280                 285

Gly Asp Ile Ile Gly Asp Ile Arg Gln Ala His Cys Asn Val Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
            355                 360                 365

Ser Val Gln Gly Ser Asn Ser Thr Gly Ser Asn Asp Ser Ile Thr Leu
        370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
            435                 440                 445

Ser Glu Leu Tyr Lys Tyr Lys Val Val Lys Ile Glu Pro Leu Gly Val
        450                 455                 460

Ala Pro Thr Arg Cys Lys Arg Arg Val Val Gly Ser His Ser Gly Ser
465                 470                 475                 480

Gly Gly Ser Gly Ser Gly Gly His Ala Ala Val Gly Ile Gly Ala Val
                485                 490                 495

Ser Leu Gly Phe Leu Gly Ala Ala Gly Ser Thr Met Gly Ala Ala Ser
            500                 505                 510

Met Thr Leu Thr Val Gln Ala Arg Asn Leu Leu Ser Gly Ile Val Gln
            515                 520                 525

Gln Gln Ser Asn Leu Leu Arg Ala Pro Glu Pro Gln Gln His Leu Leu
        530                 535                 540

Lys Asp Thr His Trp Gly Ile Lys Gln Leu Gln Ala Arg Val Leu Ala
545                 550                 555                 560

Val Glu His Tyr Leu Arg Asp Gln Gln Leu Leu Gly Ile Trp Gly Cys
```

-continued

```
                        565                 570                 575
Ser Gly Lys Leu Ile Cys Cys Thr Asn Val Pro Trp Asn Ser Ser Trp
            580                 585                 590

Ser Asn Arg Asn Leu Ser Glu Ile Trp Asp Asn Met Thr Trp Leu Gln
            595                 600                 605

Trp Asp Lys Glu Ile Ser Asn Tyr Thr Gln Ile Ile Tyr Gly Leu Leu
            610                 615                 620

Glu Glu Ser Gln Asn Gln Gln Glu Lys Asn Glu Gln Asp Leu Leu Ala
625                 630                 635                 640

Leu Asp Gly Ser Gly Gly Leu Ser Glu Arg Met Leu Lys Ala Leu Asn
                645                 650                 655

Asp Gln Leu Asn Arg Glu Leu Tyr Ser Ala Tyr Leu Tyr Phe Ala Met
            660                 665                 670

Ala Ala Tyr Phe Glu Asp Leu Gly Leu Glu Gly Phe Ala Asn Trp Met
            675                 680                 685

Lys Ala Gln Ala Glu Glu Glu Ile Gly His Ala Leu Arg Phe Tyr Asn
            690                 695                 700

Tyr Ile Tyr Asp Lys Asn Gly Arg Val Glu Leu Asp Glu Ile Pro Lys
705                 710                 715                 720

Pro Pro Lys Glu Trp Glu Ser Pro Leu Lys Ala Phe Glu Ala Ala Tyr
                725                 730                 735

Glu His Glu Lys Phe Ile Ser Lys Ser Ile Tyr Glu Leu Ala Ala Leu
            740                 745                 750

Ala Glu Glu Glu Lys Asp Tyr Ser Thr Arg Ala Phe Leu Glu Trp Phe
            755                 760                 765

Ile Asn Glu Gln Val Glu Glu Glu Ala Ser Val Lys Lys Ile Leu Asp
        770                 775                 780

Lys Leu Lys Phe Ala Lys Asp Ser Pro Gln Ile Leu Phe Met Leu Asp
785                 790                 795                 800

Lys Glu Leu Ser Ala Arg Ala Pro Lys Leu Pro Gly Leu Leu Met Gln
                805                 810                 815

Gly Gly Glu
```

<210> SEQ ID NO 4
<211> LENGTH: 804
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 4

```
Ala Glu Asn Leu Trp Val Thr Val Tyr Tyr Gly Val Pro Val Trp Lys
1               5                   10                  15

Asp Ala Glu Thr Thr Leu Phe Cys Ala Ser Asp Ala Lys Ala Tyr Glu
            20                  25                  30

Thr Glu Lys His Asn Val Trp Ala Thr His Ala Cys Val Pro Thr Asp
        35                  40                  45

Pro Asn Pro Gln Glu Ile His Leu Glu Asn Val Thr Glu Glu Phe Asn
        50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu Gln Cys Thr Asn Val Thr Asn Asn Ile Thr Asp Asp Met
```

-continued

```
                  100                 105                 110

Arg Gly Glu Leu Lys Asn Cys Ser Phe Asn Met Thr Thr Glu Leu Arg
            115                 120                 125

Asp Lys Lys Gln Lys Val Tyr Ser Leu Phe Tyr Arg Leu Asp Val Val
        130                 135                 140

Gln Ile Asn Glu Asn Gln Gly Asn Arg Ser Asn Asn Ser Asn Lys Glu
145                 150                 155                 160

Tyr Arg Leu Ile Asn Cys Asn Thr Ser Ala Ile Thr Gln Ala Cys Pro
                165                 170                 175

Lys Val Ser Phe Glu Pro Ile Pro Ile His Tyr Cys Ala Pro Ala Gly
            180                 185                 190

Phe Ala Ile Leu Lys Cys Lys Asp Lys Lys Phe Asn Gly Thr Gly Pro
            195                 200                 205

Cys Pro Ser Val Ser Thr Val Gln Cys Thr His Gly Ile Lys Pro Val
        210                 215                 220

Val Ser Thr Gln Leu Leu Leu Asn Gly Ser Leu Ala Glu Glu Glu Val
225                 230                 235                 240

Ile Ile Arg Ser Glu Asn Ile Thr Asn Asn Ala Lys Asn Ile Leu Val
                245                 250                 255

Gln Leu Asn Thr Pro Val Gln Ile Asn Cys Thr Arg Pro Asn Asn Asn
            260                 265                 270

Thr Val Lys Ser Ile Arg Ile Gly Pro Gly Gln Ala Phe Tyr Tyr Thr
            275                 280                 285

Gly Asp Ile Ile Gly Asp Ile Arg Gln Ala His Cys Asn Val Ser Lys
        290                 295                 300

Ala Thr Trp Asn Glu Thr Leu Gly Lys Val Val Lys Gln Leu Arg Lys
305                 310                 315                 320

His Phe Gly Asn Asn Thr Ile Ile Arg Phe Ala Gln Ser Ser Gly Gly
                325                 330                 335

Asp Leu Glu Val Thr Thr His Ser Phe Asn Cys Gly Gly Glu Phe Phe
            340                 345                 350

Tyr Cys Asn Thr Ser Gly Leu Phe Asn Ser Thr Trp Ile Ser Asn Thr
            355                 360                 365

Ser Val Gln Gly Ser Asn Ser Thr Gly Ser Asn Asp Ser Ile Thr Leu
        370                 375                 380

Pro Cys Arg Ile Lys Gln Ile Ile Asn Met Trp Gln Arg Ile Gly Gln
385                 390                 395                 400

Ala Met Tyr Ala Pro Pro Ile Gln Gly Val Ile Arg Cys Val Ser Asn
                405                 410                 415

Ile Thr Gly Leu Ile Leu Thr Arg Asp Gly Gly Ser Thr Asn Ser Thr
            420                 425                 430

Thr Glu Thr Phe Arg Pro Gly Gly Gly Asp Met Arg Asp Asn Trp Arg
            435                 440                 445

Ser Glu Leu Tyr Lys Tyr Lys Val Val Lys Ile Glu Pro Leu Gly Val
        450                 455                 460

Ala Pro Thr Arg Cys Lys Arg Arg Val Val Gly Arg Arg Arg Arg Arg
465                 470                 475                 480

Arg Ala Val Gly Ile Gly Ala Val Ser Leu Gly Phe Leu Gly Ala Ala
                485                 490                 495

Gly Ser Thr Met Gly Ala Ala Ser Met Thr Leu Thr Val Gln Ala Arg
            500                 505                 510

Asn Leu Leu Ser Gly Ile Val Gln Gln Gln Ser Asn Leu Leu Arg Ala
            515                 520                 525
```

-continued

```
Pro Glu Pro Gln Gln His Leu Leu Lys Asp Thr His Trp Gly Ile Lys
    530             535             540

Gln Leu Gln Ala Arg Val Leu Ala Val Glu His Tyr Leu Arg Asp Gln
545             550             555             560

Gln Leu Leu Gly Ile Trp Gly Cys Ser Gly Lys Leu Ile Cys Cys Thr
                565             570             575

Asn Val Pro Trp Asn Ser Ser Trp Ser Asn Arg Asn Leu Ser Glu Ile
            580             585             590

Trp Asp Asn Met Thr Trp Leu Gln Trp Asp Lys Glu Ile Ser Asn Tyr
        595             600             605

Thr Gln Ile Ile Tyr Gly Leu Leu Glu Glu Ser Gln Asn Gln Gln Glu
    610             615             620

Lys Asn Glu Gln Asp Leu Leu Ala Leu Asp Gly Ser Gly Gly Leu Ser
625             630             635             640

Lys Asp Ile Ile Lys Leu Leu Asn Glu Gln Val Asn Lys Glu Met Gln
            645             650             655

Ser Ser Asn Leu Tyr Met Ser Met Ser Ser Trp Cys Tyr Thr His Ser
        660             665             670

Leu Asp Gly Ala Gly Leu Phe Leu Phe Asp His Ala Ala Glu Glu Tyr
        675             680             685

Glu His Ala Lys Lys Leu Ile Ile Phe Leu Asn Glu Asn Asn Val Pro
    690             695             700

Val Gln Leu Thr Ser Ile Ser Ala Pro Glu His Lys Phe Glu Gly Leu
705             710             715             720

Thr Gln Ile Phe Gln Lys Ala Tyr Glu His Glu Gln His Ile Ser Glu
            725             730             735

Ser Ile Asn Asn Ile Val Asp His Ala Ile Lys Ser Lys Asp His Ala
        740             745             750

Thr Phe Asn Phe Leu Gln Trp Tyr Val Ala Glu Gln His Glu Glu Glu
        755             760             765

Val Leu Phe Lys Asp Ile Leu Asp Lys Ile Glu Leu Ile Gly Asn Glu
    770             775             780

Asn His Gly Leu Tyr Leu Ala Asp Gln Tyr Val Lys Gly Ile Ala Lys
785             790             795             800

Ser Arg Lys Ser
```

<210> SEQ ID NO 5
<211> LENGTH: 174
<212> TYPE: PRT
<213> ORGANISM: Pyrococcus furiosus

<400> SEQUENCE: 5

```
Met Leu Ser Glu Arg Met Leu Lys Ala Leu Asn Asp Gln Leu Asn Arg
1               5               10              15

Glu Leu Tyr Ser Ala Tyr Leu Tyr Phe Ala Met Ala Ala Tyr Phe Glu
            20              25              30

Asp Leu Gly Leu Glu Gly Phe Ala Asn Trp Met Lys Ala Gln Ala Glu
        35              40              45

Glu Glu Ile Gly His Ala Leu Arg Phe Tyr Asn Tyr Ile Tyr Asp Arg
    50              55              60

Asn Gly Arg Val Glu Leu Asp Glu Ile Pro Lys Pro Lys Glu Trp
65              70              75              80

Glu Ser Pro Leu Lys Ala Phe Glu Ala Ala Tyr Glu His Glu Lys Phe
            85              90              95
```

-continued

```
Ile Ser Lys Ser Ile Tyr Glu Leu Ala Ala Leu Ala Glu Glu Glu Lys
            100                 105                 110

Asp Tyr Ser Thr Arg Ala Phe Leu Glu Trp Phe Ile Asn Glu Gln Val
            115                 120                 125

Glu Glu Glu Ala Ser Val Lys Lys Ile Leu Asp Lys Leu Lys Phe Ala
130                 135                 140

Lys Asp Ser Pro Gln Ile Leu Phe Met Leu Asp Lys Glu Leu Ser Ala
145                 150                 155                 160

Arg Ala Pro Lys Leu Pro Gly Leu Leu Met Gln Gly Gly Glu
                165                 170

<210> SEQ ID NO 6
<211> LENGTH: 167
<212> TYPE: PRT
<213> ORGANISM: Pyrococcus furiosus

<400> SEQUENCE: 6

Met Leu Ser Lys Asp Ile Ile Lys Leu Leu Asn Glu Gln Val Asn Lys
1               5                   10                  15

Glu Met Asn Ser Ser Asn Leu Tyr Met Ser Met Ser Ser Trp Cys Tyr
            20                  25                  30

Thr His Ser Leu Asp Gly Ala Gly Leu Phe Leu Phe Asp His Ala Ala
            35                  40                  45

Glu Glu Tyr Glu His Ala Lys Lys Leu Ile Ile Phe Leu Asn Glu Asn
    50                  55                  60

Asn Val Pro Val Gln Leu Thr Ser Ile Ser Ala Pro Glu His Lys Phe
65                  70                  75                  80

Glu Gly Leu Thr Gln Ile Phe Gln Lys Ala Tyr Glu His Glu Gln His
            85                  90                  95

Ile Ser Glu Ser Ile Asn Asn Ile Val Asp His Ala Ile Lys Ser Lys
            100                 105                 110

Asp His Ala Thr Phe Asn Phe Leu Gln Trp Tyr Val Ala Glu Gln His
            115                 120                 125

Glu Glu Glu Val Leu Phe Lys Asp Ile Leu Asp Lys Ile Glu Leu Ile
            130                 135                 140

Gly Asn Glu Asn His Gly Leu Tyr Leu Ala Asp Gln Tyr Val Lys Gly
145                 150                 155                 160

Ile Ala Lys Ser Arg Lys Ser
                165

<210> SEQ ID NO 7
<211> LENGTH: 183
<212> TYPE: PRT
<213> ORGANISM: Homo sapiens

<400> SEQUENCE: 7

Met Thr Thr Ala Ser Thr Ser Gln Val Arg Gln Asn Tyr His Gln Asp
1               5                   10                  15

Ser Glu Ala Ala Ile Asn Arg Gln Ile Asn Leu Glu Leu Tyr Ala Ser
            20                  25                  30

Tyr Val Tyr Leu Ser Met Ser Tyr Tyr Phe Asp Arg Asp Asp Val Ala
            35                  40                  45

Leu Lys Asn Phe Ala Lys Tyr Phe Leu His Gln Ser His Glu Glu Arg
    50                  55                  60

Glu His Ala Glu Lys Leu Met Lys Leu Gln Asn Gln Arg Gly Gly Arg
65                  70                  75                  80
```

-continued

```
Ile Phe Leu Gln Asp Ile Lys Lys Pro Asp Cys Asp Asp Trp Glu Ser
            85                  90                  95

Gly Leu Asn Ala Met Glu Cys Ala Leu His Leu Glu Lys Asn Val Asn
            100                 105                 110

Gln Ser Leu Leu Glu Leu His Lys Leu Ala Thr Asp Lys Asn Asp Pro
        115                 120                 125

His Leu Cys Asp Phe Ile Glu Thr His Tyr Leu Asn Glu Gln Val Lys
    130                 135                 140

Ala Ile Lys Glu Leu Gly Asp His Val Thr Asn Leu Arg Lys Met Gly
145                 150                 155                 160

Ala Pro Glu Ser Gly Leu Ala Glu Tyr Leu Phe Asp Lys His Thr Leu
            165                 170                 175

Gly Asp Ser Asp Asn Glu Ser
            180

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Gly Gly Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9

His His His His His His
1               5

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tccatgacgt tcctgacgtt                                               20
```

FERRITIN NANOPARTICLE DISPLAYING AN HIV TRIMER

RELATED APPLICATIONS AND INCORPORATION BY REFERENCE

This application claims priority to U.S. provisional patent application Ser. No. 62/681,051 filed 5 Jun. 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under Grant Nos. AI100663, AI104715, A1048240, and CA014051 awarded by the National Institutes of Health. The government has certain rights in the invention.

FIELD OF THE INVENTION

The present invention relates to nanoparticle-based vaccine compositions and methods. The nanoparticles are rapidly shuttled to the follicular dendritic cell (FDC) network and targeted to germinal centers in a complement-, mannose-binding-lectin (MBL)-, and immunogen-glycan-dependent manner. The invention provides novel glycoproteins which may be utilized as HIV-1 vaccine immunogens and for identification of HIV antibodies. The invention encompasses preparation and purification of immunogenic compositions which are formulated into vaccines of the present invention.

BACKGROUND OF THE INVENTION

AIDS, or Acquired Immunodeficiency Syndrome, is caused by human immunodeficiency virus (HIV) and is characterized by several clinical features including wasting syndromes, central nervous system degeneration and profound immunosuppression that results in opportunistic infections and malignancies. HIV is a member of the lentivirus family of animal retroviruses, which include the visna virus of sheep and the bovine, feline, and simian immunodeficiency viruses (SIV). Two closely related types of HIV, designated HIV-1 and HIV-2, have been identified thus far, of which HIV-1 is by far the most common cause of AIDS. However, HIV-2, which differs in genomic structure and antigenicity, causes a similar clinical syndrome.

An infectious HIV particle consists of two identical strands of RNA, each approximately 9.2 kb long, packaged within a core of viral proteins. This core structure is surrounded by a phospholipid bilayer envelope derived from the host cell membrane that also includes virally encoded membrane proteins (Abbas et al., Cellular and Molecular Immunology, 4th edition, W.B. Saunders Company, 2000, p.

454). The HIV genome has the characteristic 5'-LTR-Gag-Pol-Env-LTR-3' organization of the retrovirus family. Long terminal repeats (LTRs) at each end of the viral genome serve as binding sites for transcriptional regulatory proteins from the host and regulate viral integration into the host genome, viral gene expression, and viral replication.

The HIV genome encodes several structural proteins. The gag gene encodes structural proteins of the nucleocapsid core and matrix. The pol gene encodes reverse transcriptase (RT), integrase (IN), and viral protease (PR) enzymes required for viral replication. The tat gene encodes a protein that is required for elongation of viral transcripts. The rev gene encodes a protein that promotes the nuclear export of incompletely spliced or unspliced viral RNAs. The vif gene product enhances the infectivity of viral particles. The vpr gene product promotes the nuclear import of viral DNA and regulates G2 cell cycle arrest. The vpu and nef genes encode proteins that down regulate host cell CD4 expression and enhance release of virus from infected cells. The env gene encodes the viral envelope glycoprotein that is translated as a 160-kilodalton (kDa) precursor (gp160) and cleaved by a cellular protease to yield the external 120-kDa envelope glycoprotein (gp120) and the transmembrane 41-kDa envelope glycoprotein (gp41), which are required for the infection of cells (Abbas et al., Cellular and Molecular Immunology, 4th edition, W.B. Saunders Company, 2000, pp. 454-456). gp140 is a modified form of the Env glycoprotein, which contains the external 120-kDa envelope glycoprotein portion and the extracellular part of the gp41 portion of Env and has characteristics of both gp120 and gp41. The nef gene is conserved among primate lentiviruses and is one of the first viral genes that is transcribed following infection. In vitro, several functions have been described, including down-regulation of CD4 and MHC class I surface expression, altered T-cell signaling and activation, and enhanced viral infectivity.

HIV infection initiates with gp120 on the viral particle binding to the CD4 and chemokine receptor molecules (e.g., CXCR4, CCR5) on the cell membrane of target cells such as CD4+ T-cells, macrophages and dendritic cells. The bound virus fuses with the target cell and reverse transcribes the RNA genome. The resulting viral DNA integrates into the cellular genome, where it directs the production of new viral RNA, and thereby viral proteins and new virions. These virions bud from the infected cell membrane and establish productive infections in other cells. This process also kills the originally infected cell. HIV can also kill cells indirectly because the CD4 receptor on uninfected T-cells has a strong affinity for gp120 expressed on the surface of infected cells. In this case, the uninfected cells bind, via the CD4 receptor-gp120 interaction, to infected cells and fuse to form a syncytium, which cannot survive. Destruction of CD4+T-lymphocytes, which are critical to immune defense, is a major cause of the progressive immune dysfunction that is the hallmark of AIDS disease progression. The loss of CD4+ T cells seriously impairs the body's ability to fight most invaders, but it has a particularly severe impact on the defenses against viruses, fungi, parasites and certain bacteria, including mycobacteria.

Viruses have evolved a variety of mechanisms to escape antibody recognition, many of which involve features of the viral surface proteins, such as high variability, steric occlusion, and glycan coating. For HIV, the dense shield of glycans that decorate the viral Env protein was once believed to be refractory to antibody recognition, shielding conserved protein epitopes of important functional significance whose greater exposure would result in increased susceptibility to antibody neutralization.

Citation or identification of any document in this application is not an admission that such document is available as prior art to the present invention.

SUMMARY OF THE INVENTION

In vaccine design, antigens are often arrayed in a multivalent nanoparticle form, but in vivo mechanisms underlying the enhanced immunity elicited by such vaccines remain poorly understood. The inventors have discovered methods and compositions for enhanced humoral immunity. According to the invention, certain arrangements of glycosylated HIV antigens in multivalent forms promote binding to mannose-binding lectin, complement fixation, and antigen trafficking to follicular dendritic cells.

The present invention relates to nanoparticles comprising HIV epitopes, such as, without limitation, trimer nanoparticles, which may comprise MD39 or variants thereof, fused to self-assembling ferritin proteins, as immunogens to enhance trafficking to lymph nodes and germinal centers, and to heighten immune responses.

The invitation also demonstrates glycosylation of protein nanoparticles affords improved trafficking to lymph nodes and germinal centers, generally leading to stronger immune responses.

A tenet of vaccine design is that antigen must reach lymph nodes. Humoral responses are initiated in distinct compartments called B cell zones or lymphoid follicles, where follicular dendritic cells (FDCs) display antigen to B cells and facilitate affinity maturation. However, many nanoparticles never reach B cell zones but are directed or trapped elsewhere. Without being bound by theory, the inventors have found that nanoparticles displaying glycosylated HIV antigens reach B cell zones and colocalize with FDCs in a process mediated by mannose-binding lectin (MBL).

In an aspect of the invention, there is provided a synthetic peptide which comprises a glycosylated Env peptide of HIV and a support peptide, wherein the synthetic peptide form a self-assembling nanoparticle, whereby there is transport to the follicular dendritic cell (FDC) network and complement-dependent, mannose-binding-lectin (MBL)-dependent, and/or immunogen-glycan-dependent transport to germinal centers. In certain embodiments of the invent the Env peptide is glycosylated with oligomannose.

In certain embodiments, the support peptide comprises at least 25 contiguous amino acids that are at least 80% identical to a bacterial ferritin, a plant ferritin, an algal ferritin, an insect ferritin, a fungal ferritin or a mammalian ferritin. In certain embodiments, the support peptide comprises at least 25 contiguous residues that are at least 80% identical to *Pyrococcus* furioso ferritin (SEQ ID NO:5). In other embodiments, the ferritin comprises at least 25 contiguous residues that are at least 80% identical to *Helicobacter pylori* ferritin (SEQ ID NO:6). In further embodiments, the ferritin comprises at least 25 contiguous residues that are at least 80% identical to a mammalian ferritin, for example but not limited to human ferritin. In certain embodiments, the support peptide comprises lumazine synthase (LS) or a fragment thereof.

Examples of the peptides include, without limitation, BG505_SOSIP_MD39_JD6_m (SEQ ID NO:1), BG505_MD39_G41_2JD6 (SEQ ID NO:2), BG505_MD39_link14_2JD6 (SEQ ID NO:3), or BG505_MD39_3bve_m (SEQ ID NO:4).

In another aspect, the invention provides a nanoparticle which comprises a plurality of peptides as set forth above. In another aspect, the invention provides nucleic acids that encode the peptides.

The invention further provides vectors comprising the nucleic acids, such as without limitation vectors comprising a regulatory element operable in a eukaryotic cell operably linked to the nucleic acids. In certain embodiments, the vector comprises a viral vector. In certain embodiments, the vector comprises AAV.

In an aspect, the invention provides a method of eliciting an immune response in a mammal comprising administering a peptide or nanoparticle of the invention. In certain embodiments, the method stimulates a broadly neutralizing HIV antibody (bnAb) in a mammal. In certain embodiments, the method stimulates a germline precursor of a bnAb. In certain embodiments, the mammal is a human. In other embodiments, the mammal is a non-human primate. In further embodiments the mammal is a mouse. In certain embodiment, the mammal comprises elements of a human immune system.

In certain embodiment, the method comprises administering two or more peptides or two or more nanoparticles of the invention. In certain such embodiments, the peptides or nanoparticles are administered sequentially. In other embodiments, the peptides or nanoparticles are administered together, for example in the same composition or at the same time. In an embodiment of the invention, the peptides or nanoparticles are administered with an adjuvant. Such adjuvants include, with limitation, lecithins, which can be combined with an acrylic polymer, in a coated oil droplet in an oil-in-water emulsion or in an acrylic polymer in an oil-in-water emulsion. Non-limiting examples of adjuvants include ISCOMATRIX, Adjuplex, and alum. In certain embodiments, vaccine components are fixed, for example in glutaraldehyde, and optionally quenched, for example with glycine.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

9 eOD-60mer, MD39 trimer, MD39-8mer and HA-8mer. Peaks sensitive to endoglycosidase H (endoH) digestion are colored green and represent oligomannose- or hybrid-type glycans. Peaks resistant to endoH are colored magenta and represent complex-type glycans. The first pie chart depicts the quantification of oligomannose-type glycans in each sample. The second pie chart displays the quantification of the fine processing of complex-type glycans. Complex-type glycans containing $\alpha2,3$ sialic acid residues are colored purple, $\alpha2,6$ sialic acid are colored red and those terminating with a $\beta1,4$ galactose residue are colored yellow. Other N-linked glycans corresponding to complex-type or hybrid-type glycans are colored grey. Peaks corresponding to the series of oligomannose-type glycans ($Man_{5-9}GlcNAc_2$) are annotated with symbolic representation of the most abundant isomer.

Figures 15A, 15B, 15C:
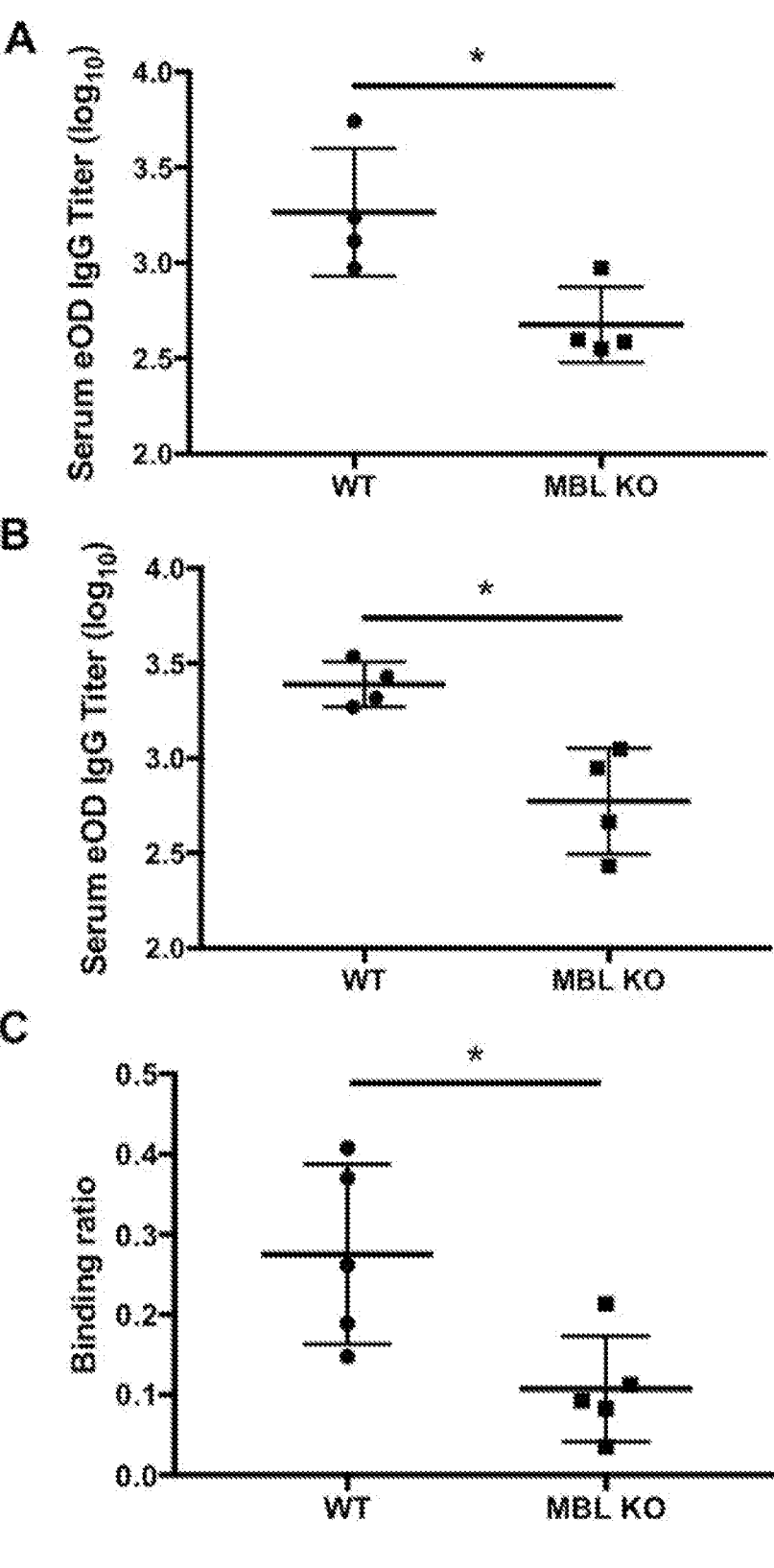

FIG. 15A-15C. Humoral responses to eOD antigen are reduced in MBL KO animals immunized with multiple adjuvants. (A, B) Groups of C57Bl/6 or MBL KO animals (n=4/group) were immunized with 3.7 µg eOD-60mer (equivalent to 2 µg eOD) mixed with (A) 10 µg MPLA or (B) 20 µg CpG DNA, and serum IgG titers were assessed two weeks later by ELISA. (C) Sera from C57Bl/6 (WT) or MBL KO mice (n=5/group) immunized as in FIG. 4J were assayed for eOD-specific IgG by ELISA using plates coated with high or low densities of eOD antigen. Shown is the ratio of titers for binding on low-density plates to that measured on high-density plates as a measure of relative polyclonal antibody avidity. *, p<0.05 by two-tailed t test. Shown are mean and SD.

Figure 16:
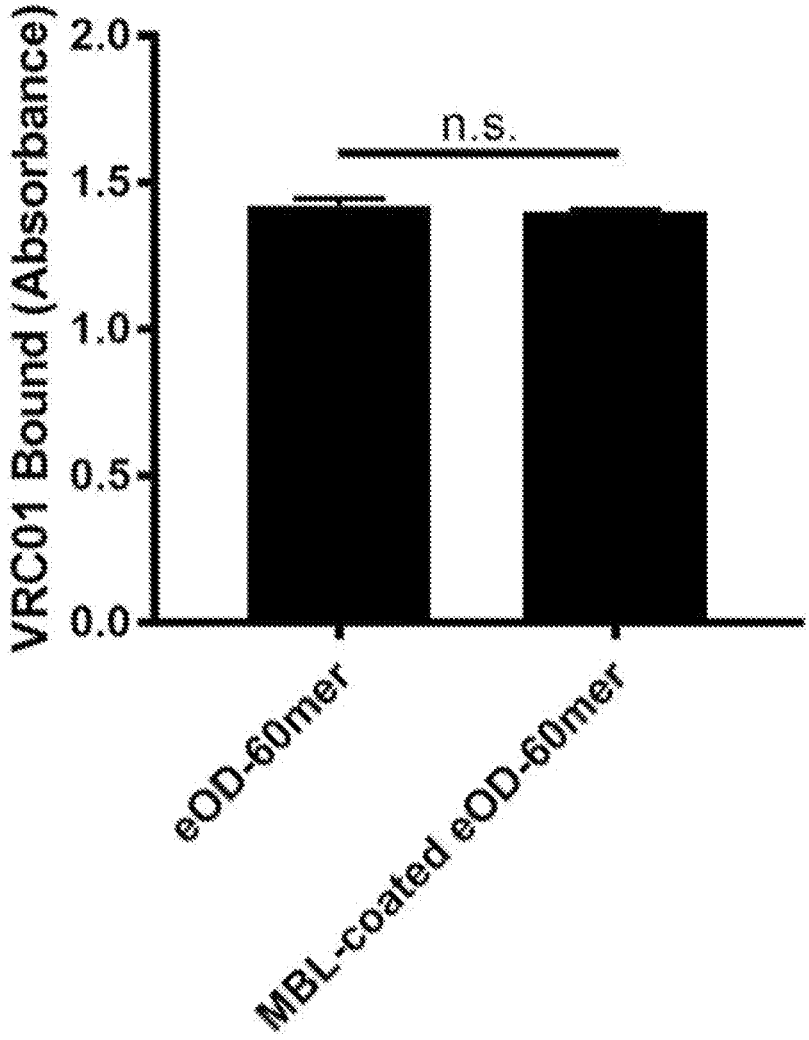

FIG. 16. VRC01 binding to MBL-coated eOD-60mer. Following plate coating with 2 µg/ml eOD-60mer, wells were incubated with either 5 µg/ml mouse MBL or buffer, and the plates were washed four times. Mouse VRC01 was then added at a concentration of 1 µg/ml and detected with a goat anti-mouse IgG-HRP antibody conjugated. Analyzed using t test. Shown are mean and SD.

Figure 17A:
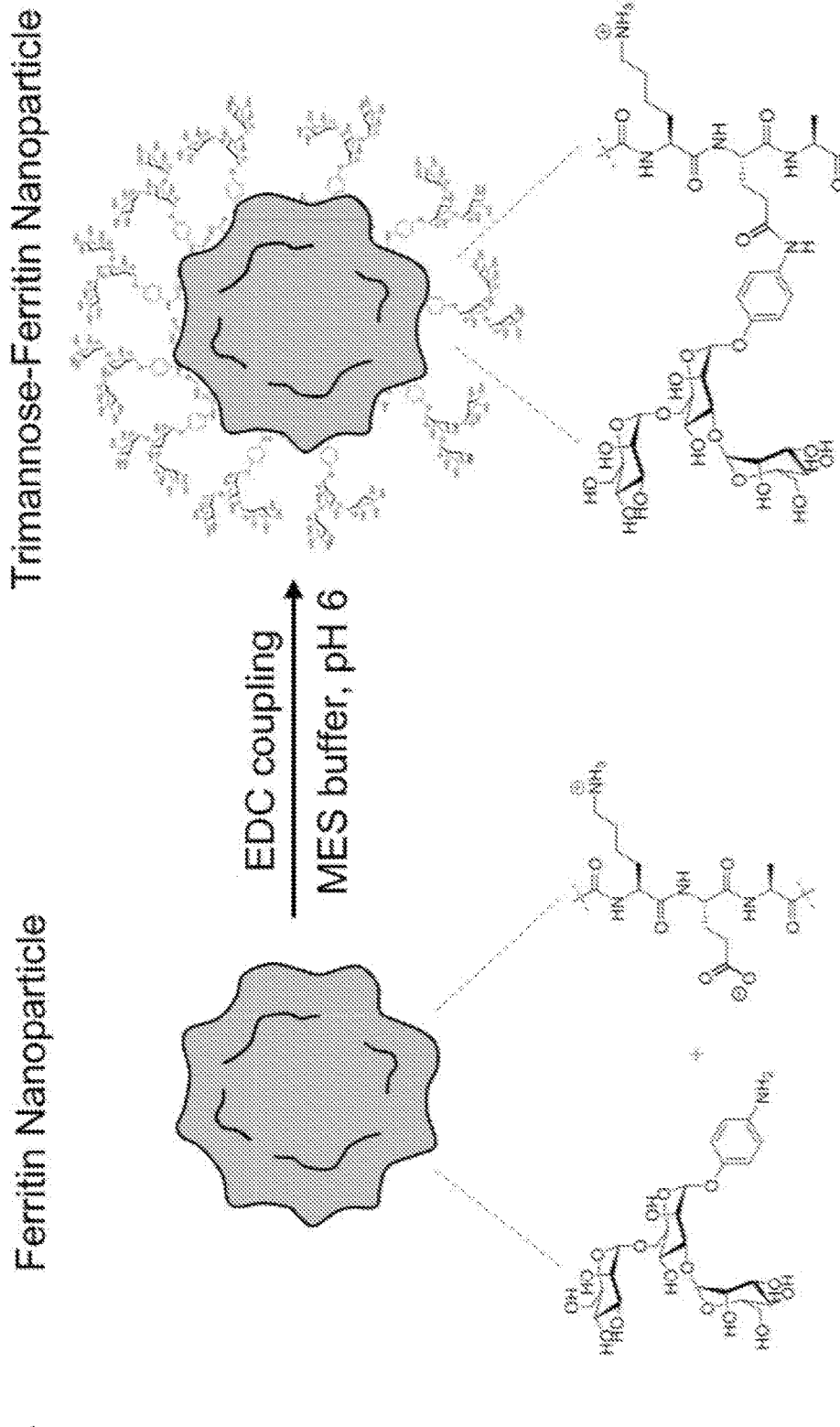
Figure 17B:
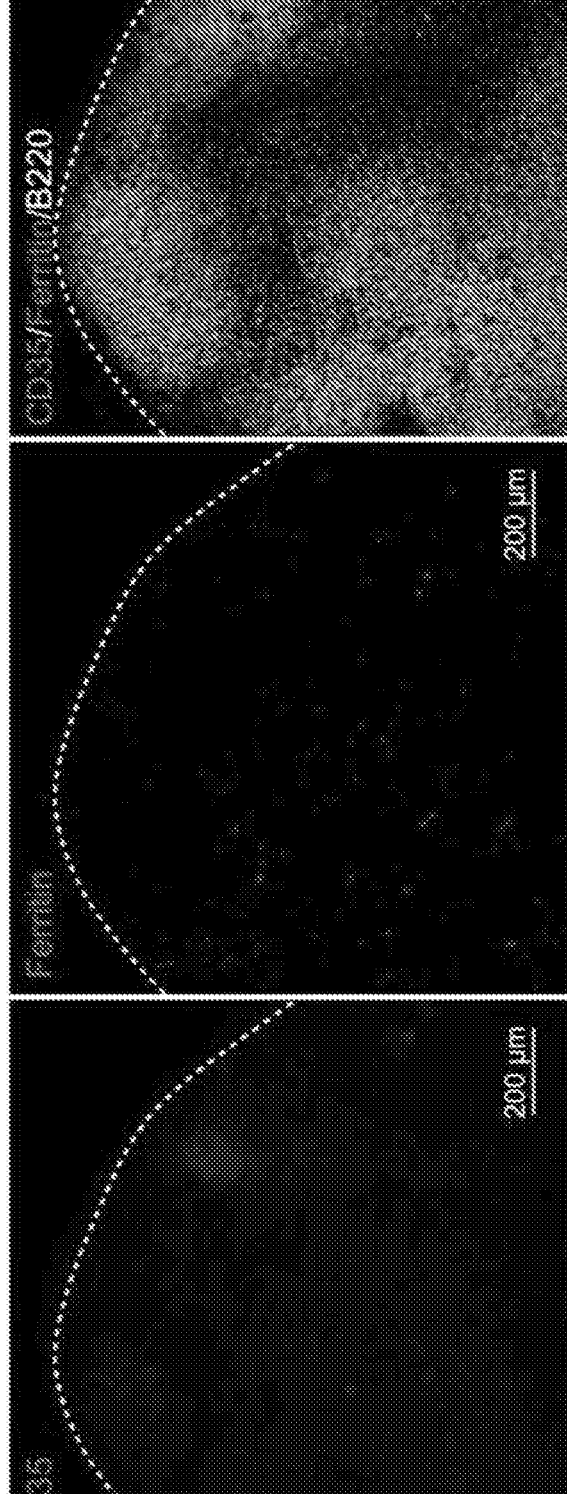

FIG. 17A-17B. Trimannose functionalization of ferritin nanoparticles. (A) Chemistry of trimannose coupling to ferritin nanoparticles. (B) Groups of balb/c mice (n=3 animals/group) were immunized with 5 µg ferritin nanoparticles conjugated a low density of trimannose groups (~25 trimannose per particle) together with adjuvant. Lymph nodes were excised on day 7, fixed, sectioned, and imaged by confocal microscopy.

Figure 18A:
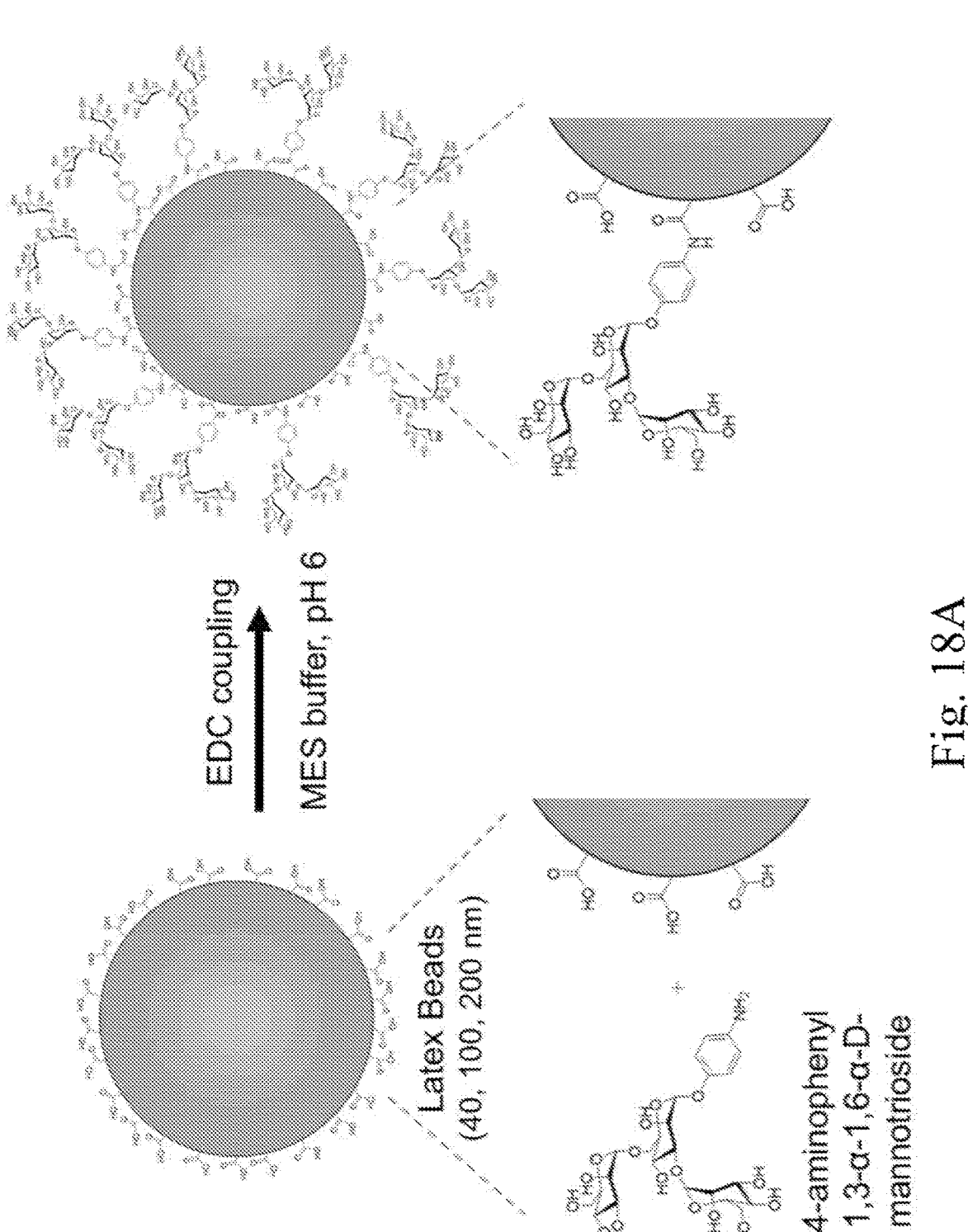
Figure 18B:
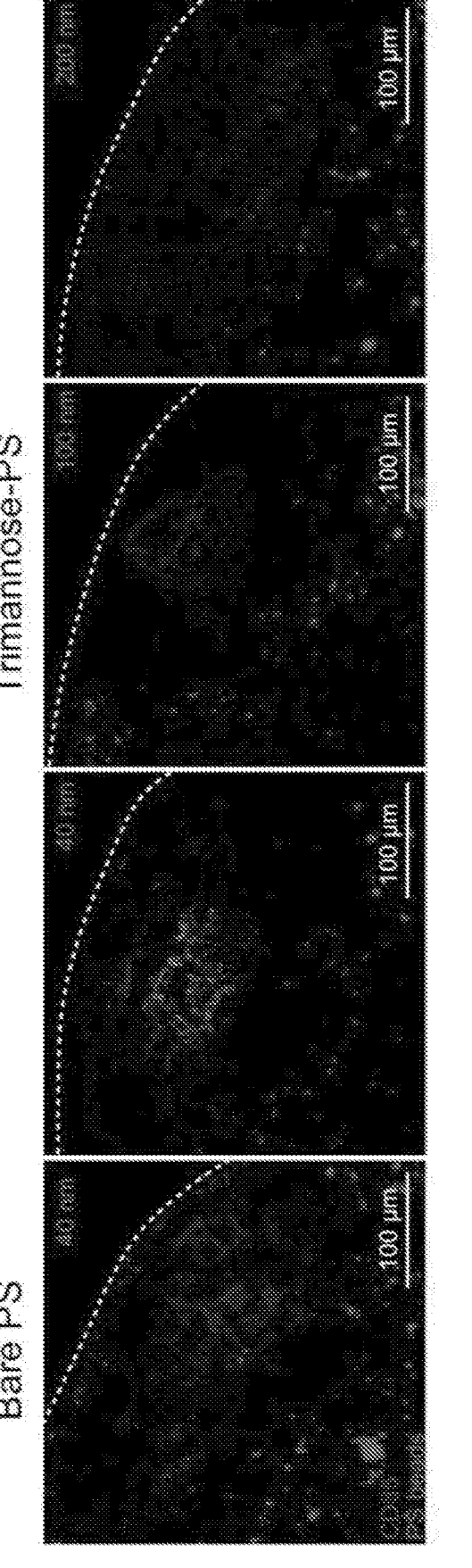

FIG. 18A-18B. Trimannose functionalization of small synthetic nanoparticles promotes FDC localization in lymph nodes. (A) Chemistry of trimannose coupling to polystyrene nanoparticles. (B) Groups of balb/c mice (n=3 animals/group) were immunized with 10 µg polystyrene (PS) nanoparticles of 40 nm, 100 nm, or 200 nm diameter conjugated with trimannose or not together with adjuvant. Lymph nodes were excised on day 7, fixed, sectioned, and imaged by confocal microscopy.

The figures herein are for illustrative purposes only and are not necessarily drawn to scale.

DETAILED DESCRIPTION OF THE INVENTION

Synthetic nanoparticles have attracted widespread interest for vaccine design, but how the immune system generates a response to multimeric nanoparticles remains unclear. In an aspect, the invention provides HIV envelope antigens arranged in either multivalent nanoparticle forms or as single monomers. The nanoparticle HIV immunogens trigger greater antibody responses compared with the monomeric forms.

In an aspect, the invention relates to glycosylation for enhanced humoral immunity. In certain embodiments, glycosylation promotes binding to mannose-binding lectin. In certain embodiments, glycosylation promotes complement fixation. In certain embodiments, glycosylation promotes antigen trafficking to follicular dendritic cells.

Accordingly, in certain embodiments, the invention includes methods of increasing levels of glycosylation, also referred to as "glycan density" or "glycan content," of hybrid peptides and nanoparticles described herein. The number of added glycans of a hybrid peptide can be 1, 2, 3, 4, 5, 6, 7, 8, 9, 10, or more. In certain embodiments, hybrid peptides and nanoparticles have glycans added to the HIV env portion, in certain embodiments glycans are added to the carrier portion, and in certain embodiments glycans are added to both the HIV env portion and the carrier portion. In this regard, adding comprises increasing the number of glycans as compared to a naturally occurring peptide as well as increasing the number of glycans in a synthetic peptide as compared to the protein or peptide from which it was developed (e.g., adding glycans to an engineered HIV Env protein or polypeptide relative to an earlier known or discovered HIV Env protein or polypeptide and/or adding glycans to an engineered carrier protein or polypeptide compared to an earlier know or discovered polypeptide). Accordingly, the number of glycans added to a nanoparticle comprised of hybrid peptides of the invention can be may multiples of the individual peptides, depending on the peptide content of the nanoparticle. For example, the number of added glycans in an 8-mer or 60-mer can be many multiples of the numbers added to an individual hybrid peptide as well as intermediate numbers as the nanoparticles need not be identically glycosylated on each of their incorporated hybrid peptides. Accordingly, glycans can be increased by 1, 2, 3, 4, 5, 6, 7, 8, 9, 10, about 12, about 14, about 16, about 18, about 20, about 25, about 30, about 35, about 40, about 50, about 60, about 70, about 80, about 90, about 100, about 200, about 300, about 400, about 500, about 600, about 700, about 800, about 1000, or more.

The effect of increased glycan content can be observed by increased complement-dependent, mannose-binding-lectin (MBL)-dependent, and/or immunogen-glycan-dependent transport of nanoparticles to germinal centers, for example as described further herein.

Nature-derived nanocarriers are advantageous alternatives to synthetic ones as they satisfy certain key features, such as biocompatibility, water solubility and high cellular uptake efficiency with minimal toxicity. Examples of nature-derived nanocarriers include protein nanocages such as viruses, ferritin and many others that are formed by the self-assembly of protein subunits, resulting in a cage-like structure. The subunits are modifiable through chemical and genetic methods. For further description of structures and uses of such materials, see, e.g., Bhaskar, S. et al., Engineering protein nanocages as carriers for biomedical applications, NPG Asia Materials volume 9, page e371 (2017).

Ferritin

Almost all living organisms produce ferritin, a protein whose main function is intracellular iron storage. Ferritin is made of 24 subunits, each composed of a four-alpha-helix bundle, that self-assemble in a quaternary structure with octahedral symmetry. Several high-resolution structures of ferritin have been determined, confirming that in bacterian (e.g., *Helocobacter pylori*), ferritin comprises 24 identical protomers, whereas in animals, there are ferritin light and heavy chains that can assemble alone or combine with different ratios into particles of 24 subunits (39, 40). Ferritin self-assembles into nanoparticles with robust thermal and chemical stability. Hence, the ferritin nanoparticle is potentially well-suited to carry and expose immunogens. Moreover, since ferritin is composed of eight units each with three-fold axis symmetry, it is a convenient scaffold for the presentation of trimeric antigens.

Ferritin is useful as an antigen support in the search for vaccines against HIV (38). For example, in order to circumvent the fact that Abs others than the so-called broadly neutralizing antibodies (bNAbs) might occlude highly vulnerable HIV sites, a series of these HIV target motifs were grafted into different protein templates and the resultant chimeras were named 'supersite transplants.' Transplants bearing a glycopeptide from the variable region 3 on gp120 were recognized by neutralizing antibodies from three different donors, and binding was enhanced by presentation of the transplants on ferritin nanoparticles.

Preferably, the monomeric ferritin subunit protein is selected from the group consisting of a bacterial ferritin, a plant ferritin, an algal ferritin, an insect ferritin, a fungal ferritin and a mammalian ferritin. In certain embodiments, the monomeric ferritin subunit protein is a monomeric subunit of a *Pyrococcus furiosus* ferritin protein. In certain embodiments, the monomeric ferritin subunit protein is a monomeric subunit of a *Helicobacter pylori* ferritin protein. Preferably, the monomeric ferritin peptide comprises at least 25, at least 30, at least 35, at least 40, at least 45, at least 50, at least 55, at least 60, at least 65, at least 70, at least 75, at least 80, at least 85, at least 90, at least 95, or at least 100 amino acids of an amino acid sequence of an isolated, recombinant or synthetic ferritin protein as described above, such that, such that the nanoparticle comprises HIV Env trimers on its surface. In certain embodiments, the monomeric ferritin sequence comprises amino acids from 1 to 30, 1 to 40, 1 to 50, 1 to 60, 1 to 70, 1 to 80, 1 to 90, 1 to 100, 1 to 110, 1 to 120, 1 to 130, 1 to 140, 1 to 150, 1 to 160, 1 to 170, 20 to 50, 20 to 60, 20 to 70, 20 to 80, 20 to 90, 20 to 100, 20 to 110, 20 to 120, 20 to 130, to 140, 20 to 150, 20 to 160, 20 to 170, 40 to 70, 40 to 80, 40 to 90, 40 to 100, 40 to 110, 40 to 120, 40 to 130, 40 to 140, 40 to 150, 40 to 160, 40 to 170, 60 to 90, 60 to 100, 60 to 110, 60 to 120, 60 to 130, 60 to 140, 60 to 150, 60 to 160, 60 to 170, 80 to 110, 80 to 120, 80 to 130, 80 to 140, 80 to 150, 80 to 160, 80 to 170, 100 to 130, 100 to 140, 100 to 150, 100 to 160, 100 to 170, 120 to 150, 120 to 160, 120 to 170, or 140 to 170.

Preferably, the monomeric ferritin peptide has at least 80%, at least 85%, at least 90%, at least 92%, at least 94%, at least 95%, at least 96%, at least 97%, at least 98%, or at least 99% sequence identity to the isolated, recombinant or synthetic protein as described above. As used herein, the terms 'percent similarity,' 'percent identity,' and 'percent homology' when referring to a particular sequence are used as set forth in the University of Wisconsin GCG software program.

Lumazine

Lumazine synthase (LS) is another example of a bacterial particulate useful for optimization of vaccine candidates. Jardine et al. used LS to enhance the immunoreactivity of recombinant gp120 against HIV infection (6). A key hurdle is the low recognition potential of germline precursors of broadly neutralizing antibodies (bNAbs), such as VRC01, against the wild type gp120, the major immunogenic component of the HIV virus envelope. One way to overcome this obstacle is to boost the affinity of the germline antibodies for the viral gp120 glycoprotein by displaying multiple copies of an engineered form of the antigen on a lumazine synthase (LS) nanoparticle (6). LS is an enzyme present in a broad variety of organisms, including archea, bacteria, fungi, plants, and eubacteria. The LS monomer is 150 amino acids long, and consists of beta-sheets along with tandem alpha-helices flanking its sides and a number of different quaternary structures have been reported.

LS has been engineered display an optimized sub-component (termed, eOD-GT6) of the wild-type gp120 antigen from the Env trimer (38). With additional structural stabilization of the trimer provided by an N-terminal coiled-coil GCN4 domain, the eOD-GT6 immunogen was fused to the C-terminus of the LS construct. The resulting recombinant nanoparticle antigens were efficiently obtained from mammalian cells, in stable and homogeneous self-assemblies of 60 LS monomers each presenting a glycosylated eOD-GT6. This approach overcame the issue that germline precursors of VRC01 bNAbs show undetectable affinity for wild-type Env. In contrast with the monomeric eOD-GT6 that did not stimulate B cell activation, the LS-eOD-GT6 nanoparticles activated both germline and mature B cells.

In certain embodiments, the Env peptide is linked at the C terminus end to the N terminus of the carrier peptide. In certain embodiments, the Env peptide is inserted into the carrier peptide, for example at or near a surface-exposed loop of the carrier peptide. Such locations will be evident from the structure of the carrier peptide. For example, as to non-limiting examples of carrier peptide structure, atomic coordinates for the 3D structure of ferritin from *Pyrococcus furiosus* may be those of PDB:2X17; atomic coordinates for the 3D structure of human L ferritin may be those of PDB:2FFX; atomic coordinates for the 3D structure of human H ferritin with genetically engineered intermolecular contacts may be those of PDB:1FHA; atomic coordinats for the 3D structure of *Aquifex* aeolicus lumazine synthase may be those of PDB:1HQK. The 3D structures of many ferritins have been solved. Alternatively or in addition, sufficient information to identify insertion points in any ferritin can be obtained from comparisons with ferritins having solved structures.

The invention pertains to the identification, design, synthesis and isolation of molecules from HIV proteins, peptides, fragments, and mutants thereof that bind to HIV directed antibodies. The invention also pertains to molecules from SIV proteins, peptides, fragments, and mutants thereof used as immunogens to stimulate HIV directed antibodies, especially bnAbs that bind to HIV as well as nucleic acids encoding the same. The immunogens may comprise proteins, peptides, fragments, such as the various trimers disclosed herein The present invention also relates to homologues, derivatives and variants of the sequences of the mutant trimers and nucleic acids encoding the same, wherein it is preferred that the homologue, derivative or variant have at least 50%, at least 60%, at least 70%, at least 75%, at least 80%, at least 85%, at least 90%, at least 93%, at least 95%, at least 97%, at least 98% or at least 99% homology or identity with the sequence of the mutant trimers and nucleic acids encoding the same. It is noted that within this specification, homology to sequences of the mutant proteins and nucleic acids encoding the same refers to the homology of the homologue, derivative or variant to the binding site of the mutant proteins and nucleic acids encoding the same.

The invention still further relates to nucleic acid sequences expressing the proteins, peptides, fragments, trimers, and mutants disclosed herein, or homologues, variants or derivatives thereof and the epitopes presented thereon. One of skill in the art will know, recognize and understand techniques used to create such. Additionally, one of skill in the art will be able to incorporate such a nucleic acid sequence into an appropriate vector, allowing for production of the amino acid sequence of mutant proteins and nucleic acids encoding the same or a homologue, variant or derivative thereof.

The proteins, peptides, fragments, trimers, and mutants disclosed herein, or homologues, variants or derivatives thereof and the epitopes presented thereon may also be useful in screening for ligands that bind to said epitopes. Such ligands preferably block the epitopes and thus prevent infection.

Where used herein and unless specifically indicated otherwise, the following terms are intended to have the following meanings in addition to any broader (or narrower) meanings the terms might enjoy in the art:

The term "isolated" or "non-naturally occurring" is used herein to indicate that the isolated moiety (e.g. peptide or compound) exists in a physical milieu distinct from that in which it occurs in nature. For example, the isolated peptide may be substantially isolated with respect to the complex cellular milieu in which it naturally occurs. The absolute level of purity is not critical, and those skilled in the art may readily determine appropriate levels of purity according to the use to which the peptide is to be put. The term "isolating" when used a step in a process is to be interpreted accordingly.

In many circumstances, the isolated moiety will form part of a composition (for example a more or less crude extract containing many other molecules and substances), buffer system, matrix or excipient, which may for example contain other components (including proteins, such as albumin).

In other circumstances, the isolated moiety may be purified to essential homogeneity, for example as determined by PAGE or column chromatography (for example HPLC or mass spectrometry). In preferred embodiments, the isolated peptide or nucleic acid of the invention is essentially the sole peptide or nucleic acid in a given composition.

In an advantageous embodiment, a tag may be utilized for purification or biotinylation. The tag for purification may be a his tag. In another embodiment, the tag for biotinylation may be an avi-tag. Other tags are contemplated for purification, however, purification may be accomplished without a tag. In another embodiment, antibody (such as, not limited to, a broadly neutralizing antibody) affinity columns are contemplated. In another embodiment, lectin columns are contemplated.

Native-like soluble trimers can be made by several methods that all involve stabilizing associations between envelope protein subunits. See, e.g., P. Dosenovic et al, "Immunization for HIV-1 broadly neutralizing antibodies in human Ig knockin mice," Cell, 161:1-11, 2015; J. G. Jardine et al, "Priming a broadly neutralizing antibody response to HIV-1 using a germline targeting immunogen," Science, doi: 10.1126/science.aac5894, 2015 and R. W. Sanders et al, "HIV-1 neutralalizing antibodies induced by native-like envelope trimers," Science, doi: 10.1 126/science. aac4223, 2015.

The proteins and compounds of the invention need not be isolated in the sense defined above, however.

Compounds which have a chemical structure selected using the invention, wherein said compounds are neutralizing antibody binders, form a further aspect of the invention; and, such compounds may be used in methods of medical treatments, such as for diagnosis, preventing or treating HIV or for eliciting antibodies for diagnosis of HIV, including use in vaccines. Further, such compounds may be used in the preparation of medicaments for such treatments or prevention, or compositions for diagnostic purposes. The compounds may be employed alone or in combination with other treatments, vaccines or preventatives; and, the compounds may be used in the preparation of combination medicaments for such treatments or prevention, or in kits containing the compound and the other treatment or preventative.

The invention relates to immunogenic molecules that bind to and stimulate antibody production, particularly molecules that efficiently stimulate germline antibodies that are broadly neutralizing and/or precursors to antibodies that are broadly neutralizing against epitopes common to a variety or HIV isolates. The common epitopes may be evolutionarily selected and not especially immunogenic. Thus it can be beneficial to present antigenic molecules to the immune system that efficiently stimulate antibodies that bind to the common epitope while avoiding antibodies directed at epitopes that are not broadly neutralizing.

In certain embodiments, germline reverted antibodies can be identified by comparing the heavy and light chains of an isolated bnAb that binds to an epitope of interest to nucleotide sequences and/or the amino acid sequences potentially encoded by germline V gene segments. For example, one can obtain a germline reverted antibody starting from the amino acid sequence of an antibody directed to an antigen or epitope of choice and identifying germline encoded antibody segments (i.e., heavy chain V, D, and J gene segments and light chain V and J gene segments closest to the starting antibody. Germline variable genes are cataloged, for example at VBASE2 (Retter I, Althaus H H, Munch R, Müller W: VBASE2, an integrative V gene database. Nucleic Acids Res. 2005 Jan. 1; 33(Database issue):D671-4.). Starting from a known or preselected antibody and moving to such a database can be advantageous for example as the paired heavy and light chains will be compatible and likely to be well represented in the repertoire of expressed germline genes.

Germline genes that bind to an epitope of interest can also be identified by screening libraries of human heavy and light chain genes, for example by phage display. Another method is by immunization and preparation of monoclonal antibodies from a mouse that expresses human antibody genes. Preferably hybridomas are prepared before there is substantial somatic mutation and selection. As mentioned, depending on the method employed, it is advantageous to select germline antibody gene segments that are well represented in the repertoire of expressed human antibodies, also taking into account compatibility of various heavy chain-light chain pairings. In certain embodiments, it is advantageous to select V-D, D-J, V-D-J (heavy chain) or V-J (light chain) combinations that are well represented.

Amino acid sequences of the V2 apex regions of many SIV isolates have been determined and can be used or compared with HIV isolates to identify useful conserved epitopes that would be bound by broadly neutralizing antibodies. An analysis may also include modeling or determination of 3D structure to identify interactions with bnAbs. Similar analysis can be done for other HIV reference isolates and SIV counterparts based on conserved structures, regions, and epitopes of the V2 apex, as well other conserved structures, regions, and epitopes that comprise bnAb binding sites to find suitable bases for development of SIV-based molecules and immunogens that bind to and stimulate HIV antibodies.

The HIV envelope protein (Env) is the target of broadly neutralizing antibodies (bnAbs) in natural infection. Env is a membrane protein composed of a trimer of gp120 and gp41 subunits that contains a high degree of sequence diversity and a surface that is shielded by N-linked glycans. The bnAbs that target Env often have unusual features such as a long complementarity-determining region (CDR) H3, high levels of somatic hypermutation (SHM), and insertions and deletions (INDELS). Furthermore, most of the bnAbs recognize complex epitopes that are typically non-linear and have both protein and glycan components.

HIV type I (HIV-I) envelope is a noncovalent trimer of gp120-gp41 heterodimers, and its lability has hindered structural studies. SOSIP gp140 is a soluble, proteolytically mature form of the HIV-I envelope wherein gp120-gp41 interactions are stabilized via a disulfide bond and gp41 contains an additional trimer-stabilizing point mutation. The isolation of a substantially pure preparation of SOSIP gp140 trimers derived from KNH1144, a subtype A isolate was described in Iyer S P et al., AIDS Res Hum Retroviruses. 2007 June; 23(6):817-28. Following initial purification, the only significant contaminant was higher-order gp140 aggregates; however, 0.05% Tween 20 quantitatively converted these aggregates into trimers. The surfactant effect was rapid, dose dependent, and similarly effective for a subtype B SOSIP gp140.

Surfactant-treated SOSIP gp140 retained favorable antigenicity and formed compact trimers 12-13 nm in size as determined by electron microscopy. Iyer S P et al., AIDS Res Hum Retroviruses. 2007 June; 23(6):817-28 provides a description of homogeneous, cleaved HIV-I envelope trimers. These proteins may be useful as vaccine immunogens and for studying structure-function relationships within the HIV-I envelope glycoproteins.

Soluble, stabilized, proteolytically cleaved, trimeric proteins may be generated by engineering an intermolecular disulphide bond between gp120 and gp41 (SOS), combined with a single residue change, I559P, within gp41 (SOSIP). SOSIP gp140 proteins based on the subtype A HIV-I strain KNHI 144 form particularly homogenous trimers compared to a prototypic strain (JR-FL, subtype B). Described in U.S. Pat. No. 7,939,083 are the determinants of this enhanced stability which are located in the N-terminal region of KNHI 1144 gp41 and that, when substituted into heterologous Env sequences (e.g., JR-FL and Ba-L) they have a similarly beneficial effect on trimer stability. These stabilized trimers retain the epitopes for several neutralizing antibodies and related agents (CD4-IgG2, b12, 2G12, 2F5 and 4E10) and the CD4-IgG2 molecule, so that the overall antigenic structure of the gp140 protein has not been adversely impaired by the trimer-stabilizing substitutions.

The HIV-I envelope glycoprotein (Env) is a trimer of heterodimers composed of two non-covalently associated subunits; the receptor-binding gp120, and the fusion machinery-containing gp41. Each subunit is derived from a gp160 precursor glycoprotein following cleavage by cellular furins (Wyatt R & Sodroski J (1998) Science 280(5371):1884-1888). HIV-I gp120 binds the CD4 molecule on the surface of human target T cells to initiate the viral entry process, and following co-receptor engagement, fusion is mediated by gp41 (Dalgleish A G, et al. (1984) Nature 312(5996):763-767; McDougal J S, et al. (1986) J Immunol 137(9):2937-2944; mKarlsson Hedestam G B, et al. (2008) Nat Rev Microbial 6(2):143-155). The surface-exposed HIV-I Env trimer is the sole target for antibodies capable of neutralizing the virus (Burton D R, et al. (2004) Nat Immunol 5(3):233-236). Recently, a myriad of Env-directed broadly neutralizing antibodies (bnAbs) were isolated from numerous HIV-I-infected individuals, demonstrating that the human B cell response can effectively inhibit this variable pathogen (Wu X, et al. (2010) Science 329(5993):856-861; Walker L M, et al. (2009) Science 326(5950):285-289; Walker L M, et al. (2011) Nature 477(7365):466-470; Huang J, et al. (2012) Nature 491(7424):406-412; Scharf L, et al. (2014) Antibody 8ANC195 reveals a site of broad vulnerability on the HIV-I envelope spike. Cell reports 7(3):785-795; Klein F, et al. (2012) J Exp Med 209(8):1469-1479). Infection of macaques by a chimeric model virus, SHIV, can be prevented by prior passive immunization of all bnAbs so far tested, confirming the capacity of neutralizing antibodies to prevent HIV infection (Mascola J R, et al. (1999) J Virol 73(5):4009-4018; Hessell A J, et al. (2009) PLoS Pathog 5(5):e1000433; Moldt B, et al. (2012) Proc Natl Acad Sci USA 109(46):18921-18925; Barouch D H, et al. (2013) Therapeutic efficacy of potent neutralizing HIV-I-specific monoclonal antibodies in SHIV-infected rhesus monkeys. Nature 503(7475):224-228).

Along with virus-specific T cells, an efficacious HIV-I vaccine therefore would likely need to generate bnAbs targeting Env. Although the premise is simple, in actuality, it is a tremendous challenge without precedent in the history of vaccinology. The difficulty to vaccinate against HIV arises from the extensive variability of Env present on the large number of HIV-I isolates simultaneously circulating in the human population as well as other mechanisms of immune evasion selected for by strong pressure from the human immune system.

Generally, vaccine-generated antibodies using either or both gp120 or gp41 sequences do not recognize native Env on the surface of cells or virus, do not neutralize primary isolates in vitro, and do not prevent infection in laboratory animals (Burton D R, et al. (2011) Proc Natl Acad Sci US A 108(27):11181-11186; Sundling C, et al. (2012) Science translational medicine 4(142):142ra196; Tran K, et al. (2014) Vaccine-elicited primate antibodies use a distinct approach to the HIV-I primary receptor binding site informing vaccine redesign. Proc Natl Acad Sci USA 111(7):E738-747). Non-neutralizing antibodies directed to the major variable region two (V2) of gp120 are associated with modest efficacy in a single human clinical trial (Haynes B F, et al. (2012) N Engl J Med 366(14):1275-1286; Zolla-Pazner S, et al. (2014) Vaccine-induced IgG antibodies to VIV2 regions of multiple HIV-I subtypes correlate with decreased risk of HIV-I infection. PLoS One 9(2):e87572), while, in general, Env-elicited antibodies fail to demonstrate protection in previous human clinical trials (Jones N G, et al. (2009) Vaccine 27(7):1136-1140; Rerks-Ngarm S, et al. (2009) N Engl J Med 361(23):2209-2220; Yates N L, et al. (2014) Vaccine-induced Env V1-V2 IgG3 correlates with lower HIV-I infection risk and declines soon after vaccination. Science translational medicine 6(228):228ra239).

Many Env-based trimeric candidate immunogens are engineered to eliminate cleavage between gp120 and gp41 (so called uncleaved gp140 trimers), usually generating imperfect mimetics of the functional spike based on antigenic profiling or EM analysis (Tran K, et al. (2014) Proc Natl Acad Sci USAll 1(7):E738-747; Ringe R P, et al. (2013) Proc Natl Acad Sci USA 110(45):18256-18261). As a group, the defined, or presumed to be, disordered trimers (in adjuvant) generate high self-binding antibody titers. However, these vaccine-elicited antibodies do not efficiently neutralize most HIV-I primary isolates, that is, strains representative of those circulating in the human population (Sundling C, et al. (2012) Science translational medicine 4(142):142ra196; Chakrabarti B K, et al. (2013) J Virol 87(24):13239-13251; Kovacs J M, et al. (2012) Proc Natl Acad Sci US A 109(30):12111-12116; Nkolola J P, et al. (2014) Comparison of multiple adjuvants on the stability and immunogenicity of a clade C HIV-I gp140 trimer. Vaccine 32(18):2109-2116). Antibodies elicited by these immunogens target epitopes exposed only on the free gp120 and trimeric post-fusion forms of gp41 or disordered gp140s and thus are ineffective at accessing their epitopes buried within the ordered, quaternary structure achieved in the native Env spike. Applicants recently described the limitations of two CD4bs-directed non-bnAbs, (GE148 and GE136) generated following immunization of uncleaved gp140 trimers (YU2 gp140-foldon) in non-human primates (NHP). Non-bnAbs, represented by GE136 and 148, can only neutralize the sensitive so-called "tier I viruses" that are not representative of the more neutralization resistant tier 2-like primary isolates circulating in the human population. Using crystallography, EM reconstructions, paratope scanning and molecular modeling, Applicants determined that these vaccine-elicited antibodies fail to reach the CD4bs due to steric barriers imposed by quaternary packing of the native Env on neutralization resistant primary isolates, a property that Applicants use to Applicants' advantage in the negative-selection strategy presented here (Tran K, et al. (2014) Proc Natl Acad Sci USA 111(7):E738-747).

The cumulative historical data have led to the hypothesis that a more faithful mimic of the HIV-I spike that better recapitulates the native, pre-fusion form of Env, selectively displaying neutralizing determinants while occluding non-neutralizing determinants, may better elicit antibodies capable of accessing the native spike. A soluble Env mimetic, containing a disulfide linkage between gp120 and gp41 (SOS), first described in the 2000s, and further developed over the next decade, displays many of these properties, culminating in the determination of the high resolution structures of the well-ordered BG505 SOSIP trimers by crystallography and EM (Lyumkis D, et al. (2013) Science 342(6165):1484-1490; Julien J P, et al. (2013) Science 342(6165):1477-1483; Sanders R W, et al. (2013) PLoS Pathog 9(9):e1003618; Depetris R S, et al. (2012) J Biol Chem 287(29):24239-24254). A sub-nanometer EM reconstruction of KNHI 144 SOSIP is also available but does not provide atomic level details (Bartesaghi A, Merk A, Borgnia M J, Milne J L, & Subramaniam S (2013) Nat Struct Mol Biol 20(12):1352-1357). The BG505 SOSIP and KNHI1144 SOSIP trimers are derived from the Env sequences of the subtype A BG505 and KNHI 144 strains. These soluble trimers possess an engineered disulfide linkage between the gp120 and gp41 (at residues 501C and 605C, respectively) and an additional mutation in the heptad repeat I (HRI) of gp41 (1559P) that facilitates trimerization (Binley J M, et al. (2000) J Virol 74(2):627-643; Sanders R W, et al. (2002) J Virol 76(17):8875-8889). A truncation of the membrane proximal external region (MPER) at residue 664 enhances expression while decreasing aggregation is incorporated into the so-called BG505 SOSIP.664 trimers (Sanders R W, et al. (2013) PLoS Pathog 9(9):e1003618; Sanders R W, et al. (2002) J Virol 76(17):8875-8889). Although SOSIP molecules based on other HIV-I primary strains were attempted over the past decade, the BG505- and KNHI 144-derived SOSIP trimers are the two limited examples of SOSIPs that yield homogeneous trimers suitable for high resolution biophysical and structural analysis. The structural explanation for the difficulty to readily transfer the SOSIP design to other HIV-I strain-derived sequences is not yet fully understood and would be valuable information to broaden the trimer design horizon.

Since the initial soluble native-like BG505 SOPIP.664 Env trimer was confirmed to adopt a near-native conformation by high-resolution structural analysis, multiple efforts to produce stable, soluble Env mimetics derived from multiple HIV-1 strains were pursued [Javiers, sanders]. Multiple solutions to this objective include the improved cleavage-independent NFL trimers, UFOs and modified SOSIPs. Both the SOSIP and NFL well-ordered trimers are efficiently recognized by broadly neutralizing antibodies (bnAbs) which arise sporadically during the course of natural infection. In some cases, including the important advances described here, have been used to isolate such bnAbs. One approach to elicit tier 2 neutralizing Abs has been to immunize the existing well-ordered trimers using prime:boosting in selected animal models. For BG505 and 16055 native-like trimers this approach does elicit tier 2 neutralizing antibodies, but of limited cross-reactive breadth (REFS).

Most cross-conserved sites on the HIV Env spike are occluded by evolved, incorporated self-N-glycans, limiting naïve B cell recognition of the underlying polypeptide surface. The exceptions are the protein surfaces of the primary receptor CD4 binding site (CD4bs) and the furin cleavage site (proximal to the gp120:41 interface). Infrequently, during the course of the natural HIV infection process, bnAbs are elicited to these aforementioned sites of vulnerability. In addition, other bnAbs directed to the V2 apex, the 332N-glycan supersite and to the fusion peptide or the high-mannose patch are elicited during the course of chronic HIV infection (REFS). However, prior to the present invention, rarely, if ever, have such bnAbs been elicited by vaccination of Env formulated with adjuvant.

After decades of development, advances in soluble HIV-1 Env mimics design permits the generation of a diverse array of native-like trimers (Ward and Wilson, 2017. The HIV-1 envelope glycoprotein structure: nailing down a moving target. Immunol Rev 275:21-32; Karlsson et al., 2017. Evolution of B cell analysis and Env trimer redesign. Immunol Rev 275:183-202). The successful development of the soluble SOSIP trimers provided proof-of-principle (Sanders et al, 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618) forming a prefusion native-like conformation (Lyumkis et al., 2013. Cryo-EM structure of a fully glycosylated soluble cleaved HIV-1 envelope trimer. Science 342:1484-1490; Julien et al, 2013. Crystal structure of a soluble cleaved HIV-1 envelope trimer. Science 342:1477-1483; Garces et al., 2015. Affinity Maturation of a Potent Family of HIV Antibodies Is Primarily Focused on Accommodating or Avoiding Glycans. Immunity 43:1053-1063; Pancera et al., 2014. Structure and immune recognition of trimeric pre-fusion HIV-1 Env. Nature 514:455-461). The SOSIP gp140 trimer is proteolytically cleaved by cellular furins to gp120 and gp41 subunits and covalently linked by an engineered intra-protomer disulfide bond A501C-T605C (SOS). These trimers also require mutation (I559P) in the gp41 heptad repeat 1 (HR1) to maintain well-ordered oligomers, as well as expression of exogenous furin for full conformational integrity (Sanders et al., 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618; Guenaga et al., 2015. Well-Ordered Trimeric HIV-1 Subtype B and C Soluble Spike Mimetics Generated by Negative Selection Display Native-like Properties. PLoS Pathog 11:e1004570; Julien et al., 2015. Design and structure of two HIV-1 clade C SOSIP.664 trimers that increase the arsenal of native-like Env immunogens. Proc Natl Acad Sci USA 112:11947-11952; de Taeye et al. 2015. Immunogenicity of Stabilized HIV-1 Envelope Trimers with Reduced Exposure of Non-neutralizing Epitopes. Cell 163:1702-1715; Pugach et al. 2015. A native-like SOSIP.664 trimer based on an HIV-1 subtype B env gene. J Virol 89:3380-3395; Ringe et al. 2013. Cleavage strongly influences whether soluble HIV-1 envelope glycoprotein trimers adopt a native-like conformation. Proc Natl Acad Sci USA 110:18256-18261; Ringe et al. 2015. Influences on the Design and Purification of Soluble, Recombinant Native-Like HIV-1 Envelope Glycoprotein Trimers. J Virol 89:12189-12210; Ringe et al. 2017. Reducing V3 Antigenicity and Immunogenicity on Soluble, Native-Like HIV-1 Env SOSIP Trimers. J Virol 91; Ahmed et al. 2017. Stabilization of a soluble, native-like trimeric form of an efficiently cleaved Indian HIV-1 clade C envelope glycoprotein. J Biol Chem 292:8236-8243; Sanders et al. 2002. Stabilization of the soluble, cleaved, trimeric form of the envelope glycoprotein complex of human immunodeficiency virus type 1. J Virol 76:8875-8889; Binley et al. 2000. A recombinant human immunodeficiency virus type 1 envelope glycoprotein complex stabilized by an intermolecular disulfide bond between the gp120 and gp41 subunits is an antigenic mimic of the trimeric virion-associated structure. J Virol 74:627-643). In the past years, Applicants developed an improved native-like trimer design, generating well-ordered soluble Env mimics that are fully cleavage-independent, termed native flexibly linked (NFL) trimers. This design uses a flexible linker (two copies of Gly4-Ser, "G45") to replace the natural cleavage site and sequence (Sharma et al. 2015. Cleavage-independent HIV-1 Env trimers engineered as soluble native spike mimetics for vaccine design. Cell Rep 11:539-550). The flexible linker between the natural C-terminus of gp120 and N-terminus of gp41, allows the un-cleaved trimers to achieve a native-like conformation without the need of furin for precursor processing. However, the original NFL trimer design contains the I559P mutation (Sharma et al. 2015. Cleavage-independent HIV-1 Env trimers engineered as soluble native spike mimetics for vaccine design. Cell Rep 11:539-550) that was initially identified in the SOSIP context to disfavor the post fusion state (Sanders et al. 2013. A next-generation cleaved, soluble HIV-1 Env trimer, BG505 SOSIP.664 gp140, expresses multiple epitopes for broadly neutralizing but not non-neutralizing antibodies. PLoS Pathog 9:e1003618). Both the original SOSIP and NFL designs do not form a high percentage of well-ordered trimers in all Env contexts. In the original NFL design, it is relatively inefficient in generating high yields of trimers derived from clade C strains, such as 16055 (Guenaga et al. 2015. Structure-Guided Redesign Increases the Propensity of HIV Env To Generate Highly Stable Soluble Trimers. J Virol 90:2806-2817). To improve trimer design, Applicants incorporated residues from BG505 (called trimer-derived (TD) residues) into 16055 NFLs, substantially improving the propensity to form native-like trimers (Guenaga et al. 2015. Structure-Guided Redesign Increases the Propensity of HIV Env To Generate Highly Stable Soluble Trimers. J Virol 90:2806-2817) and the elicitation of tier 2 clade C neutralizing antibodies (Martinez-Murillo et al., GB. 2017. Particulate Array of Well-Ordered HIV Clade C Env Trimers Elicits Neutralizing Antibodies that Display a Unique V2 Cap Approach. Immunity 46:804-817 e807; Dubrovskaya et al. 2017. Targeted N-glycan deletion at the receptor-binding site retains HIV Env NFL trimer integrity and accelerates the elicited antibody response. PLoS Pathog 13:e1006614). Further improvements on the TD design by targeted glycine substitutions at helix-to-coil transitions that disfavor the post-fusion state of Env (TD CC+, namely "TD+"), significantly improve trimer homogeneity, yield, stability and antigenicity, resulting in the first high-resolution clade C Env structure (Guenaga et al. 2017. Glycine Substitution at Helix-to-Coil Transitions Facilitates the Structural Determination of a Stabilized Subtype C HIV Envelope Glycoprotein. Immunity 46:792-803 e793).

Applicants believe that the glycine changes may lower the activation potential of the gp41 (and Env) to change conformation, and therefore results in better behaved trimers in a lower energy well from the "activation state" to spring to the next conformation. In a simple model, gp41 is essentially spring-loaded and constrained by gp120 until receptor binding. These mutations may contribute to reducing the springiness.

Assays for screening for neutralizing antibodies are known in the art. A neutralization assay approach has been described previously (Binley J M, et al., (2004). Comprehensive Cross-Clade Neutralization Analysis of a Panel of Anti-Human Immunodeficiency Virus Type 1 Monoclonal Antibodies. J Viral. 78: 13232-13252). Pseudotyped viruses may be generated by co-transfecting cells with at least two plasmids encoding the soluble Env cDNA of the present invention and the rest of the HIV genome separately. In the HIV genome encoding vector, the Env gene may be replaced by the firefly luciferase gene. Transfectant supernatants containing pseudotyped virus may be co-incubated overnight with B cell supernatants derived from activation of an infected donor's primary peripheral blood mononuclear cells (PBMCs). Cells stably transfected with and expressing CD4 plus the CCR5 and CXCR4 coreceptors may be added to the mixture and incubated for 3 days at 37° C. Infected cells may be quantified by luminometry.

In another embodiment of the present invention, the soluble envelope glycoproteins of the present invention may be crystallized in combination with any neutralizing antibodies, including those identified by the above methods, to determine the exact molecular surface where the soluble envelope glycoprotein binds with the neutralizing antibody to design HIV-I immunogens.

It is to be understood that this invention is not limited to particular methods, components, products or combinations described, as such methods, components, products and combinations may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of", as well as the terms "consisting essentially of, "consists essentially" and "consists essentially of. It is noted that in this disclosure and particularly in the claims and/or paragraphs, terms such as "comprises", "comprised", "comprising" and the like can have the meaning attributed to it in U. S. Patent law; e.g., they can mean "includes", "included", "including", and the like; and that terms such as "consisting essentially of and "consists essentially of have the meaning ascribed to them in U. S. Patent law, e.g., they allow for elements not explicitly recited, but exclude elements that are found in the prior art or that affect a basic or novel characteristic of the invention. It may be advantageous in the practice of the invention to be in compliance with Art. 53(c) EPC and Rule 28(b) and (c) EPC. Nothing herein is intended as a promise.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−20% or less, preferably +/−10% or less, more preferably +1-5% or less, and still more preferably +/−1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one" or "X or more", where X is a number and understand to mean X or increases one by one of X, such as one or more or at least one member(s) or "X or more" of a group of members, is clear per se, by means of further exemplification, the term encompasses inter alia a reference to any one of said members, or to any two or more of said members, such as, e.g., any >3, >4, >5, >6 or >7 etc. of said members, and up to all said members.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Standard reference works setting forth the general principles of recombinant DNA technology include Molecular Cloning: A Laboratory Manual, 2nd ed., vol. 1-3, ed. Sambrook et al., Cold Spring Harbor Laboratory Press, Cold Spring Harbor, N.Y., 1989; Current Protocols in Molecular Biology, ed. Ausubel et al., Greene Publishing and Wiley-Interscience, New York, 1992 (with periodic updates) ("Ausubel et al. 1992"); the series Methods in Enzymology (Academic Press, Inc.); Innis et al., PCR Protocols: A Guide to Methods and Applications, Academic Press: San Diego, 1990; PCR 2: A Practical Approach (M. J. MacPherson, B. D. Hames and G. R. Taylor eds. (1995); Harlow and Lane, eds. (1988) Antibodies, a Laboratory Manual; and Animal Cell Culture (R. I. Freshney, ed. (1987). General principles of microbiology are set forth, for example, in Davis, B. D. et al., Microbiology, 3rd edition, Harper & Row, publishers, Philadelphia, Pa. (1980).

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

In this description of the invention, reference is made to the accompanying drawings that form a part hereof, and in which are shown by way of illustration only of specific embodiments in which the invention may be practiced. It is to be understood that other embodiments may be utilized and structural or logical changes may be made without departing from the scope of the present invention. The description, therefore, is not to be taken in a limiting sense, and the scope of the present invention is defined by the appended claims.

Preferred statements (features) and embodiments of this invention are set herein below. Each statements and embodiments of the invention so defined may be combined with any other statement and/or embodiments unless clearly indicated to the contrary. In particular, any feature indicated as being preferred or advantageous may be combined with any other feature or features or statements indicated as being preferred or advantageous.

Unless specifically stated or obvious from context, as used herein, the term "about" is understood as within a range of normal tolerance in the art, for example within 2 standard deviations of the mean. About can be understood as within 50%, 45%, 40%, 35%, 30%, 25%, 20%, 15%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

Unless specifically stated or obvious from context, as used herein, the term "or" is understood to be inclusive. Unless specifically stated or obvious from context, as used herein, the terms "a," "an," and "the" are understood to be singular or plural.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, F(ab') 2, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

F(ab')2, the fragment of the antibody that can be obtained by treating whole antibody with the enzyme pepsin without subsequent reduction; F(ab')2 is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-I virus F with a neutralization index >1.5 or >2.0. Broad and potent neutralizing antibodies may neutralize greater than about 50% of HIV-I viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies and/or antigens of the invention may differ from the exact sequences illustrated and described herein. Thus, the invention contemplates deletions, additions and substitutions to the sequences shown, so long as the sequences function in accordance with the methods of the invention. In this regard, particularly preferred substitutions may generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, praline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antigens of the invention and can be designed to employ codons that are used in the genes of the subject in which the antigen is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the transgenic HIV proteins in human cells. Any suitable method of codon optimization may be used. Such methods, and the selection of such methods, are well known to those of skill in the art. In addition, there are several companies that will optimize codons of sequences, such as Genart. Thus, the nucleotide sequences of the invention can readily be codon optimized.

The invention further encompasses nucleotide sequences encoding functionally and/or antigenically equivalent variants and derivatives of the antigens of the invention and functionally equivalent fragments thereof. These functionally equivalent variants, derivatives, and fragments display the ability to retain antigenic activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448. Advantageous for use according to the present invention is the WU-BLAST (Washington University BLAST) version 2.0 software. WU-BLAST version 2.0 executable programs for several UNIX platforms can be downloaded from the Washington University BLAST website. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies and/or antigens of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies and/or antigens of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies and/or antigens be expressed in vivo, for example when the transgenes of the invention are used in DNA or DNA-containing vaccines, any vector that allows for the expression of the antibodies and/or antigens of the present invention and is safe for use in vivo may be used. In preferred embodiments the vectors used are safe for use in humans, mammals and/or laboratory animals.

For the antibodies and/or antigens of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, *intrans*, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The present invention relates to a recombinant vector expressing a foreign epitope. Advantageously, the epitope is an SIV or HIV epitope or combination thereof. In an advantageous embodiment, the SIV or HIV epitope is a soluble envelope glycoprotein, however, the present invention may encompass additional HIV antigens, epitopes or immunogens. Advantageously, the additional epitope is an HIV antigen, HIV epitope or an HIV immunogen, such as, but not limited to, the HIV antigens, HIV epitopes or HIV immunogens of U.S. Pat. Nos. 7,341,731; 7,335,364; 7,329, 807; 7,323,553; 7,320,859; 7,311,920; 7,306,798; 7,285, 646; 7,285,289; 7,285,271; 7,282,364; 7,273,695; 7,270, 997; 7,262,270; 7,244,819; 7,244,575; 7,232,567; 7,232, 566; 7,223,844; 7,223,739; 7,223,534; 7,223,368; 7,220, 554; 7,214,530; 7,211,659; 7,211,432; 7,205,159; 7,198, 934; 7,195,768; 7,192,555; 7,189,826; 7,189,522; 7,186, 507; 7,179,645; 7,175,843; 7,172,761; 7,169,550; 7,157, 083; 7,153,509; 7,147,862; 7,141,550; 7,129,219; 7,122, 188; 7,118,859; 7,118,855; 7,118,751; 7,118,742; 7,105, 655; 7,101,552; 7,097,971; 7,097,842; 7,094,405; 7,091, 049; 7,090,648; 7,087,377; 7,083,787; 7,070,787; 7,070, 781; 7,060,273; 7,056,521; 7,056,519; 7,049,136; 7,048, 929; 7,033,593; 7,030,094; 7,022,326; 7,009,037; 7,008, 622; 7,001,759; 6,997,863; 6,995,008; 6,979,535; 6,974, 574; 6,972,126; 6,969,609; 6,964,769; 6,964,762; 6,958,
158; 6,956,059; 6,953,689; 6,951,648; 6,946,075; 6,927,
031; 6,919,319; 6,919,318; 6,919,077; 6,913,752; 6,911,
315; 6,908,617; 6,908,612; 6,902,743; 6,900,010; 6,893,
869; 6,884,785; 6,884,435; 6,875,435; 6,867,005; 6,861,
234; 6,855,539; 6,841,381 6,841,345; 6,838,477; 6,821,955;
6,818,392; 6,818,222; 6,815,217; 6,815,201; 6,812,026;
6,812,025; 6,812,024; 6,808,923; 6,806,055; 6,803,231;
6,800,613; 6,800,288; 6,797,811; 6,780,967; 6,780,598;
6,773,920; 6,764,682; 6,761,893; 6,753,015; 6,750,005;
6,737,239; 6,737,067; 6,730,304; 6,720,310; 6,716,823;
6,713,301; 6,713,070; 6,706,859; 6,699,722; 6,699,656;
6,696,291; 6,692,745; 6,670,181; 6,670,115; 6,664,406;
6,657,055; 6,657,050; 6,656,471; 6,653,066; 6,649,409;
6,649,372; 6,645,732; 6,641,816; 6,635,469; 6,613,530;
6,605,427; 6,602,709; 6,602,705; 6,600,023; 6,596,477;
6,596,172; 6,593,103; 6,593,079; 6,579,673; 6,576,758;
6,573,245; 6,573,040; 6,569,418; 6,569,340; 6,562,800;
6,558,961; 6,551,828; 6,551,824; 6,548,275; 6,544,780;
6,544,752; 6,544,728; 6,534,482; 6,534,312; 6,534,064;
6,531,572; 6,531,313; 6,525,179; 6,525,028; 6,524,582;
6,521,449; 6,518,030; 6,518,015; 6,514,691; 6,514,503;
6,511,845; 6,511,812; 6,511,801; 6,509,313; 6,506,384;
6,503,882; 6,495,676; 6,495,526; 6,495,347; 6,492,123;
6,489,131; 6,489,129; 6,482,614; 6,479,286; 6,479,284;
6,465,634; 6,461,615; 6,458,560; 6,458,527; 6,458,370;
6,451,601; 6,451,592; 6,451,323; 6,436,407; 6,432,633;
6,428,970; 6,428,952; 6,428,790; 6,420,139; 6,416,997;
6,410,318; 6,410,028; 6,410,014; 6,407,221; 6,406,710;
6,403,092; 6,399,295; 6,392,013; 6,391,657; 6,384,198;
6,380,170; 6,376,170; 6,372,426; 6,365,187; 6,358,739;
6,355,248; 6,355,247; 6,348,450; 6,342,372; 6,342,228;
6,338,952; 6,337,179; 6,335,183; 6,335,017; 6,331,404;
6,329,202; 6,329,173; 6,328,976; 6,322,964; 6,319,666;
6,319,665; 6,319,500; 6,319,494; 6,316,205; 6,316,003;
6,309,633; 6,306,625; 6,296,807; 6,294,322; 6,291,239;
6,291,157; 6,287,568; 6,284,456; 6,284,194; 6,274,337;
6,270,956; 6,270,769; 6,268,484; 6,265,562; 6,265,149;
6,262,029; 6,261,762; 6,261,571; 6,261,569; 6,258,599;
6,258,358; 6,248,332; 6,245,331; 6,242,461; 6,241,986;
6,235,526; 6,235,466; 6,232,120; 6,228,361; 6,221,579;
6,214,862; 6,214,804; 6,210,963; 6,210,873; 6,207,185;
6,203,974; 6,197,755; 6,197,531; 6,197,496; 6,194,142;
6,190,871; 6,190,666; 6,168,923; 6,156,302; 6,153,408;
6,153,393; 6,153,392; 6,153,378; 6,153,377; 6,146,635;
6,146,614; 6,143,876 6,140,059; 6,140,043; 6,139,746;
6,132,992; 6,124,306; 6,124,132; 6,121,006; 6,120,990;
6,114,507; 6,114,143; 6,110,466; 6,107,020; 6,103,521;
6,100,234; 6,099,848; 6,099,847; 6,096,291; 6,093,405;
6,090,392; 6,087,476; 6,083,903; 6,080,846; 6,080,725;
6,074,650; 6,074,646; 6,070,126; 6,063,905; 6,063,564;
6,060,256; 6,060,064; 6,048,530; 6,045,788; 6,043,347;
6,043,248; 6,042,831; 6,037,165; 6,033,672; 6,030,772;
6,030,770; 6,030,618; 6,025,141; 6,025,125; 6,020,468;
6,019,979; 6,017,543; 6,017,537; 6,015,694; 6,015,661;
6,013,484; 6,013,432; 6,007,838; 6,004,811; 6,004,807;
6,004,763; 5,998,132; 5,993,819; 5,989,806; 5,985,926;
5,985,641; 5,985,545; 5,981,537; 5,981,505; 5,981,170;
5,976,551; 5,972,339; 5,965,371; 5,962,428; 5,962,318;
5,961,979; 5,961,970; 5,958,765; 5,958,422; 5,955,647;
5,955,342; 5,951,986; 5,951,975; 5,942,237; 5,939,277;
5,939,074; 5,935,580; 5,928,930; 5,928,913; 5,928,644;
5,928,642; 5,925,513; 5,922,550; 5,922,325; 5,919,458;
5,916,806; 5,916,563; 5,914,395; 5,914,109; 5,912,338;
5,912,176; 5,912,170; 5,906,936; 5,895,650; 5,891,623;
5,888,726; 5,885,580 5,885,578; 5,879,685; 5,876,731;
5,876,716; 5,874,226; 5,872,012; 5,871,747; 5,869,058;

5,866,694; 5,866,341; 5,866,320; 5,866,319; 5,866,137;
5,861,290; 5,858,740; 5,858,647; 5,858,646; 5,858,369;
5,858,368; 5,858,366; 5,856,185; 5,854,400; 5,853,736;
5,853,725; 5,853,724; 5,852,186; 5,851,829; 5,851,529;
5,849,475; 5,849,288; 5,843,728; 5,843,723; 5,843,640;
5,843,635; 5,840,480; 5,837,510; 5,837,250; 5,837,242;
5,834,599; 5,834,441; 5,834,429; 5,834,256; 5,830,876;
5,830,641; 5,830,475; 5,830,458; 5,830,457; 5,827,749;
5,827,723; 5,824,497; 5,824,304; 5,821,047; 5,817,767;
5,817,754; 5,817,637; 5,817,470; 5,817,318; 5,814,482;
5,807,707; 5,804,604; 5,804,371; 5,800,822; 5,795,955;
5,795,743; 5,795,572; 5,789,388; 5,780,279; 5,780,038;
5,776,703; 5,773,260; 5,770,572; 5,766,844; 5,766,842;
5,766,625; 5,763,574; 5,763,190; 5,762,965; 5,759,769;
5,756,666; 5,753,258; 5,750,373; 5,747,641; 5,747,526;
5,747,028; 5,736,320; 5,736,146; 5,733,760; 5,731,189;
5,728,385; 5,721,095; 5,716,826; 5,716,637; 5,716,613;
5,714,374; 5,709,879; 5,709,860; 5,709,843; 5,705,331;
5,703,057; 5,702,707; 5,698,178; 5,688,914; 5,686,078;
5,681,831; 5,679,784; 5,674,984; 5,672,472; 5,667,964;
5,667,783; 5,665,536; 5,665,355; 5,660,990; 5,658,745;
5,658,569; 5,643,756; 5,641,624; 5,639,854; 5,639,598;
5,637,677; 5,637,455; 5,633,234; 5,629,153; 5,627,025;
5,622,705; 5,614,413; 5,610,035; 5,607,831; 5,606,026;
5,601,819; 5,597,688; 5,593,972; 5,591,829; 5,591,823;
5,589,466; 5,587,285; 5,585,254; 5,585,250; 5,580,773;
5,580,739; 5,580,563; 5,573,916; 5,571,667; 5,569,468;
5,558,865; 5,556,745; 5,550,052; 5,543,328; 5,541,100;
5,541,057; 5,534,406; 5,529,765; 5,523,232; 5,516,895;
5,514,541; 5,510,264; 5,500,161; 5,480,967; 5,480,966;
5,470,701; 5,468,606; 5,462,852; 5,459,127; 5,449,601;
5,447,838; 5,447,837; 5,439,809; 5,439,792; 5,418,136;
5,399,501; 5,397,695; 5,391,479; 5,384,240; 5,374,519;
5,374,518; 5,374,516; 5,364,933; 5,359,046; 5,356,772;
5,354,654; 5,344,755; 5,335,673; 5,332,567; 5,320,940;
5,317,009; 5,312,902; 5,304,466; 5,296,347; 5,286,852;
5,268,265; 5,264,356; 5,264,342; 5,260,308; 5,256,767;
5,256,561; 5,252,556; 5,230,998; 5,230,887; 5,227,159;
5,225,347; 5,221,610 5,217,861; 5,208,321; 5,206,136;
5,198,346; 5,185,147; 5,178,865; 5,173,400; 5,173,399;
5,166,050; 5,156,951; 5,135,864; 5,122,446; 5,120,662;
5,103,836; 5,100,777; 5,100,662; 5,093,230; 5,077,284;
5,070,010; 5,068,174; 5,066,782; 5,055,391; 5,043,262;
5,039,604; 5,039,522; 5,030,718; 5,030,555; 5,030,449;
5,019,387; 5,013,556; 5,008,183; 5,004,697; 4,997,772;
4,983,529; 4,983,387; 4,965,069; 4,945,082; 4,921,787;
4,918,166; 4,900,548; 4,888,290; 4,886,742; 4,885,235;
4,870,003; 4,869,903; 4,861,707; 4,853,326; 4,839,288;
4,833,072 and 4,795,739.

In another embodiment, HIV, or immunogenic fragments thereof, may be utilized as the HIV epitope. For example, the HIV nucleotides of U.S. Pat. Nos. 7,393,949, 7,374,877, 7,306,901, 7,303,754, 7,173,014, 7,122,180, 7,078,516, 7,022,814, 6,974,866, 6,958,211, 6,949,337, 6,946,254, 6,896,900, 6,887,977, 6,870,045, 6,803,187, 6,794,129, 6,773,915, 6,768,004, 6,706,268, 6,696,291, 6,692,955, 6,656,706, 6,649,409, 6,627,442, 6,610,476, 6,602,705, 6,582,920, 6,557,296, 6,531,587, 6,531,137, 6,500,623, 6,448,078, 6,429,306, 6,420,545, 6,410,013, 6,407,077, 6,395,891, 6,355,789, 6,335,158, 6,323,185, 6,316,183, 6,303,293, 6,300,056, 6,277,561, 6,270,975, 6,261,564, 6,225,045, 6,222,024, 6,194,391, 6,194,142, 6,162,631, 6,114,167, 6,114,109, 6,090,392, 6,060,587, 6,057,102, 6,054,565, 6,043,081, 6,037,165, 6,034,233, 6,033,902, 6,030,769, 6,020,123, 6,015,661, 6,010,895, 6,001,555, 5,985,661, 5,980,900, 5,972,596, 5,939,538, 5,912,338, 5,869,339, 5,866,701, 5,866,694, 5,866,320, 5,866,137, 5,864,027, 5,861,242, 5,858,785, 5,858,651, 5,849,475, 5,843,638, 5,840,480, 5,821,046, 5,801,056, 5,786,177, 5,786,145, 5,773,247, 5,770,703, 5,756,674, 5,741,706, 5,705,612, 5,693,752, 5,688,637, 5,688,511, 5,684,147, 5,665,577, 5,585,263, 5,578,715, 5,571,712, 5,567,603, 5,554,528, 5,545,726, 5,527,895, 5,527,894, 5,223,423, 5,204,259, 5,144,019, 5,051,496 and 4,942,122 are useful for the present invention.

Any epitope recognized by an HIV antibody may be used in the present invention. For example, the anti-HIV antibodies of U.S. Pat. Nos. 6,984,721, 6,972,126, 6,949,337, 6,946,465, 6,919,077, 6,916,475, 6,911,315, 6,905,680, 6,900,010, 6,825,217, 6,824,975, 6,818,392, 6,815,201, 6,812,026, 6,812,024, 6,797,811, 6,768,004, 6,703,019, 6,689,118, 6,657,050, 6,608,179, 6,600,023, 6,596,497, 6,589,748, 6,569,143, 6,548,275, 6,525,179, 6,524,582, 6,506,384, 6,498,006, 6,489,131, 6,465,173, 6,461,612, 6,458,933, 6,432,633, 6,410,318, 6,406,701, 6,395,275, 6,391,657, 6,391,635, 6,384,198, 6,376,170, 6,372,217, 6,344,545, 6,337,181, 6,329,202, 6,319,665, 6,319,500, 6,316,003, 6,312,931, 6,309,880, 6,296,807, 6,291,239, 6,261,558, 6,248,514, 6,245,331, 6,242,197, 6,241,986, 6,228,361, 6,221,580, 6,190,871, 6,177,253, 6,146,635, 6,146,627, 6,146,614, 6,143,876, 6,132,992, 6,124,132, RE36,866, 6,114,143, 6,103,238, 6,060,254, 6,039,684, 6,030,772, 6,020,468, 6,013,484, 6,008,044, 5,998,132, 5,994,515, 5,993,812, 5,985,545, 5,981,278, 5,958,765, 5,939,277, 5,928,930, 5,922,325, 5,919,457, 5,916,806, 5,914,109, 5,911,989, 5,906,936, 5,889,158, 5,876,716, 5,874,226, 5,872,012, 5,871,732, 5,866,694, 5,854,400, 5,849,583, 5,849,288, 5,840,480, 5,840,305, 5,834,599, 5,831,034, 5,827,723, 5,821,047, 5,817,767, 5,817,458, 5,804,440, 5,795,572, 5,783,670, 5,776,703, 5,773,225, 5,766,944, 5,753,503, 5,750,373, 5,747,641, 5,736,341, 5,731,189, 5,707,814, 5,702,707, 5,698,178, 5,695,927, 5,665,536, 5,658,745, 5,652,138, 5,645,836, 5,635,345, 5,618,922, 5,610,035, 5,607,847, 5,604,092, 5,601,819, 5,597,896, 5,597,688, 5,591,829, 5,558,865, 5,514,541, 5,510,264, 5,478,753, 5,374,518, 5,374,516, 5,344,755, 5,332,567, 5,300,433, 5,296,347, 5,286,852, 5,264,221, 5,260,308, 5,256,561, 5,254,457, 5,230,998, 5,227,159, 5,223,408, 5,217,895, 5,180,660, 5,173,399, 5,169,752, 5,166,050, 5,156,951, 5,140,105, 5,135,864, 5,120,640, 5,108,904, 5,104,790, 5,049,389, 5,030,718, 5,030,555, 5,004,697, 4,983,529, 4,888,290, 4,886,742 and 4,853,326, are also useful for the present invention.

Methods for the chemical conjugation of polypeptides, carbohydrates, and/or lipids are well known in the art (see, for example, Hermanson. Bioconjugate Techniques (Academic Press; 1992); Aslam and Dent, eds. Bioconjugation: Protein coupling Techniques for the Biomedical Sciences (MacMillan: 1998); and Wong Chemistry of Protein Conjugation and Cross-linking (CRC Press: 1991)). For instance, primary amino groups may be incorporated by reaction with ethylenediamine in the presence of sodium cyanoborohydride and sulfhydryls may be introduced by reaction of cysteamin dihydrochloride followed by reduction with a standard disulfide reducing agent. Heterobifunctional crosslinkers, such as, for example, sulfosuccinimidyl (4-iodoacetyl) aminobenzoate, which link the epsilon amino group on the D-lysine residues of copolymers of D-lysine and D-glutamate to a sulfhydryl side chain from an amino terminal cysteine residue on the peptide to be coupled, may be used as well. Chemical conjugation also includes anything covalently bonded directly via side chain bonds or via a linker or spacer group.

In addition to the polyvalent nanoparticle contructs, e.g., ferritin based and LS based constructs, in certain embodiments, nanoparticle formulations may comprise carbohydrate nanoparticles, as a non-limiting example, the carbohydrate carrier may include, but is not limited to, an anhydride-modified phytoglycogen or glycogen-type material, phtoglycogen octenyl succinate, phytoglycogen beta-dextrin, anhydride-modified phytoglycogen beta-dextrin. (See e.g., International Publication No. WO2012109121; herein incorporated by reference in its entirety).

Lipid nanoparticle formulations may be improved by replacing the cationic lipid with a biodegradable cationic lipid which is known as a rapidly eliminated lipid nanoparticle (reLNP). Ionizable cationic lipids, such as, but not limited to, DLinDMA, DLin-KC2-DMA, and DLin-MC3-DMA, have been shown to accumulate in plasma and tissues over time and may be a potential source of toxicity. The rapid metabolism of the rapidly eliminated lipids can improve the tolerability and therapeutic index of the lipid nanoparticles by an order of magnitude from a 1 mg/kg dose to a 10 mg/kg dose in rat. Inclusion of an enzymatically degraded ester linkage can improve the degradation and metabolism profile of the cationic component, while still maintaining the activity of the reLNP formulation. The ester linkage can be internally located within the lipid chain or it may be terminally located at the terminal end of the lipid chain. The internal ester linkage may replace any carbon in the lipid chain.

The average diameter of the nanoparticle employed in the compositions of the invention can be at least one member selected from the group consisting of about 5 nanometers, about 10 nanometers, about 20 nanometers, about 25 nanometers, about 30 nanometers, about 40 nanometers, about 50 nanometers, about 75 nanometers, about 100 nanometers, about 125 nanometers, about 150 nanometers, about 175 nanometers and about 200 nanometers. In another embodiment, the average diameter of the particle is at least one member selected from the group consisting of between about 10 to about 200 nanometers, between about 0.5 to about 5 microns and between about 5 to about 10 microns. In another embodiment, the average diameter of the microparticle is selected from the group consisting of about 0.1 μm, about 0.2 μm, about 0.4 μm, about 0.5 μm, about 1 μm and about 2 μm.

Nanoparticles for use in the compositions of the invention can be made from lipids or other fatty acids (see, for example, U.S. Pat. Nos. 5,709,879; 6,342,226; 6,090,406; Lian, et al., J. of Pharma. Sci. 90:667-680 (2001) and van Slooten, et al., Pharm Res. 17:42-48 (2000)) and non-lipid compositions (see, for example, Kreuter, J. Anat. 189:503-505 (1996), the teachings of all of which are hereby incorporated by reference in their entirety). The compositions can be bilayer or multilamellar liposomes and phospholipid based. Polymerized nanoparticles, as described, for example, in U.S. Pat. No. 7,285,289, the teachings of which are incorporated by reference in their entirety.

Metallic oxide nanoparticles for use in the compositions of the invention can be chemically substituted with at least one reactive moiety capable of forming a thioether bond employing conventionally techniques as described herein and in U.S. Pat. No. 6,086,881, the teachings of which are hereby incorporated by reference in their entirety. The antigen described herein can be coupled in a single step onto the metallic oxide particles by the formation of at least one thioether bond or it may be synthesized or assembled stepwise onto the metallic oxide particles after the initial thioether bond formation. The chemical derivatization reagents for the metallic oxide particles can include organosilane reagents that provide thioalkane functionality or other groups that may readily be converted into thiols or thiol-reactive moieties. Organosilane reagents which may be utilized for this purpose may be, but are not limited to, 3-mercaptopropyltrimethoxysilane, 3-aminopropyltriethoxysilane, 3-iodopropyltrimethoxysilane, 2-chloroethyltrichlorosilane, 3-glycidoxypropyltrimethoxysilane, vinyltrichlorosilane and 3-acryloxypropyltrimethoxysilane. Moieties that include one or more disulfide components may also be joined to the metallic oxide particle surface and thereby provide the corresponding reactive moiety able to enter into and form a thioether bond and juncture. Exemplary nanoparticles for use in the compositions of the invention include at least one member selected from the group consisting of poly (d,1-lactide-co-glycolide, also referred to as "poly(lactic-co-glycolic acid) and bisacyloxypropyl cysteine.

Nanoparticles for use in the compositions of the invention can be made of inorganic material. Nanoparticles for use in the compositions of the invention can be made of a polymer material, such as at least one member selected from the group consisting of polystyrene, brominated polystyrene, polyacrylic acid, polyacrylonitrile, polyamide, polyacryl amide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzyl chloride, polyvinyltoluene, polyvinylidene chloride, polydivinylbenzene, polymethylmethacrylate, polylactide, polyglycolide, poly(lactide-co-glycolide), polyanhydride, polyorthoester, polyphosphazene, polyphosophaze, a carbohydrate, carboxymethyl cellulose, hydroxyethyl cellulose, agar, gel, proteinaceous polymer, polypeptide, eukaryotic and prokaryotic cells, viruses, lipid, metal, resin, latex, rubber, silicone (e.g., polydimethyldiphenyl siloxane), glass, ceramic, charcoal, kaolinite and bentonite.

It is noted that these therapeutics may be a chemical compound, a composition which may comprise a polypeptide of the present invention and/or antibody elicited by such a chemical compound and/or portion thereof or a pharmaceutically acceptable salt or a composition which may comprise a polypeptide of the invention, and may be administered alone or as an active ingredient in combination with pharmaceutically acceptable carriers, diluents, and vehicles, as well as other active ingredients.

The compounds or compositions may be administered orally, subcutaneously or parenterally including intravenous, intraarterial, intramuscular, intraperitoneally, and intranasal administration as well as intrathecal and infusion techniques.

The vectors used in accordance with the present invention should typically be chosen such that they contain a suitable gene regulatory region, such as a promoter or enhancer, such that the antigens and/or antibodies of the invention can be expressed.

For example, when the aim is to express the antibodies and/or antigens of the invention in vitro, or in cultured cells, or in any prokaryotic or eukaryotic system for the purpose of producing the protein(s) encoded by that antibody and/or antigen, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies and/or antigens under the identified circumstances.

When the aim is to express the antibodies and/or antigens of the invention in vivo in a subject, for example in order to generate an immune response against an HIV-I antigen and/or protective immunity against HIV-I, expression vectors that are suitable for expression on that subject, and that are safe for use in vivo, should be chosen. For example, in some embodiments it may be desired to express the antibodies and/or antigens of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-I566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-I antigens in cells in order to produce and isolate the expressed proteins, such as from cells grown in culture. For expressing the antibodies and/or antigens in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies and/or antigens can be carried out in any suitable type of host cells, such as bacterial cells, yeast, insect cells, and mammalian cells. The antibodies and/or antigens of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

A synthetic mutant trimer may be chemically synthesized in whole or part using techniques that are well-known in the art (see, e.g., Kochendoerfer, G. G., 2001). Additionally, homologs and derivatives of the polypeptide may be also be synthesized.

Alternatively, methods which are well known to those skilled in the art may be used to construct expression vectors containing nucleic acid molecules that encode the polypeptide or homologs or derivatives thereof under appropriate transcriptional/translational control signals, for expression. These methods include in vitro recombinant DNA techniques, synthetic techniques and in vivo recombination/genetic recombination. See, for example, the techniques described in Maniatis et al., 1989.

The HIV envelope protein (Env) is the target of broadly neutralizing antibodies (bnAbs) in natural infection. Env is a membrane protein composed of a trimer of gp120 and gp41 subunits that contains a high degree of sequence diversity and a surface that is shielded by N-linked glycans. The bnAbs that target Env often have unusual features such as a long complementarity-determining region (CDR) H3, high levels of somatic hypermutation (SHM), and insertions and deletions (INDELS). Furthermore, most of the bnAbs recognize complex epitopes that are typically non-linear and have both protein and glycan components.

The most common epitope of bnAbs in HIV infected individuals is a high mannose glycan patch at the base of the variable loop V3 that includes a glycan linked to N332 (Landais et al. 2016 PLoS Pathog. 12, e1005369). PGT121 and its somatic relatives are an exceptionally potent family of bnAbs that target this epitope and PGT121 has been shown to protect macaques in SHIV challenge studies (Walker et al. 2011 Nature. 477, 466-470, Moldt et al. 2012 Proc Natl Acad Sci. 109, 18921-18925). The elicitation of high and sustained titers of PGT121-like antibodies by vaccination would therefore have a reasonable likelihood of providing protection against HIV in humans.

In preferred embodiments, the nucleotide sequences, antibodies and/or antigens of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-I immunogenic compositions and vaccines of the invention. In other embodiments, it will be desirable to express the antibodies and/or antigens of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies and/or antigens of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies and/or antigens of the invention to a subject, such as a human, such that the antibodies and/or antigens are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., $Zn$— protein complexes); and/or non-ionic surfactants such as TWEEN™, PLURONICS™ or polyethylene glycol An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri(caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, CA). (PEG).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., AlK(SO4)2, AlNa (SO4)2, AlNH(SO4)2, silica, alum, Al(OH)3, Ca3(PO4)2, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC3 1; see Schellack, C. et al (2003) Proceedings of the 34th Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D fromMycobacterium tuberculosis, substances found in Cornyebacterium *parvum, Bordetella pertussis*, or members of the genus *Brucella*), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-0-acylated monophosphoryl lipid A (3D-MPL), imiquimod (also known in the art as IQM and commercially available as Aldara®; U.S. Pat. Nos. 4,689,338; 5,238,944; Zuber, A K. et al (2004) 22(13-14): 1791-8), and the CCR5 inhibitor CMPD167 (see Veazey, R S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or a-galactosyl ceramide; see Green, T. D. et al, (2003) J. Virol. 77(3): 2046-2055), immunostimulatory fusion proteins such as IL-2 fused to the Fe fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate ex In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)). pression vectors.

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by inter-facial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art and can be expressed as glycosylated nanoparticles according to the invemtion. One such immunogen is HIVA (described in WO 01/47955), which can be administered as a protein, on a plasmid (e.g., pTHr.HIVA) or in a viral vector (e.g., MVA. RIVA). Another such HIV immunogen is RENTA (described in PCT/US2004/037699), which can also be administered as a protein, on a plasmid (e.g., pTHr. RENTA) or in a viral vector (e.g., MVA. RENTA).

For example, one method of inducing an immune response against HIV in a human subject comprises administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

The findings highlight how the innate immune system recognizes HIV nanoparticles and the importance of antigen glycosylation in the design of improved nano-based vaccines.

EXAMPLES

Example 1

Materials and Methods

Immunogen Synthesis

Polyhistidine-tagged MD39 (MD39-6×His) and cysteine-terminal MD39-6×His were prepared as described previously (8, 14, 16). Briefly, trimer genes were synthesized and cloned into pHLsec by Genscript and then co-transfected with human furin on a pcDNA3.1 plasmid at a 2:1 trimer to furin DNA ratio using 293fectin into FreeStyle 293-F cells (ThermoFisher). Trimer supernatant was harvested five days post transfection by centrifugation and purified by affinity chromatography using HisTrap HP columns (GE Healthcare) followed by size-exclusion chromatography (SEC) using a S200 Increase column (GE Healthcare) in PBS at flow rate of 0.5 ml/min. The molecular weight of the trimer was confirmed by SEC multi-angle light-scattering (SEC-MALS) using DAWN HELEOS II and Optilab T-rEX instruments (Wyatt Technology). MD39-8mer, a nanoparticulate fusion of MD39 and ferritin from the hyperthermophilic archaeal anaerobe *Pyrococcus furiosus* (sequence in Supplementary Table 1), was produced and purified in a similar manner as MD39-6×His with these modifications: 1) the affinity chromatography step was done by overnight 4° C. incubation on *Galanthus Nivalis* Lectin agarose beads (Vector Laboratories #AL-1243), elution with Lectin Elution Buffer (1M Methyl a-D-mannopyranoside) followed by dialysis into PBS; and 2) the affinity chromatography (SEC) step was done using a Superose 6 or a Superose 6 Increase column (GE Healthcare) in PBS at flow rate of 0.5 ml/min.

Particle formation was assessed by SECMALS and by staining MD39-8mer with 2% uranyl formate, gridding and imaging by negative stain electron microscopy on a Philips CM100 TEM with a Soft Imaging Systems MegaView III CCD and SIA model 12C CCD cameras. eOD-GT8 monomer, trimer and 60mer were prepared as previously described (6, 14). Briefly, eOD monomer and trimer were produced and purified in a similar manner as MD39-6×His except that a Superdex 75 column (GE) was used for size-exclusion chromatography. eOD-GT8 60mer was purified using the same protocol as MD39-8mer. "Bare" ferritin was expressed in *E. coli* with a 6×His tag at the N-terminus of each ferritin subunit and purified by Ni++ chromatography followed by SEC.

Antibody Synthesis and Antigenicity Characterization of Immunogens

Broadly neutralizing antibodies (PGT121, PGT145, PGT151, PDGM1400, VRC01, 12A12, 3BNC60) and non-neutralizing antibodies (3074, 4025, B6, F105, 12N) were produced as IgG similar to the trimers, without the addition of furin protease. The antibodies were purified using a Capture Select IgG-CH1 column and dialyzed into PBS. Murine VRC01 chimera antibody sequence was designed by substituting the constant heavy and light chains of human VRC01 (32, 33) (obtained through the NIH AIDS Reagent Program, Division of AIDS, NIAID, NIH: CMVR VRC01 H, from Dr. John Mascola) with those from mouse IgG2c heavy chain and Ig kappa light chain. Chimeric sequences were synthesized as genomic blocks (Integrated DNA Technologies) and cloned into gWIZ expression plasmids (Genlantis). Plasmids were transiently transfected into Expi293 cells (ThermoFisher Scientific) using a 2:3 ratio by mass of the heavy chain and light chain plasmids. Cell culture supernatants were collected at 5 days post-transfection and antibody was purified in a ÄKTA pure chromatography system using HiTrap Protein A affinity columns (GE Healthcare Life Sciences).

To assess conformational/structural integrity and functionality of trimer immunogens, ELISAs were performed to analyze bNAb and non-nAb binding as described previously (16). Human PGT121 Fab was coated onto the ELISA plates (Corning™ 96-Well Half-Area Plates, Catalog #3690) at 2 μg/mL in 25 μL PBS pH 7.4 (Thermo Scientific, Catalog #10010-023) per well and incubated O/N at 4° C. Plates were washed 3× with PBS containing 0.2% (v/v) tween (PBST) (Tween 20, Sigma Catalog #P1379-1L) and blocked with PBST containing 5% (w/v) skim milk (BD Difco™ Skim Milk Catalog #232100) and 1% (v/v) Fetal Bovine Serum (FBS) (Thermo Fisher, Catalog #16000044) for 1 h at RT. Plates were then washed 3× and 25 μL of dilution series of primary Abs (starting at 10 μg/mL) in PBST+1% FSB were added for 1 h at 37° C. Plates were washed 5× and antibody binding was detected with 25 μL of anti-human IgG, Fcγ fragment specific, HRP-conjugated secondary antibody (Jackson ImmunoResearch Catalog #109-035-098) at a 1:5000 dilution in PBST+1% FBS for 1 h at RT. Plates were washed 3× and 25 μL TMB Chromogen Substrate Solution (Thermo Fisher Catalog #002023) was added. Development was stopped after 10 min with 25 μL 0.5 M $H_2SO_4$. Absorption was read at 450 and 570 nm on a VERSA max plate reader (Molecular Devices, USA). Background subtraction was performed by subtracting the 570 nm value from the corresponding 450 nm value. The data were subsequently analyzed in Prism (Prism v7; GraphPad Software, La Jolla, USA) to compute area under curve (AUC) by the trapezoidal method.

In Vitro B Cell Activation

VRC01 BCR-expressing Ramos Burkitt's lymphoma B cells were a gift from Daniel Lingwood at the Ragon Institute of MGH, MIT, and Harvard. Cells were stained with 10 μM of the calcium indicator fluo-4 (Thermo Fisher) for 30 minutes in serum-free RPMI prior to activation. Next, 250 μl cells at $1 \times 10^6$ cells/ml were stimulated with either MD39 or MD39-8mer at 10 μg/ml and fluo-4 signal was measured by flow cytometry. Cells were pre-warmed to 37° C. and then read for 45 seconds prior to addition of MD39 to set a baseline and then read for 4 additional minutes. All flow cytometry was carried out on a BD LSR II in the Swanson Biotechnology Center Flow Cytometry Core at the Koch Institute, MIT.

Synthesis of Trimer-Conjugated Liposomes

Lipids 1,2-dipalmitoyl-sn-glycero-3-phosphocholine (DPPC), 1,2-dioleoyl-sn-glycero-3-[(N-(5-amino-1-carboxypentyl) iminodiacetic acid) succinyl] (nickel salt) (DGS-NTA(Ni)), 1,2-dioleoyl-sn-glycero-3-phosphoethanolamine-N-[4-(p-maleimidophenyl) butyramide] (sodium salt) (MPB) and porcine brain sphingomyelin were purchased from Avanti Polar Lipids. Cholesterol was purchased from Sigma-Aldrich. For studies with fluorescent MD39-liposomes, MD39 was first conjugated with NHS-AlexaFluor 647 (ThermoFisher A20186) and purified from free dye according to the manufacturer's instructions. The degree of dye labeling was characterized by UV-vis spectroscopy prior to liposome coupling.

MD39-conjugated liposomes were prepared as previously described (8, 11) with some modifications. Briefly, unilamellar liposomes comprised of DPPC:sphingomyelin:DGS-NTA(Ni):MPB lipids in a 51.5:28.5:5:15 mole ratio were synthesized by lipid film rehydration and membrane extrusion using a 100 nm membrane at 50° C., followed by post-synthesis binding of 6×His-Cys C-terminal-modified MD39 trimer for 1 hour at 37° C. in PBS (final concentrations 2.1 μM MD39, 3.53 mM liposomes) followed by 16-18 hr incubation at 4° C. with rotation. Unconjugated MD39 was removed by size exclusion chromatography after coupling using Sepharose CL-2B resin (Sigma). Total conjugated MD39 was quantified by ELISA in the presence of 1% triton-X and 100 mM imidazole to fully disrupt liposomes and Ni-6×His interactions, respectively. MD39 trimer was captured on Nunc MaxiSorp plates coated with 2 μg/ml (mouse Fc) VRC01 and detected using 0.2 μg/ml PGT151, followed by secondary detection with 1:5000 goat anti-human IgG-HRP conjugate. Trimer-conjugated liposomes were also characterized by dynamic light scattering and cryoelectron microscopy (Jeol 2100F TEM) in the Swanson Biotechnology Center Nanotechnology Core at the Koch Institute, MIT. Mean liposome diameters from DLS were 93.2±25.0 nm (number average ±SD) with an average PDI of 0.054.

Synthesis of Saponin Adjuvant

The adjuvant used for all the described studies was an ISCOM-like nanoparticle comprised of self-assembled cholesterol, phospholipid, and Quillaja saponin prepared as previously described (34); all synthesis was performed under sterile conditions with sterile reagents. Briefly, 10 mg each of cholesterol (Avanti Polar Lipids 700000) and DPPC (Avanti Polar Lipids 850355) were dissolved separately in 20% MEGA-10 (Sigma D6277) detergent at a final concentration of 20 mg/ml and 50 mg Quil-A saponin (InvivoGen vac-quil) was dissolved in MQ $H_2O$ at a final concentration of 100 mg/ml. Next, DPPC solution was added to cholesterol followed by addition of Quil-A saponin in rapid succession and the volume was brought up with PBS for a final concentration of 1 mg/ml cholesterol and 2% MEGA-10. The solution was allowed to equilibrate at 25° C. overnight, followed by 5 days of dialysis against PBS using a 10 k MWCO membrane. The adjuvant solution was then filter sterilized using a 0.2 μm Supor syringe filter, concentrated using 50 k MWCO centricon filters, and further purified by FPLC using a Sephacryl S-500 HR size exclusion column. Each adjuvant batch was finally characterized by negative stain TEM and DLS to confirm uniform morphology and size and validated for low endotoxin by Limulus Amebocyte Lystae assay (Lonza QCL-1000). Final adjuvant concentration was determined by cholesterol quantification (Sigma MAK043).

Procainamide Labelling of Glycans and HILIC-UPLC

N-glycans were enzymatically released from gel bands by digestion with Peptide-N-Glycosidase F (PNGase F, New England Biolabs) at 37° C. for 16 hours. Glycans were fluorescently labelled with procainamide (110 mg/mL procainamide, 6 mg/mL sodium cyanoborohydride in 30% DMSO, 70% acetic acid) at 65° C. for 4 hours. Excess label was removed using Spe-ed Amide 2 cartridges (Applied Separations).

Glycans were analysed on a Waters Acquity H-Class instrument, using a Glycan BEH Amide column (2.1 mm×100 mm, 1.7 uM, Waters) using the following gradient: Time (t)=0: 22% A, 78% B (flow rate=0.5 mL/min); t=38.5: 44.1% A, 55.9% B (0.5 mL/min); t=39.5: 100% A, 0% B (0.25 mL/min); t=44.5: 100% A, 0% B (0.25 mL/min); t=46.5: 22% A, 78% B (0.5 mL/min), where solvent A was 50 mM ammonium formate (pH 4.4) and B was acetonitrile. Fluorescence was measured at an excitation wavelength of 310 nm and an emission wavelength of 370 nm. Data were processed using Empower 3 software (Waters). Fluorescently labelled digests were digested with Endoglycosidase H (Endo H) at 37° C. for 16 hours: Glycans were extracted using a polyvinylidene fluoride (PVDF) protein-binding membrane (Millipore) and subsequently analysed as above. To determine the fine processing of complex-type glycans, three separate aliquots of endoH-treated glycans were further digested with: α2,3 neuraminidase only, α2,3,6 neuraminidase and finally a combination of α2,3,6 neuraminidase and β1,4 galactosidase (all New England Biolabs). The glycans were then extracted using a PVDF protein-binding membrane (Millipore) and analyse as above. These digests enabled the oligomannose: complex ratio to be determined as well as the abundance of complex-type glycans terminating with particular saccharide residues.

Immunizations

Balb/c, C57BL/6, C3 KO, Cr1/Cr2 KO, and MBL KO mice were purchased from Jackson Laboratory (Bay Harbor, Me.). Mice were housed under specific pathogen-free conditions. All procedures used in this study were approved by the Committee on Animal Care at the Massachusetts Institute of Technology following local, state, and federal regulations.

Female mice 6-10 weeks of age were immunized with immunogen and adjuvant via subcutaneous tail-base injection with 50 μl on either side of the tail. Mice immunized with eOD, eOD-3mer, eOD-60mer, or HA-8mer received a total of 2 μg eOD or HA, while mice immunized with MD39, MD39-8mer, or MD39-liposomes received either 1 or 5 μg MD39. For immunizations with particle immunogens, total molar equivalence of immunogen was kept constant, approximately 0.1 nmol for eOD and 5 pmol or 25 pmol for MD39, equivalent to 3.7 μg eOD-60mer and 1.3 or 6.4 μg MD39-8mer, respectively. All immunizations included 5 μg saponin adjuvant unless otherwise noted. For a few experiments, monophosphoryl lipid A (MPLA PHAD, Avanti Polar Lipids 699800) or CpG 1826 DNA (5'-tc-catgacgttcctgacgtt-3', InvivoGen tlrl-1826) were used as alternate adjuvants. For trafficking studies, mice were similarly immunized with AlexaFluor 647-tagged immunogens (ThermoFisher A20186). Immunogens were characterized by UV-vis spectroscopy and contained ~1 dye/monomeric eOD and ~45 dyes/eOD-60mer (i.e. ~0.75 dyes/monomer) while each MD39 trimer contained ~5.7-6.1 dyes/trimer and ~44-45 dyes/MD39-8mer (i.e. ~5.6 dyes/trimer). Trimers on liposomes were similarly pre-labeled prior to liposome conjugation as soluble trimers. For trafficking in knockout animals, equal mixtures of female and male mice were used due to availability. For trafficking of bare nanoparticles, mice were immunized with 2 μg of Alexa-Fluor 647-tagged nanoparticle. Mice were then injected subcutaneously in the tail base with 4 μg BV421-labeled anti-CD35 (BD Biosciences 740029) 16-18 hours prior to LN excision to label follicles in situ. Injection of 20 μg PE-labeled anti-CD157 (Biolegend 140204) one day prior to lymph node removal was used as an alternative to label B cell follicles for mice lacking complement receptor 1, while injection of anti-CD157 three days prior to lymph node removal was used to label active germinal centers (35).

LI-COR Immunogen Tracking

Balb/c mice were immunized (as described above) with 5 μg IR dye 800CW NHS-Ester (LI-COR Biosciences) labeled MD39 or MD39-8mer and 5 μg saponin adjuvant or with 2 IR dye 800CW NHS-Ester labeled eOD or eOD-60mer and 5 μg saponin adjuvant. At specified times, draining lymph nodes were excised and fluorescence was measured using a LI-COR Odyssey CLx Infrared Imaging System. Fluorescence was reported as the total integrated intensity for each set of lymph nodes.

Antibody Titer Analysis

Blood samples were collected from immunized mice via retro-orbital bleeds and serum was isolated. MaxiSorp plates (ThermoFisher 44-2404-21) were coated with either 2 μg/ml immunogen or 1 μg/ml rabbit anti-polyhistidine antibody (Genscript) followed by 2 μg/ml HIS-tagged immunogen. Analysis of IgG responses elicited by immunization with deglycosylated immunogens was carried out by coating ELISA plates with the matching deglycosylated antigen. Plates were blocked overnight in a solution containing 1×PBS, 5% skim milk, 10% goat serum, 1% BSA, 1% FBS, and 0.2% Tween-20. In the case of plates coated with anti-polyhistidine antibodies, polyhistidine-tagged immunogen was then added and allowed to incubate for two hours.

Plates were washed four times in 1×PBS containing 0.2% Tween-20, and dilutions of serum in blocking buffer were added and incubated for two hours. Plates were washed as before and an HRP-conjugated anti-mouse IgG was added and incubated for one hour. For analyses of antigen-specific IgG isotype titers, HRP-conjugated anti-mouse IgG1, IgG2a, IgG2b, and IgG3 antibodies were used at this step. Plates were then washed and TMB was added. The reaction was stopped with sulfuric acid once the wells containing the lowest dilutions of TMB began to develop visually and the absorbance of each well was determined. All titers reported are inverse dilutions where $A_{450\ nm}$-$A_{540\ nm}$ (reference wavelength) equals 0.2.

Bio-Layer Interferometry

All bio-layer interferometry measurements were conducted using a ForteBio Octet RED96 instrument in the MIT Biophysical Instrumentation Facility. eOD monomer was biotinylated via NHS-amine chemistry (ThermoFisher 21925). Streptavidin-coated biosensors were incubated in PBS containing 1% BSA, then moved to wells containing the same solution with 3 ug/ml biotinylated monomeric eOD for five minutes. Nonspecifically bound eOD was removed with a three minute baseline step, and eOD-coated biosensors were moved to wells containing dilutions of polyclonal IgG from immunized mice for five to ten minutes. The biosensors were then moved back to the baseline solution and dissociation of IgG from the biosensors was detected. For dissociation constant analysis of MBL binding to eOD and MD39 formulations, the same protocol was performed in PBS containing 1% BSA and 0.1 M CaCl. Streptavidin-coated biosensors were loaded in solution containing 1 μg/mlbiotinylated mouse MBL for several minutes. Excess MBL was washed off and MBL-coated biosensors were moved to wells containing dilutions of antigen formulations until probes began to become saturated. The biosensors were then moved back to the baseline solution and antigen was allowed to dissociate.

Germinal Center and $T_{fh}$ Analysis

Mice were sacrificed by CO2 inhalation and both inguinal lymph nodes were harvested at specified days. Lymph nodes were processed into single-cell suspensions using enzymatic digestion with 0.8 mg/ml Collagenase/Dispase and 0.1 mg/ml DNAse (Roche Diagnostics) in complete RPMI (with 10% FBS and antibiotics) at 37° C., followed by passage through a 70-μm cell strainer (BD Biosciences). Next, cells were washed with PBS and stained with Live/Dead Aqua (Life Technologies) for 15 minutes at 25° C. Samples were then treated with anti-CD16/32 Fc block (BioLegend 14-0161-85), followed by staining with anti-CD3e-PerCP-Cy5.5 (BD Biosciences 5204845), anti-B220-PE-Cy7 (BioLegend 103222), anti-IgD-APC (eBioscience 17-5993-82), anti-GL7-FITC (BioLegend 144604), and PNA-biotin (VectorLabs ZB1228)+streptavidin-APC-Cy7 (BD Biosciences 554063) in PBS/1% BSA and finally fixed and stored at 4° C. until analysis. Alternatively, to simultaneously stain for germinal center B cells and T follicular helper cells, cells were similarly stained with Live/Dead Violet (Life Technologies) followed by Fc block and staining with anti-B220-BV510 (BD Biosciences 563103), anti-IgD-APC (eBioscience 17-5993-82), nti-GL7-FITC (BioLegend 144604), anti-CD38-APC-Cy7 (BioLegend 102727), anti-CD4-PerCP-Cy5.5 (eBioscience 45-0042-82), anti-CD44-AlexaFluor700 (BioLegend 103026), anti-PD1-PE-Cy7

(eBioscience 25-9985-82), and anti-CXCR5-biotin (BD Biosciences 551960)+streptavidin-PE (BioLegend 405204) in PBS/1% BSA and finally fixed and stored at 4° C. until analysis. Flow cytometry was carried out on a BD LSR Fortessa.

For studies in which antigen-specific $T_{fh}$ was assessed, analysis was performed as previously described (36, 37). Briefly, $1×10^6$ cells were stimulated with 5 μg/ml of intact antigen (monomeric eOD or trimeric MD39) in addition to 5 μg/ml of an overlapping peptide pool for 18 hours at 37° C. Unstimulated cells were run as a control. Cells were then washed and similarly stained with Live/Dead Aqua and treated with anti-CD16/32 Fc block (BioLegend 14-0161-85), followed by staining with anti-B220-BV510 (BD Biosciences 563103), anti-CD4-PerCP-Cy5.5 (eBioscience 45-0042-82), anti-CD44-AlexaFluor700 (BioLegend 103026), anti-PD1-PE-Cy7 (eBioscience 25-9985-82), anti-OX40-APC (BioLegend 119413), anti-CD25-FITC (BioLegend 101907), anti-PDL1-BV421 (BioLegend 124315), and purified rat anti-CXCR5 (BD Biosciences 551961)+goat anti-rat IgG-biotin (Jackson Immunoresearch 112-065-167)+streptavidin-PE (BioLegend 405204) in PBS/2% normal mouse serum/2% FBS/1% BSA and finally fixed and stored at 4° C. until analysis. Flow cytometry was carried out on a BD LSR Fortessa.

Lymph Node Processing for Whole-Tissue Imaging

For whole-tissue imaging, lymph nodes were excised from mice and fixed overnight at 4° C. in 4% paraformaldehyde. Lymph nodes were then processed as previously described (33) with some modifications to improve protein retention in lymph nodes. Briefly, they were washed twice in PBS and excess fat and connective tissue was removed. Nodes were then gradually moved into solutions containing successively high concentrations of methanol over the course of several hours until they were incubated for half an hour in pure methanol. Nodes were then briefly bleached in hydrogen peroxide for one minute before being returned to methanol for half an hour. They were then gradually moved into solutions containing increasing concentrations of tertiary-butanol before eventually being incubated in pure tertiary-butanol for one hour. All solutions used after bleaching contained an additional 0.4% α-tocopherol (vitamin E). Nodes were then removed from solution and allowed to dry completely before being placed in dichloromethane. After the lymph nodes dropped to the bottom of tubes following swirling (indicating removal of remaining tertiary-butanol), they were stored in dibenzylether with 0.4% α-tocopherol, which was used as an optical clearing solution.

Lymph Node Processing for Immunofluorescence Microscopy

Lymph nodes were excised from mice and fixed in 4% paraformaldehyde at 37° C. for two hours. Lymph nodes were then washed in PBS (three times, five minutes each) before being embedded in 3% agarose. Nodes were cut into 100 μm thick slices. The slices were blocked in 10% goat serum for one hour and then stained with anti-B220 and anti-Ki67 overnight at 37° C. The slices were then washed in PBS (three times, one hour each) and mounted on slides.

Confocal Microscopy and Image Processing

Whole lymph nodes were imaged using an Olympus FV1200 Laser Scanning Confocal Microscope. Lasers were set to minimize pixel saturation in the brightest samples. All laser and channel settings were then kept constant across time points for individual studies to allow for direct comparison between different samples. Each lymph node was imaged over 300 μm.

Lymph node slices were imaged using a Leica SP8 Laser Scanning Confocal Microscope. Laser settings were determined similarly to as described for whole lymph node imaging.

Microscopy images were analyzed using ImageJ. To reduce background signal bleeding into other channels, each channel other than the 405 nm channel was passed through an HSB filter against background fluorescence. Z-stacks were then condensed into average intensity projections ranging over the full 300 μm displaying the average intensity of each color for each pixel.

To quantify immunogen signal and follicle colocalization, first the maximum intensity z-projection on all channels was binarized and used to define a selection comprising the whole lymph node area. Next, for each z-height slice in the imaged sample, a high-pass filter was applied such that the brightest pixels in the background autofluorescence channel were binarized. These bright pixels in the autofluoresence channel were zeroed in the signal channels in an attempt to mitigate the intensity effects of bleedthrough from autofluorescence into the signal channels (i.e.: a pixel [x,y,z] of bright autofluorescence was zeroed for corresponding [x,y,z] for all pixels across all signal channels). Although this method may reduce true signal (resulting in an underestimated intensity quantitation), it successfully removes a substantial contribution from autofluorescence to the true signal intensity by wholly removing the pixels most prone to bleedthrough from autofluorescence. A sum intensity z-projection on the combined CD35+PNA/CD157 channels was binarized and used to define a selection comprising the follicular area. Finally, a sum intensity z-projection on the immunogen signal channel (following autofluorescence reduction) was binarized using a high pass filter such that bright pixels were applied an intensity value of 1, while dim pixels were applied an intensity value of 0. This binary mask was used to multiply a sum intensity z-projection such that all dim pixels were zeroed while all bright pixels retained their unaltered intensity information. This was done to prevent skewing of immunogen signal from the high number of near-zero background pixels that existed despite autofluorescence signal reduction. The intensity of only these bright pixels was measured within both the whole lymph node and follicular areas for use in ratiometric antigen signal intensity calculations (i.e. % immunogen within follicles). In addition, only bright pixels were quantified to identify overall immunogen signal distribution within follicles (i.e. % immunogen+follicular area).

C3 and MBL Assays eOD formulations were coated directly on to MaxiSorp plates in 50 μl PBS at 3 μg/ml eOD. Plates were then blocked overnight in PBS containing 1% BSA and 0.1 M CaCl. For MBL assays, dilutions of MBL were added and plates were incubated for two hours. For C3 assays, dilutions of normal or MBL KO mouse serum were added and plates were incubated at 37 C for two hours, with a maximal concentration of 30% serum. Plates were then washed four times in PBS containing 0.1% Tween-20 and anti-MBL or anti-C3 antibodies were added, followed by another two-hour incubation. Plates were washed as before and HRP-conjugated secondary antibodies were added. Following an hour-long incubation and additional washes, TMB was added and plates were developed until the lowest dilution wells started to visually show signal. The reaction was then stopped with sulfuric acid and the absorbance at 450 nm was read via plate reader.

eOD-60Mer Deglycosylation eOD-60mer was deglycosylated using PNGase F (New England BioLabs P0704S) under non-denaturing conditions following the manufacturer's guidelines. Deglycosylation was confirmed via SDS-PAGE gel using glycoprotein stain (ThermoFisher 24562). eOD-60mer was confirmed to maintain its structure using dynamic light scattering and cryotransmission electron microscopy. The retention of immunogen conformation on the surface of eOD-60mer was confirmed via ELISA against VRC01 as compared to unmodified eOD-60mer.

Bone Marrow ELISPOT

Total IgG and antigen-specific IgG ELISPOTs were carried out using a mouse IgG ELISpotBASIC (ALP) protocol from Mabtech with some modifications. One day prior to cell seeding, Millipore multiscreen PVDF well-plates were pre-treated for 1 minute with 35% ethanol, followed by overnight coating at 4° C. with 10 μg/ml polyclonal anti-mouse IgG (Mabtech) in phosphate buffer. The next day, wells were washed with PBS/0.5% BSA and blocked with complete RPMI (with 10% FBS and antibiotics). Bone marrow from both hind legs (femur and tibia) of immunized balb/c mice was harvested and ACK lysed for 1 minute, followed by washing in PBS/1% BSA. 100,000 cells were plated in 250 μl complete RPMI for 4 hours at 37° C. All samples were plated in duplicate wells. Cells and media were then washed away and spots were detected using either 1 μg/ml biotinylated rat anti-mouse IgG monoclonal antibody (Mabtech) for total B cell responses or 2 μg/ml biotinylated eOD monomer (prepared by reacting eOD with NHS-PEG2-biotin for 2 hours at 25° C. at a eOD:NHS ratio of 1:20) for antigen-specific B cell responses for 2 hours, followed by secondary detection with streptavidin-ALP conjugate (Mabtech) for 1 hour at 25° C. Spots were finally developed using 5-bromo-4-chloro-3-indolyl phosphate/nitroblue tetrazolium chloride substrate solution (BCIP/NBT-plus; Mabtech) for 5 minutes. Plates were scanned using a CTL-ImmunoSpot Plate Reader and data were analyzed using CTL ImmunoSpot Software.

Conjugation of 4-aminophenyl 1,3-α-1,6-α-D-mannotrioside to fluorescent latex beads Three sizes of FluoSpheres™ Carboxylate-Modified Microspheres (red fluorescent, 580/605; ThermoFisher) with diameters of approximately 40, 100, and 200 nm were functionalized with 4-aminophenyl 1,3-α-1,6-α-D-mannotrioside (Synthose) using the bead manufacturer's suggested protocol: For the 100 nm and 200 nm beads, 1.00 mL of the 2-wt % stock was combined with 0.10 mL of a 0.50 M 2-(N-Morpholino)ethanesulfonic acid (MES) buffer (pH 6.0) and 0.75 mg of 4-aminophenyl 1,3-α-1,6-α-D-mannotrioside and thoroughly mixed. To this solution, 10.0 mg of 1-ethyl-3-(3-dimethylaminopropyl)carbodiimide hydrochloride (EDC, ThermoFisher) was added and the solution was incubated with shaking at 22° C. for 18 hr. For the 40 nm beads, 0.10 mL of the 5-wt % stock provided by the manufacturer was combined with 0.90 mL of deionized water, 0.10 mL of a 0.50 M 2-(N-Morpholino)ethanesulfonic acid (MES) buffer (pH 6.0), and 0.75 mg of 4-aminophenyl 1,3-α-1,6-α-D-mannotrioside and reacted under the same conditions as those used for the 100 nm and 200 nm beads. The reactions were quenched by the addition of 0.10 mL of a 1.0 M glycine solution in deionized water and then transferred to 20K MWCO dialysis cassettes. The samples were dialyzed first against 0.5× phosphate buffered saline for 24 hr, and then dialyzed against deionized water for 24 hr two times. The 40 nm particles showed evidence of aggregation post-functionalization and were redispersed by the addition of 0.010 mM 1,2-di stearoyl-sn-glycero-3-phospho-ethanolamine-N-[methoxy(polyethyl ene glycol)-2000] (Avanti Polar Lipids) followed by brief sonication. Finally, they were passed through a 0.2 μm pore size syringe filter before use. Bare 40 nm particles were treated in the same way. Successful glycan functionalization was confirmed by Biolayer interferometry measurements of recombinant MBL binding to the functionalized particles.

Conjugation of 4-aminophenyl 1,3-α-1,6-α-D-mannotrioside to Ferritin Nanoparticles A solution of AF647-labeled ferritin nanoparticles (0.10 mg) in 0.130 mL of PBS buffer was combined with 0.040 mL of 0.5 M 2-(N-Morpholino)ethanesulfonic acid (MES) buffer (pH 6). To this solution, 0.50 mg of 4-aminophenyl 1,3-α-1,6-α-D-mannotrioside (Synthose) was added with mixing by gentle vortexing. In order to activate the carboxylic acid groups on the ferritin particles, the coupling agent 1-ethyl-3-(3-dimethylaminopropyl)carbodiimide hydrochloride (EDC, ThermoFisher) was introduced slowly over time. Specifically, a total of 1.2 mgs of EDC was added in 0.2 mg aliquots from an EDC stock solution at 100 mg/mL in water over the course of 25 minutes. In a parallel reaction, to achieve lower amounts of functionalization the amount of mannotrioside and the amount of EDC were reduced by a factor of 10 to 0.050 mg and 0.120 mg, respectively. Both solutions were gently vortexed at frequent intervals during the addition and then allowed to react for 1 hour at 22° C. The reactions were stopped by the addition of 0.10 mL of a 1.0 M glycine solution in water and then purified using an Amicon Ultra-0.5 mL centrifugal filter (30K MWCO) with 5 cycles of concentration to 0.1 mL followed by addition of 0.4 mL of PBS. The degree of functionalization of the ferritin subunit was estimated using MALDI-tof MS with sinapinic acid as the matrix. Before functionalization, the bare ferritin subunit showed a predominant peak at 21.4 kDa. For the ferritin functionalized with the higher levels of mannose, a predominant peak at 24.0 kDa was observed, corresponding to ~4 mannotrioside moieties added per subunit and thus a total of ~96 per nanoparticle. For the ferritin functionalized with the lower levels of mannose, strong peaks were observed suggesting that subunits with 0, 1, and 2 mannotrioside moieties were the predominant species and thus it was estimated that on average every 24-subunit ferritin particle would have ~24 mannotrioside moieties.

Statistics

Statistical analyses were performed using GraphPad Prism software. All values and error bars are shown as mean±standard deviation, with the exception of serum titer data that are shown as mean±95% confidence interval. Serum titers were analyzed using a Mann-Whitney test. All other data was analyzed using an unpaired t test for direct comparisons or an ordinary one-way ANOVA followed by a Tukey's post-test to compare multiple groups, unless otherwise noted.

Example 2

To define pathways regulating the HIV immune response to multivalent particulate antigens in vivo, the fates of two distinct HIV envelope antigens as soluble monomers or as protein nanoparticles were examined. A germ line-targeting engineered outer domain of gp120 (eOD-GT8, herein referred to as eOD) and a gp140 envelope trimer (MD39) (6, 14-16) were compared. The trimer is an improved version of BG505 SOSIP gp140 with enhanced thermal stability and expression level and reduced exposure of the V3 loop (8, 17). These two antigens were selected as representatives of "reductionist" antigens designed to elicit an immune response against a particular neutralizing epitope and of whole-envelope protein immunogens bearing multiple neutralizing sites, respectively.

Figures 1A, 1B, 1C, 1D, 1E:
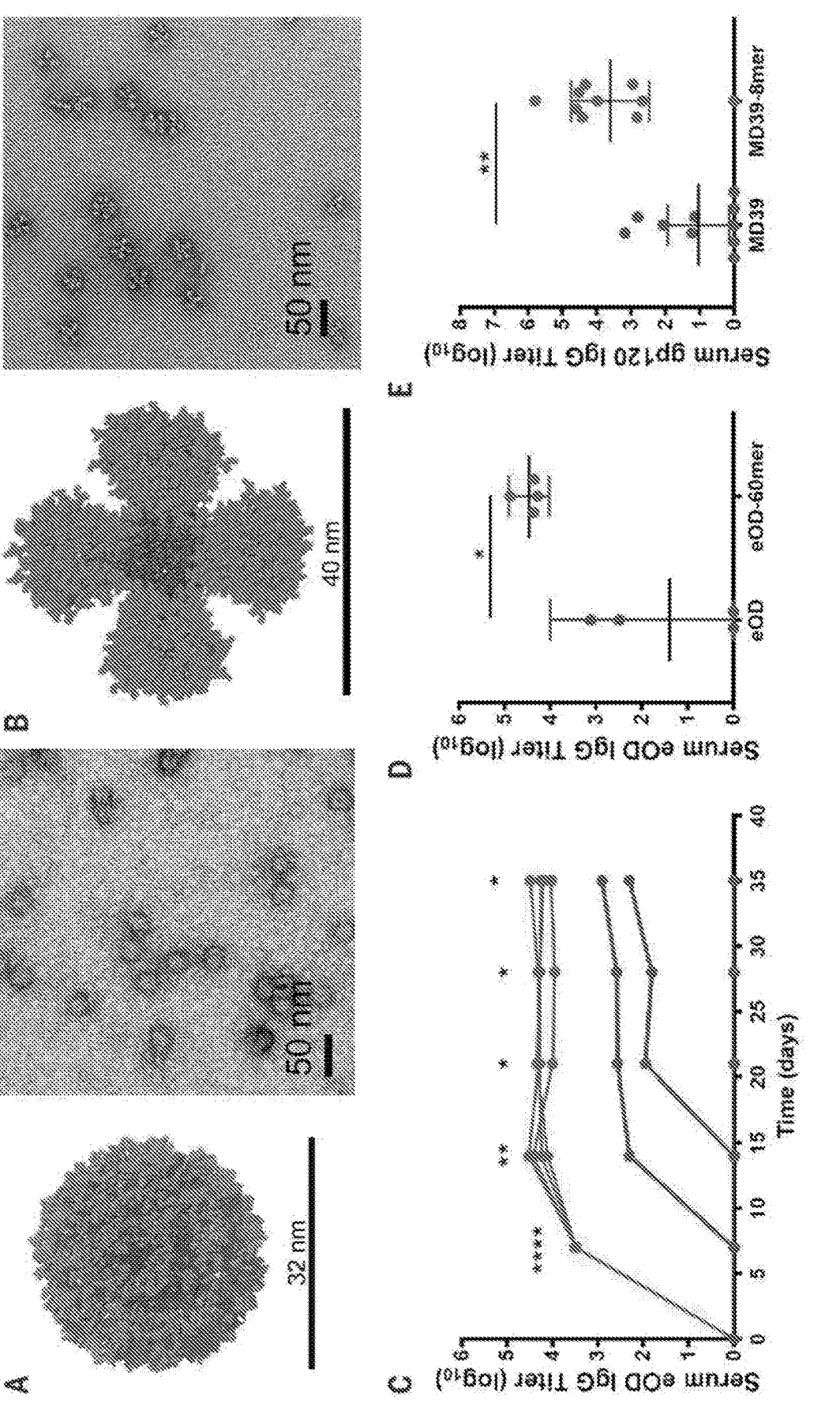
FIG. 1A-1J. Nanoparticle forms of gp120 and envelope (Env) trimer immunogens elicit enhanced humoral immune responses. (A and B) Model representations and TEM images of (A) eOD-60mer and (B) MD39-8mer nanoparticles. eOD or MD39 is shown in green, glycans are shown in blue, and the lumazine synthase or ferritin core is in red. (C and D) BALB/c mice (n=4 mice per group) were immunized with 2 mg of the eOD monomer (blue) or 3.7 mg of eOD-60mer (red), with each preparation containing the same number of moles of eOD, together with saponin adjuvant. Shown are (C) serum eOD-specific IgG titers analyzed over time by ELISA and (D) individual titers 1 month post-immunization. Data represent the means with 95% confidence intervals (CIs) from one of five independent experiments. (E) BALB/c mice (n=10 per group) were immunized with 1 mg of MD39 or ~1.3 mg of MD39-8mer, with each preparation containing the same number of moles of trimer, together with saponin adjuvant and received a booster immunization at 6 weeks; individual gp120-specific IgG titers were analyzed 3 weeks post-booster immunization by ELISA. Data show the means with 95% CIs from one of three independent experiments. (F to I) Mice were immunized with eOD or MD39 as described for (C) and (E); [(F) and (G)] absolute (abs.) counts of antigen-specific $T_{fh}$ cells and [(H) and (I)] GC B cells in lymph nodes from individual mice were determined by flow cytometry on day 7. Shown are the means with SD from one of three independent experiments. (J) Dissociation rates ($k_{off}$) of day-21 purified polyclonal IgG bound to immobilized eOD analyzed via biolayer interferometry for mice immunized with eOD or eOD-60mer. Shown are the means and SD from one of three independent experiments. ns, not significant; P<0.05; P<0.01; *P<0.001; ****P<0.0001, determined by a Mann-Whitney test (serum titers), one-way analysis of variance (ANOVA) followed by Tukey's multiple comparisons test (for GC Tfh cells), or an unpaired t test.
Figures 1F, 1G, 1H, 1I, 1J:
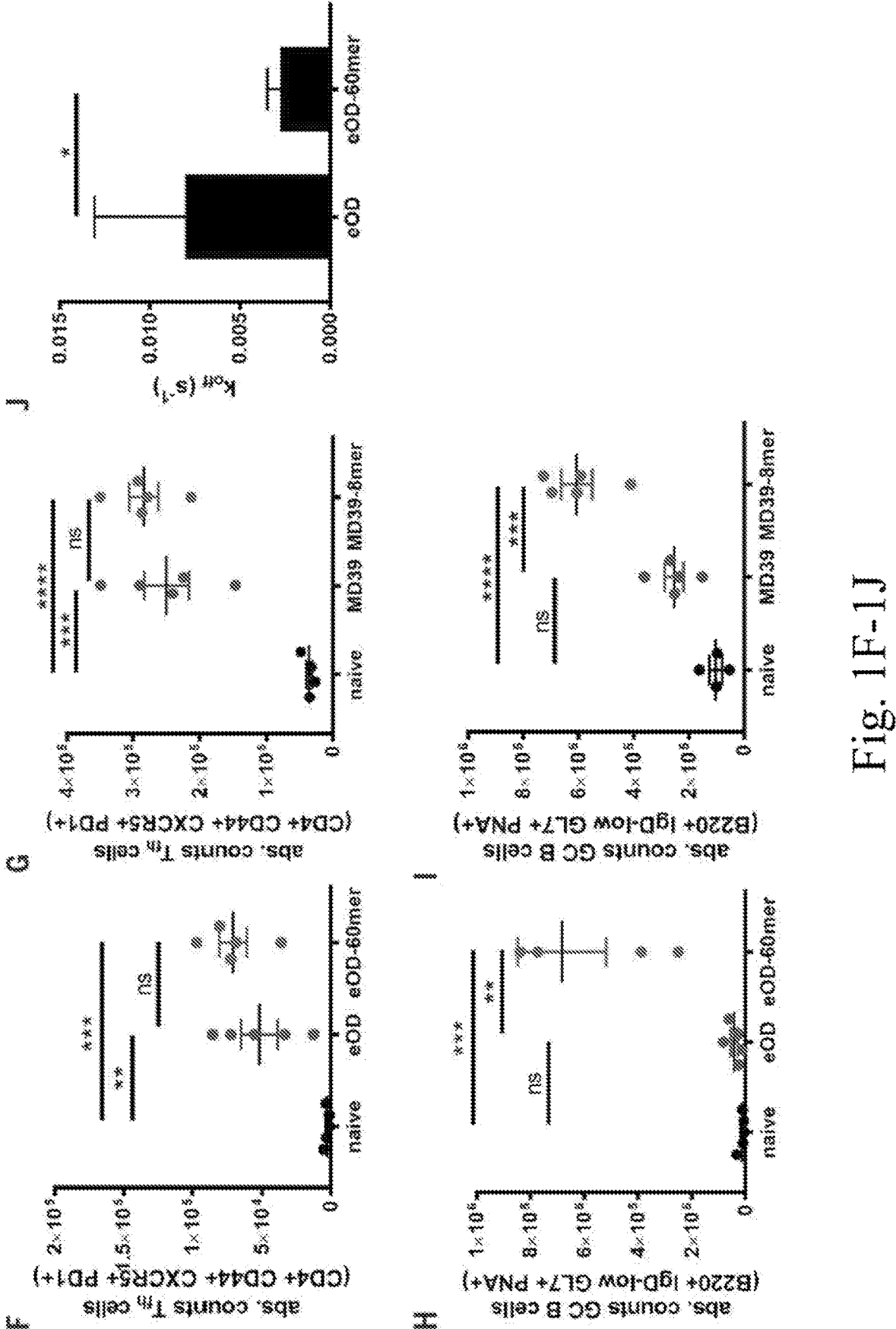
Figures 5A, 5B, 5C, 5D, 5E:
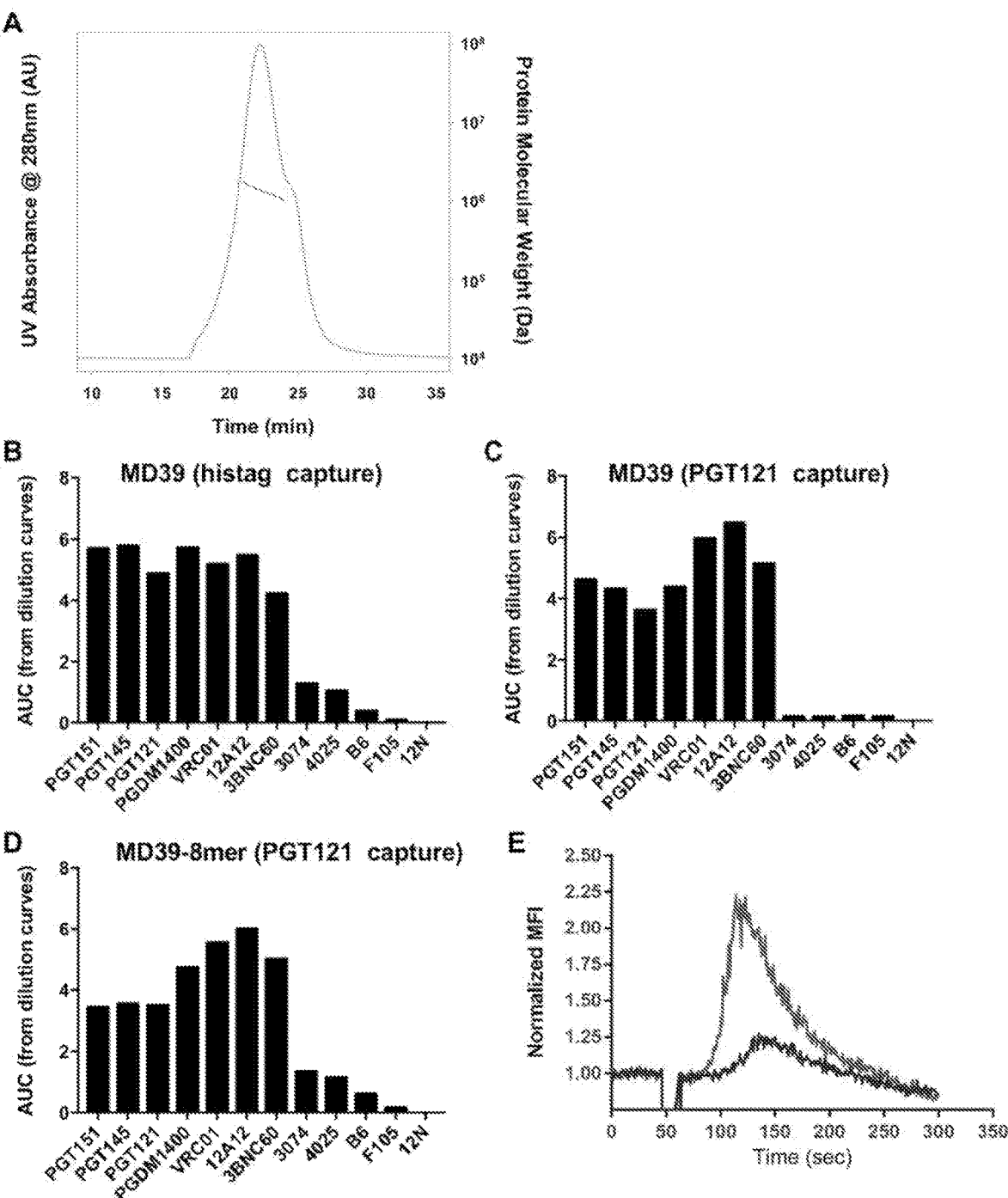
FIG. 5A-5E. Characterization of MD39-8mer nanoparticle immunogens. (A) MD39-8mer SECMALS elution profile showing relative UV absorbance at 280 nm (red) and total protein molecular weight (black). Molecular weight across the peak is 0.7-2.7×10⁶ Da, corresponding to 32%-126% of the MW of a perfect MD39-8mer. (B-D) ELISA binding profile of MD39 trimers immobilized on plates via (B) anti-histag or (C) PGT121 capture, and (D) comparison to MD39-8mer captured by PGT121. Shown are binding of broadly neutralizing (PGT151, PGT145, PGDM1400, VRC01, 12A12, 3BNC60, PGT121) and non-neutralizing (F105, 3074, 4025, B6, 12N) antibodies to the immobilized immunogens. (E) Comparison of calcium flux (fluo-4 mean fluorescence intensity, MFI) by VRC01-expressing B cells in response to 10 μg/ml MD39 (blue) or MD39-8mer (red).
Figures 6A, 6B:
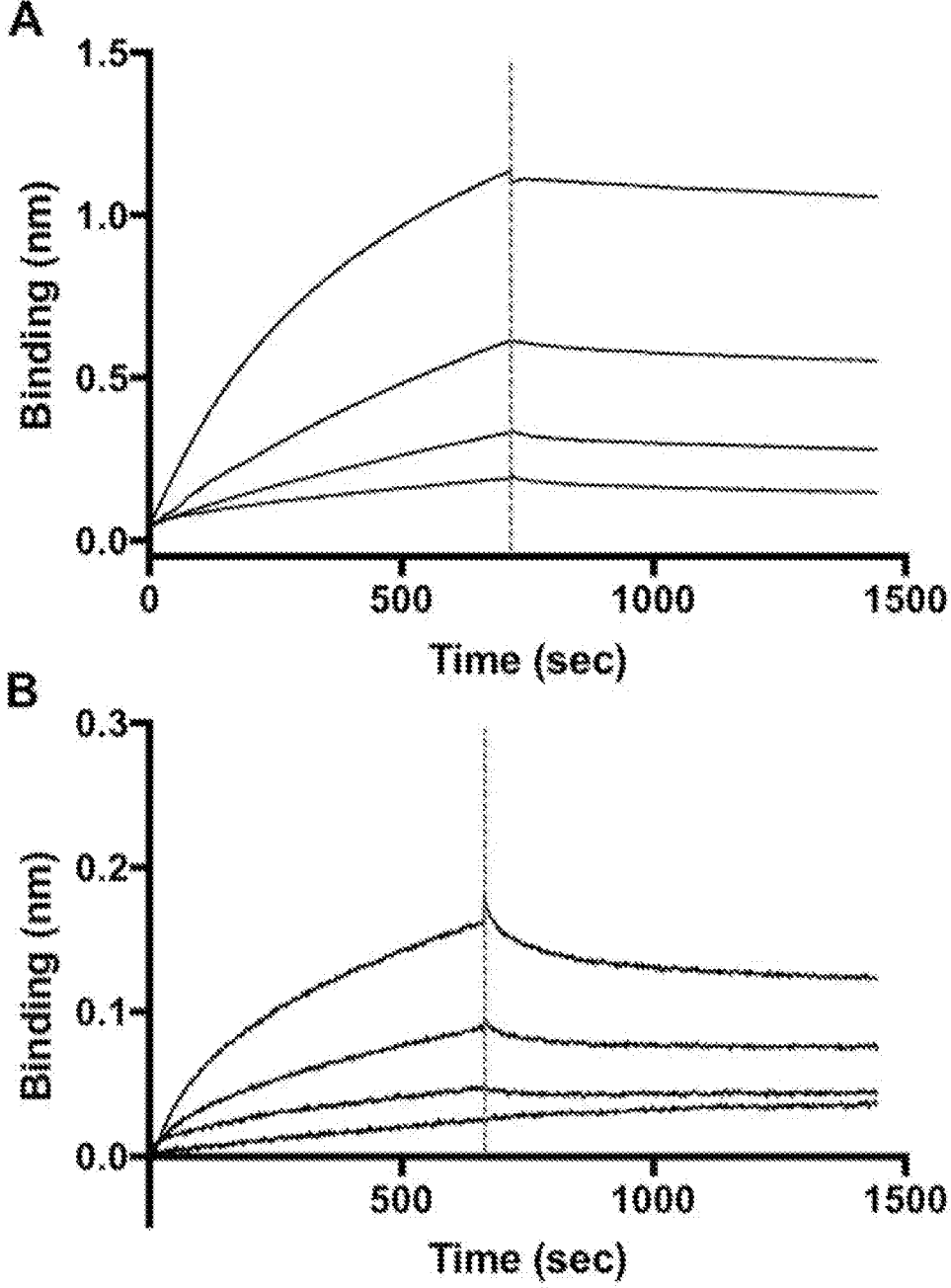
FIG. 6A-6B. Association and dissociation curves of polyclonal IgG from eOD-immunized mice. Association and dissociation of day 21 purified polyclonal IgG from mice immunized with (A) eOD-60mer or (B) eOD monomer to eOD monomer.

To generate the protein a particles, eOD was formulated as a ~32-n n-diameter nanoparticle (eOD-60mer) by fusion to a bacterial protein, lumazine synthase, which self-assembles into a 60-mer as previously described (FIG. 1A) (14-16). By contrast, a ~40-nm-diameter nanoparticle form of MD39 (MD39-8mer) was generated by fusing the MD39 gp140 chain to an archaeal ferritin; 24 subunits of ferritin self-assemble to form a nanoparticle (ferritin core outer diameter, ~12 nm) displaying eight copies of gp140 trimer (FIG. 1B) (13, 18). MD39-8mer eluted as a relatively uniform peak in size exclusion chromatography, showed an enzyme-linked immunosorbent assay (ELISA) binding profile to neutralizing and nonneutralizing $_{monoclonal}$ antibodies consistent with expectations for the MD39 trimer (13), and was observed to have a reasonably homogeneous morphology by transmission electron microscopy (TEM) (FIG. 1B and FIG. 5, A to C). In vitro, both eOD-60mer and MD39-8mer nanoparticles stimulated stronger calcium signaling in VRC01-expressing B cells than their monomer counterparts (6) (FIG. 5D). In immunized mice, the nanoparticle forms of eOD and MD39 elicited higher immunoglobulin G (IgG) titers (up to 90 times as high) than the soluble immunogens (FIG. 1, C to E). Analysis of responding cells in lymph nodes (LNs) revealed that $T_{fh}$ cell responses were not altered by nanoparticle immunization (FIGS. 1, F and G) but that GC B cells were substantially increased (FIGS. 1,H and I). A deeper analysis of eOD-immunized animals further showed that polyclonal IgGs isolated from eOD-60mer-immunized sera exhibited lower off rates than IgG from monomer-immunized animals, indicative of enhanced affinity maturation (FIG. 1J and FIGS. 6, A and B). Thus, the nanoparticle forms of either eOD or MD39 elicited substantially enhanced humoral responses in vivo compared with their monomer forms.

Figures 2A, 2B, 2C:
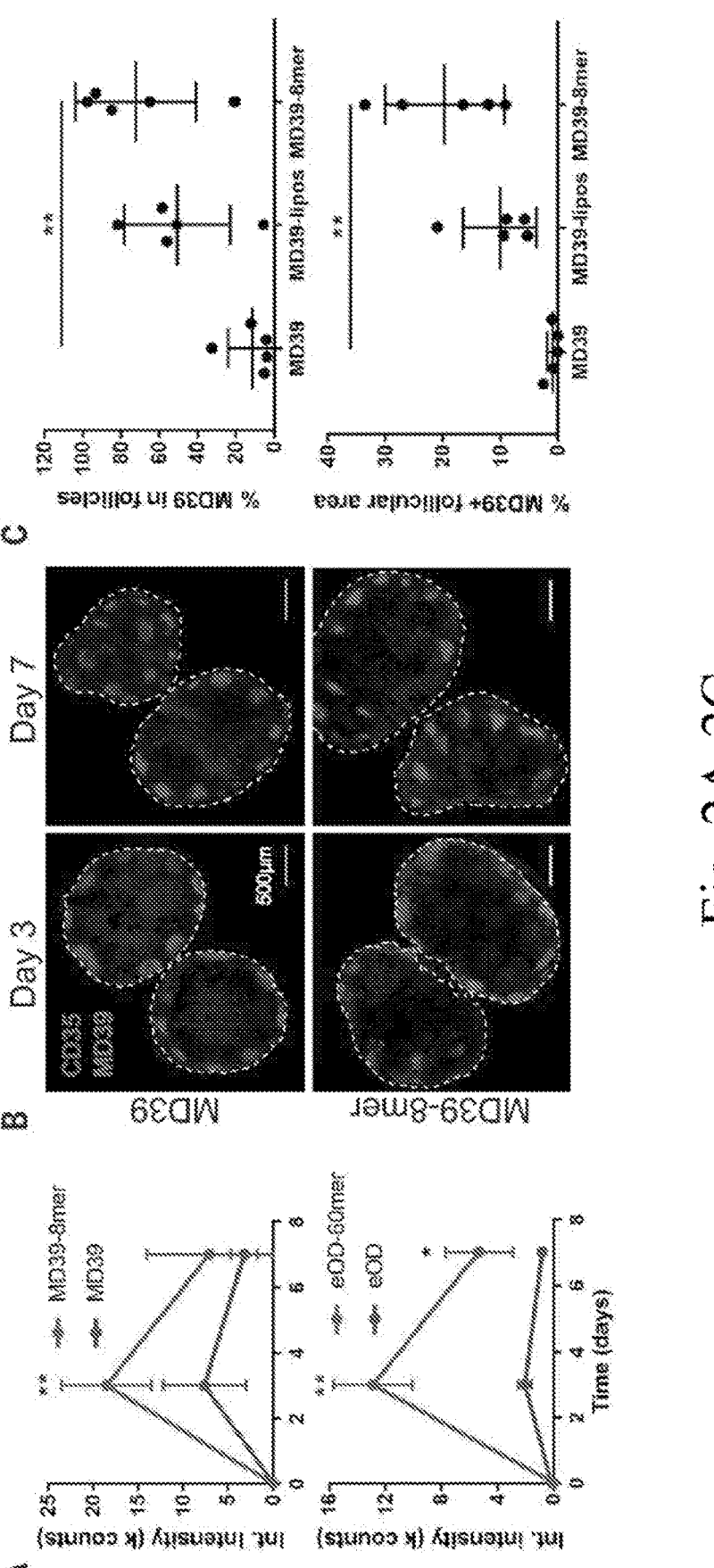
FIG. 2A-2F. Nanoparticle eOD and MD39 trimer immunogens are targeted to the FDC network and concentrated in GCs. (A) BALB/c mice (n=4 to 5 mice per group) were immunized with IR dye-labeled MD39, MD39-8mer, eOD, or eOD-60mer, and total fluorescence integrated (Int.) intensity in dLNs was recorded over time. Shown are the means and SD from one of two independent experiments. k counts, 1000 counts. (B and C) BALB/c mice (n=5 per group, 10 dLNs) were immunized with fluorescent MD39 or MD39-8mer (with the equivalent of 5 mg of trimer in each group) and adjuvant. FDCs were labeled in situ with anti-CD35 antibody, excised dLNs were cleared and (B) imaged by confocal microscopy, and (C) colocalization of antigen with follicles was quantified by the percentage of MD39 signal within follicles and by the percentage of follicular area that contained MD39. Shown are the means and SD from one of three independent experiments. Lipos, liposomes. (D to F) BALB/c mice (n=5 to 9 per group, 10 to 18 dLNs) were immunized with fluorescent eOD monomer or eOD-60mer (with the equivalent of 2 mg of eOD in each group) and adjuvant. (D) FDCs or GCs were labeled in situ with anti-CD35 or anti-CD157, respectively, and excised dLNs were cleared and imaged by confocal microscopy. In images from eOD-immunized mice, eOD brightness was increased to allow for visualization. (E) Colocalization of antigen with follicles was quantified by the percentage of eOD signal within follicles and by the percentage of follicular area that contained eOD. Shown are the means and SD from one of three independent experiments. (F) dLNs were cut into 100-mm-thick slices and stained with anti-B220 and anti-Ki67, and individual follicles were imaged by confocal microscopy. *P<0.05, **P<0.01, determined by a one-way ANOVA followed by Tukey's multiple comparisons test. IR dye-tagged antigen-trafficking analysis included comparisons to unimmunized LN controls at each time point.
Figure 2D:
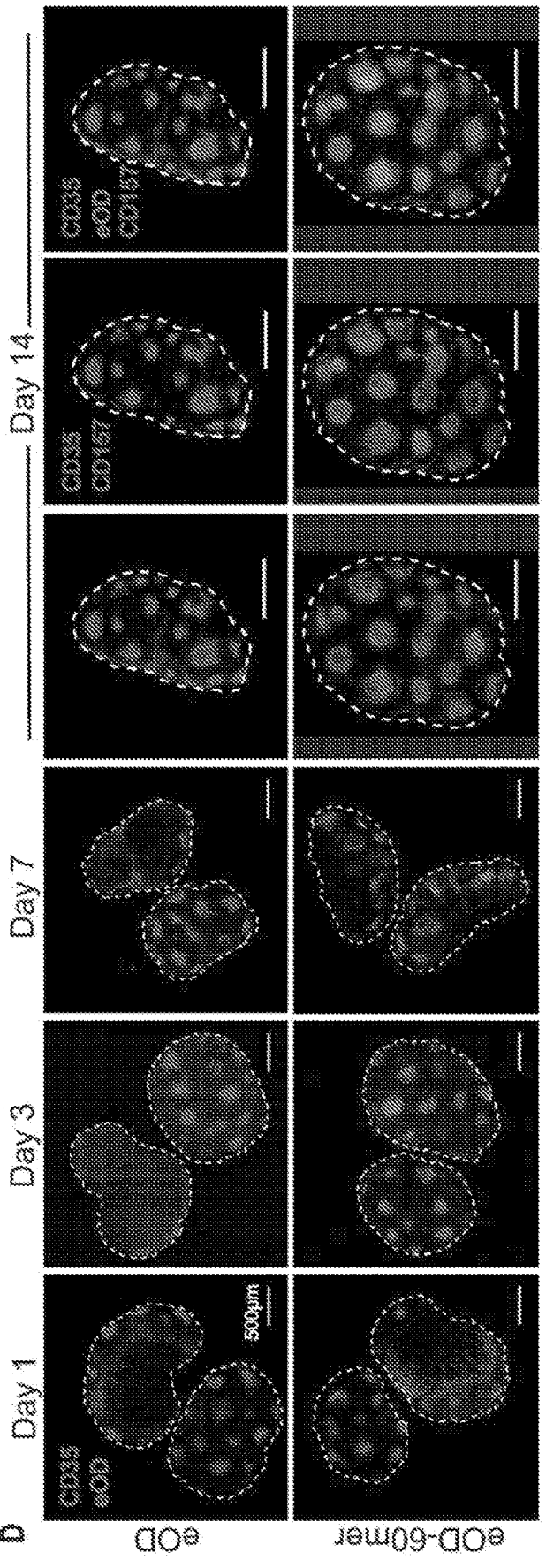
Figures 2E, 2F:
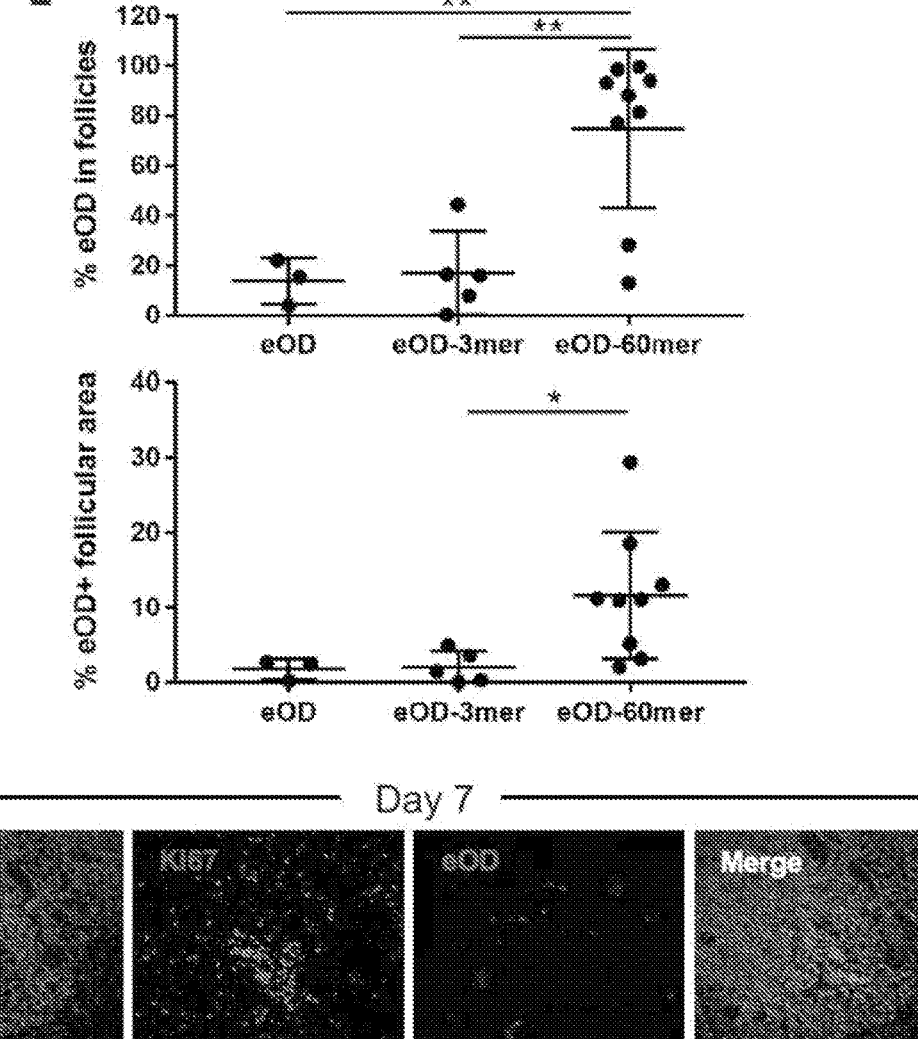
Figures 7A, 7B, 7C, 7D, 7E, 7F:
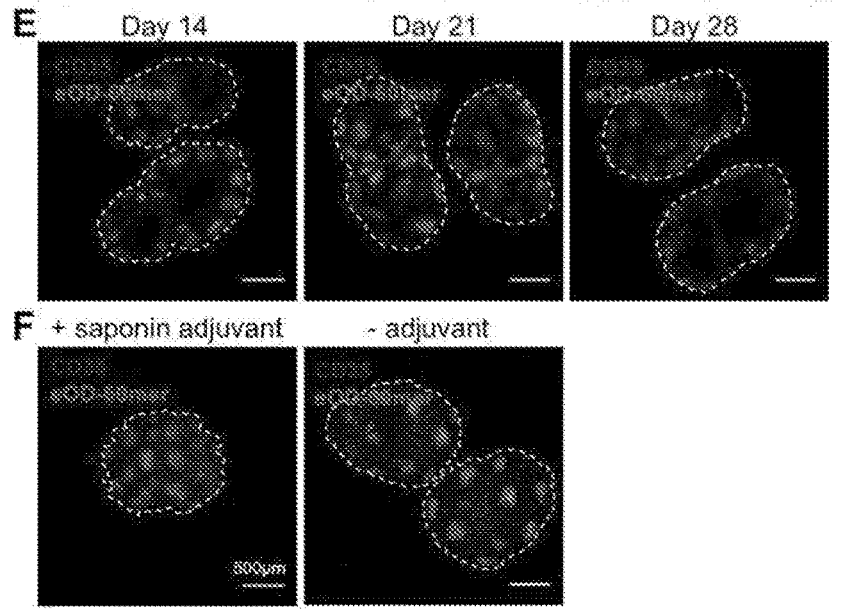
FIG. 7A-7K. Lymph node localization of nanoparticle immunogens. (A) Balb/c mice (n=5/group, 10 dLNs) were immunized with 5 μg fluorescent MD39 displayed on liposomes, dLNs were recovered after 3 and 7 days, cleared, and imaged by confocal microscopy. (B) Balb/c mice (n=3 animals/group, 6 LNs) were immunized with 2 μg fluorescent eOD monomer+adjuvant, and eOD colocalization with CD169⁺ or SIGN-R1⁺ macrophages on day 7 was evaluated by immunohistochemistry (100 um scale bar). (C, D) Balb/c mice (n=3 animals/group, 6 LNs) were immunized with (C) 2 μg unlabeled eOD monomer+adjuvant or (D) equivalent moles of eOD-60mer+adjuvant, LNs were collected at day 7, fixed, sectioned, and stained with anti-CD35 and fluorescent VRC01 to detect eOD, followed by confocal microscopy. (E) Balb/c mice (n=3 animals/group, 6 LNs) were immunized with 3.7 μg fluorescent eOD-60mer (equivalent to 2 of eOD) and sacrificed at serial timepoints as indicated; LNs were cleared and imaged by confocal microscopy. (F) Balb/c mice (n=5/group, 10 dLNs) were immunized with 3.7 μg fluorescent eOD-60mer in the absence or presence of adjuvant, dLNs were recovered after 7 days, cleared, and imaged by confocal microscopy. (G-J) Balb/c mice (n=5/ group, 10 dLNs) were immunized with either (G) 2 μg eOD-3mer, (H) 2 ug blank lumazine synthase core nanoparticles, (I) 6.4 μg MD39-8mer (equivalent to 5 μg trimer, or (J) 5 μg MD39 displayed on liposomes and adjuvant. FDCs and germinal centers were labeled in situ with anti-CD35 or anti-CD157, respectively. dLNs were recovered after 7 days, cleared, and imaged by confocal microscopy. (K) High magnification images of individual B cell germinal centers from mice immunized with MD39 and MD39-8mer.
Figures 7G, 7H, 7I, 7J, 7K:
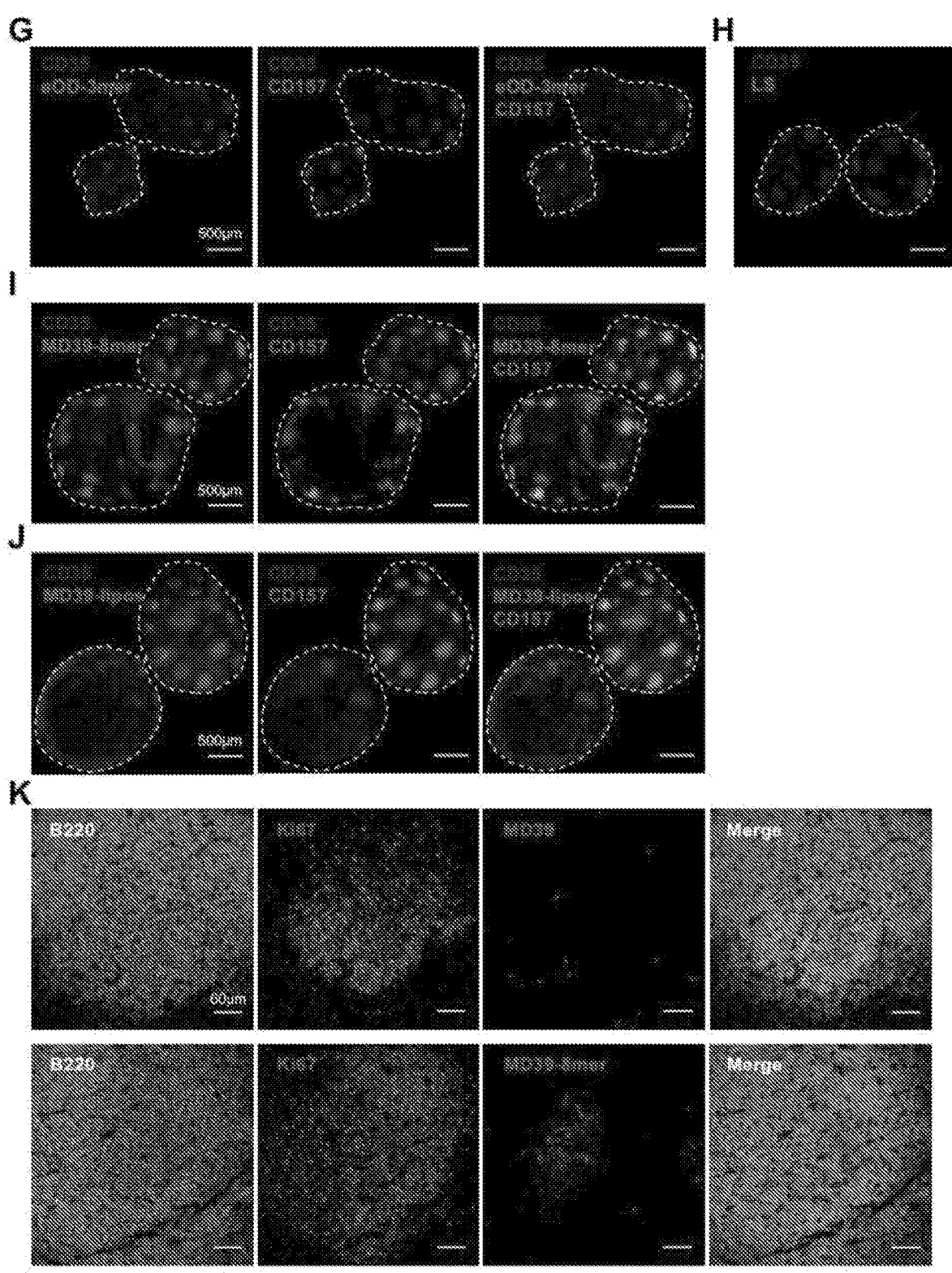

To understand the differences in immune responses induced by HIV antigen nanoparticles versus soluble monomers, the lymphatic trafficking and tissue localization of each HIV immunogen was examined. Whole-tissue fluorescence measurements of infrared (IR) dye-labeled immunogens in draining LNs (dLNs) showed higher total accumulation of both nanoparticle formulations than of monomeric forms in dLNs at 3 days postimmunization (FIG. 2A). However, confocal imaging of cleared whole dLNs revealed that soluble MD39 accumulated primarily in the sub-capsular sinus and medullary areas, whereas MD39-8mer was observed to begin concentrating within follicles by day 3 and was strongly colocalized with follicular dendritic cells (FDCs) by day 7 (FIGS. 2, B and C). Liposomes (~95 nm in diameter) surface-conjugated with densely packed MD39 also exhibited FDC accumulation over 7 days postimmunization, though with a lower efficiency than the smaller ferritin-based nano-particles, suggesting that FDC targeting is independent of the nature of the nanoparticle core (FIG. 2C and FIG. 7A) (8). Trafficking of the eOD monomer versus eOD-60mer was even more distinct: Whereas the eOD monomer showed low levels of accumulation in dLNs over a 14-day time course and colocalized primarily with SIGN-R1$^+$ macrophages, as reported previously for other gp120 antigens (19), eOD-60mer was already beginning to colocalize with FDCs after 24 hours (FIG. 2D and FIGS. 7, B and C). By day 7, eOD nanoparticles were almost exclusively localized within the FDC network and persisted there for ~4 weeks (FIGS. 2, D and E, and FIGS. 7, D and E); FDC localization occurred in the presence or absence of coadministered adjuvant, albeit with lower overall accumulation in the absence of adjuvant (FIG. 7F). Targeting of FDCs required high antigen valency, as eOD trimers failed to show follicular localization similar to that of the eOD monomer (FIG. 2E and FIG. 7G). Bare lumazine synthase nanoparticles lacking eOD also did not traffic to FDC networks (FIG. 7H). Costaining to identify GCs showed that both the monomer and eOD-60mer initiated GCs (FIG. 2F), but much higher levels of eOD-60mer were localized in GCs, aligning with FDCs in the light zone (FIGS. 2, D and F). MD39-8mers and MD39 conjugated to liposomes exhibited a similar pattern of concentration within GCs (FIG. 7, I to K).

Figures 3A, 3B, 3C, 3D, 3E:
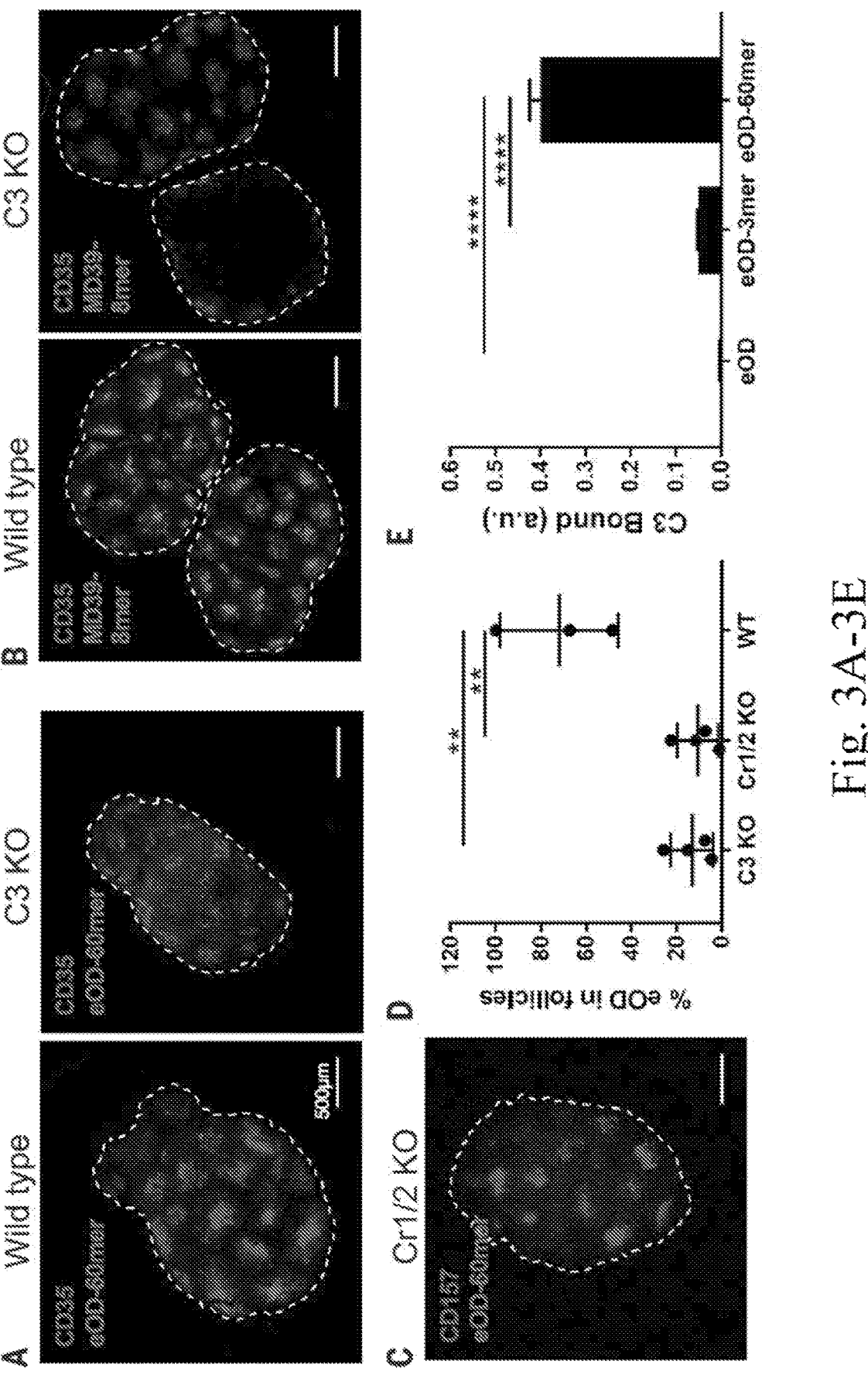
FIG. 3A-3E. Complement and complement receptor are required for follicular targeting of nanoparticle immunogens. (A to D) WT C57BL/6, C3 KO, or Cr1/2 KO mice (n=4 mice per group, 8 dLNs) were immunized with 3.7 mg of fluorescent eOD-60mer (equivalent to 2 mg of eOD) or 6.4 mg of MD39-8mer (equivalent to 5 mg of trimer) and adjuvant. dLNs were recovered after 7 days, cleared, and imaged by confocal microscopy. Antigen localization was imaged in [(A) and (B)] WT and C3 KO or (C) Cr1/2 KO animal LNs for [(A) and (C)] eOD-60mer or (B) MD39-8mer, and (D) eOD localization in follicles in WT versus KO mice was quantified by the percentage of eOD signal within follicles and by the percentage of follicular area that contained eOD. Shown are the means and SD from one of two independent experiments. (E) WT mouse serum was added to ELISA plates coated with the eOD monomer, eOD-3mer, or eOD-60mer, and deposited C3 was detected by ELISA. Shown are the means and SD from one of four independent experiments. a.u., absorbance units. P<0.01, **P<0.0001, determined by a one-way ANOVA followed by Tukey's multiple comparisons test.

Targeting to FDCs and GCs is not a generic property of nanoparticles in naïve animals, as many vaccine studies have shown particles of diverse sizes and material compositions localizing in a manner suggesting exclusion rather than enrichment in B cell follicles (20-23). By contrast, immune complexes (ICs) have been reported to elicit a similar type of antigen delivery to FDCs (24-26). IC trafficking to FDCs is mediated by the relay of complexes from subcapsular sinus macrophages to migrating B cells, which in turn transfer antigen to FDCs, in a complement- and complement receptor-dependent manner (24-26). To determine whether complement is also involved in the recognition of envelope nanoparticles and to test whether nanoparticle trafficking is mediated by interactions with complement receptors, mice lacking the C3 component of the complement system [C3 knockout (KO) mice] and mice lacking complement receptors (Crl/2 KO mice) were immunized with eOD-60mer or MD39-8mer. As shown in FIGS. 3, A and B, both nanoparticles were strongly localized to the FDC network in wild-type (WT) mice at day 7, but only low levels of antigen were detected in C3 KO dLNs, with a diffuse distribution. Nanoparticle trafficking to FDCs was also abrogated in Crl/2 KO animals (FIGS. 3, C and D). Consistent with these findings, in vitro addition of normal serum to plate-immobilized eOD-60mer, but not the eOD monomer or trimer, led to substantial deposition of C3 as detected by ELISA (FIG. 3E). These data suggest that opsonization of nanoparticle antigens by complement is required for rapid trafficking to FDCs and that this trafficking is complement receptor dependent.

Figures 4A, 4B, 4C, 4D, 4E, 4F:
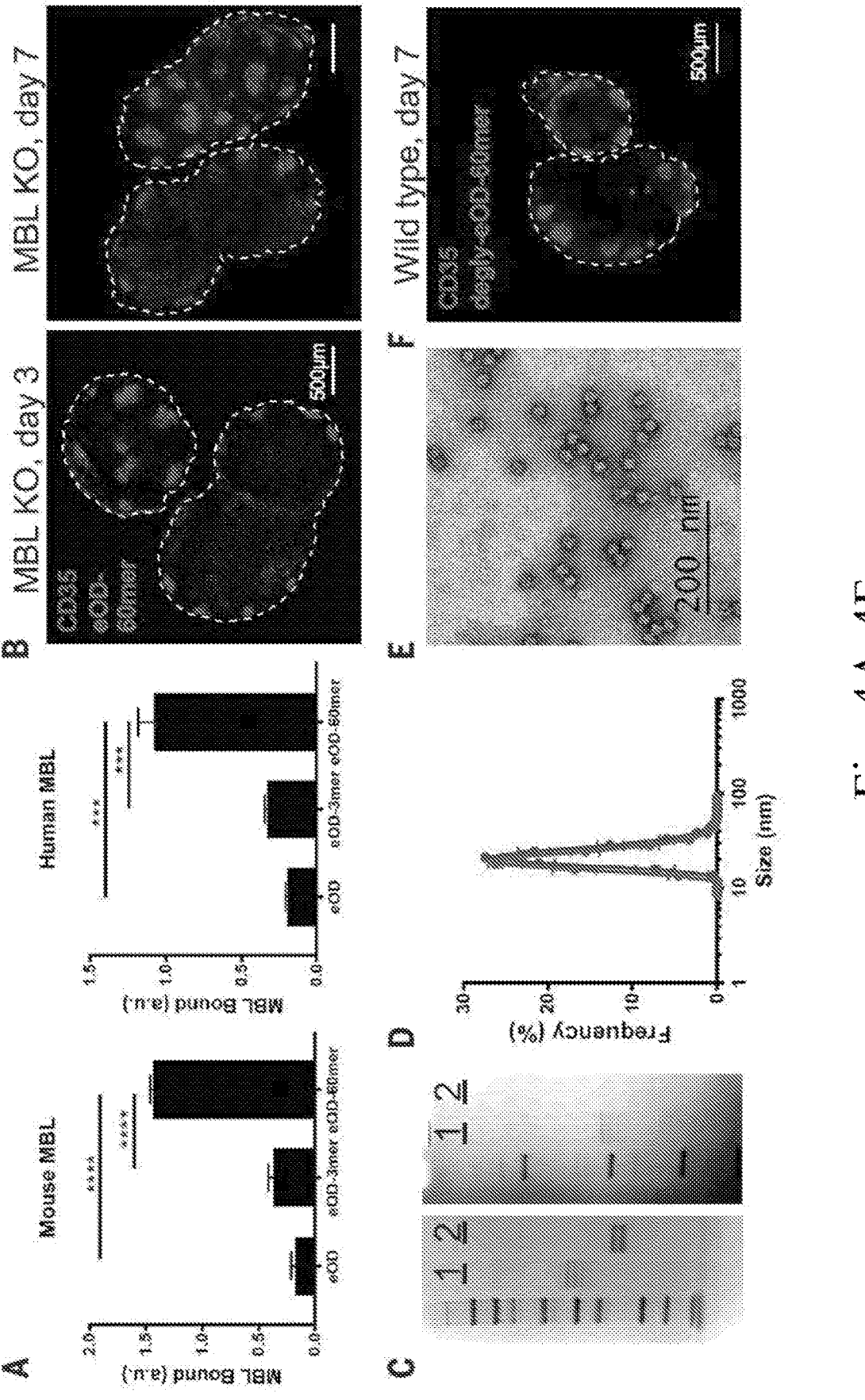
FIG. 4A-4M. MBL-mediated innate recognition and follicular targeting amplifies humoral responses to envelope nanoparticle immunogens. Mouse MBL (200 ng/ml) or human MBL (7.5 mg/ml) was added to ELISA plates coated with the eOD monomer, eOD-3mer, or eOD-60mer, and bound MBL was detected by ELISA. Shown are the means and SD from one of four independent experiments. MBL KO mice (n=3 mice per group, 6 dLNs) were immunized with 3.7 mg of fluorescent eOD-60mer (equivalent to 2 mg of eOD) and adjuvant. Excised dLNs were cleared and imaged by confocal microscopy. eOD brightness was increased to allow for visualization. (C) Unmodified eOD-60mer (1) and eOD-60mer deglycosylated by PNGase F treatment (2) were analyzed via SDS-polyacrylamide gel electrophoresis for changes in subunit size and glycan content. (Left) Nonspecific protein stain. (Right) Glycoprotein stain. (D) Unmodified (red) and deglycosylated (blue) eOD-60mer hydrodynamic radii were evaluated by dynamic light scattering. (E) Cryo-TEM of deglycosylated eOD-60mer. C57BL/6 mice (n=5 per group, 10 dLNs) were immunized with 3.7 mg of fluorescent deglycosylated (degly) eOD-60mer and adjuvant. Excised dLNs were cleared and imaged by confocal microscopy. C57BL/6 mice (n=5 per group) were immunized with 3.7 mg of eOD-60mer (red) or deglycosylated eOD-60mer (blue) and adjuvant. Serum eOD-specific IgG titers from individual mice were analyzed over time by ELISA. Shown are the means with 95% CIs from one of two independent experiments. (H to L) C57BL/6 mice (red) or MBL KO mice (blue) (n=5 per group) were immunized with 3.7 mg of eOD-60mer and adjuvant. Absolute (abs.) numbers of GC $T_{fh}$ cells and (I) GC B cells from individual mice were analyzed at day 7. Shown are the means and SD. (J) eOD-specific IgG titers from individual mice were analyzed over time by ELISA. Shown are the means and 95% CIs. (K) Isotype-specific midpoint titers were analyzed 1 month postimmunization. Shown are the means and SD. (L) Bone marrow eOD-specific antibody-secreting cells (ASCs) were quantified by enzyme-linked immunospot assay at 8 weeks postimmunization. Data show the means and SD. (M) C57BL/6 mice (n=3 animals per group) were immunized with 5 mg of fluorescent bare ferritin nanoparticles lacking glycans or 5 mg of ferritin particles conjugated with trimannose moieties (~96 trimannose groups per particle), together with adjuvant. LNs were excised 3 days later, sectioned, and imaged by confocal microscopy. *P<0.05, P<0.01, *P<0.001, ****P <0.0001, determined by either a one-way ANOVA followed by Tukey's multiple comparisons test or a Mann-Whitney test (for serum titer analysis only).
Figure 8:
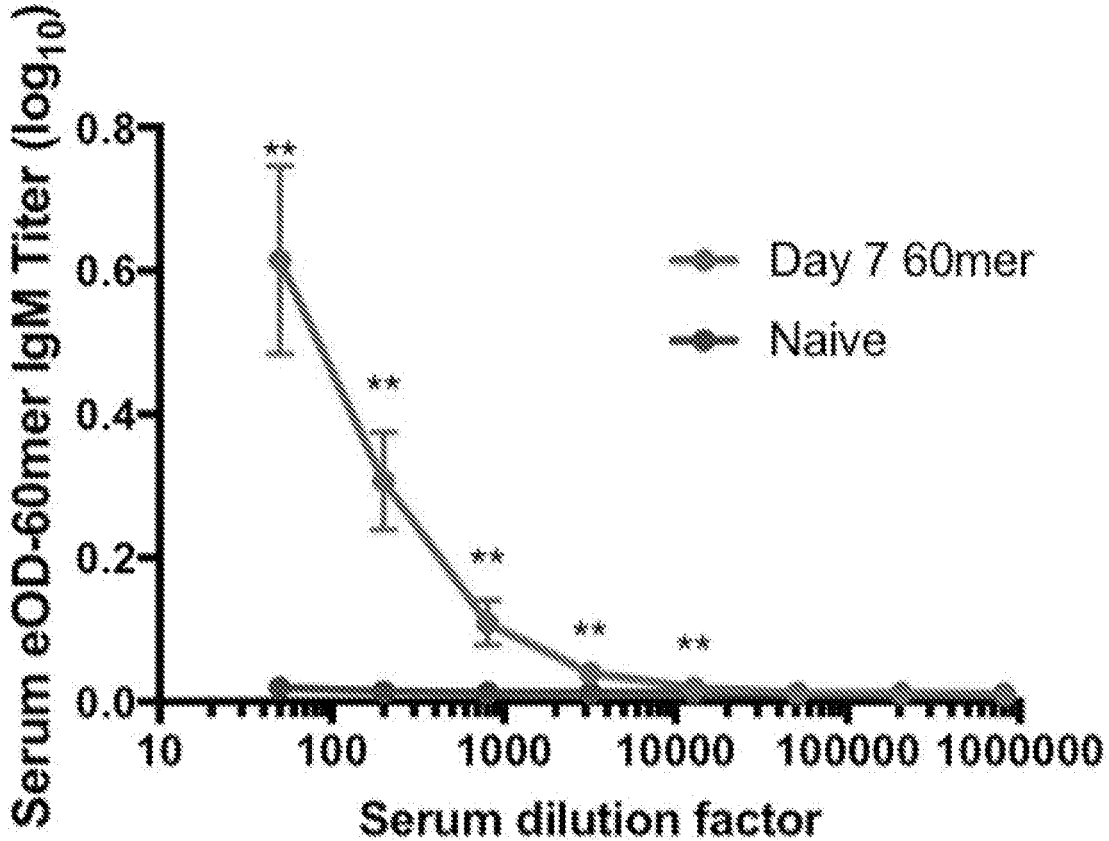
FIG. 8. Serum IgM from naïve animals does not recognize eOD-60mer. Plates were coated with eOD-60mer and incubated with mouse sera from unimmunized animals and sera from animals one week post immunization with eOD-60mer. IgM binding was detected using a primary rat anti-mouse IgM antibody followed by secondary detection with a rabbit anti-rat IgG-HRP antibody conjugate. **p<0.01, determined using a t test on each dilution. Shown are mean and SD from one of two independent experiments.
Figure 9:
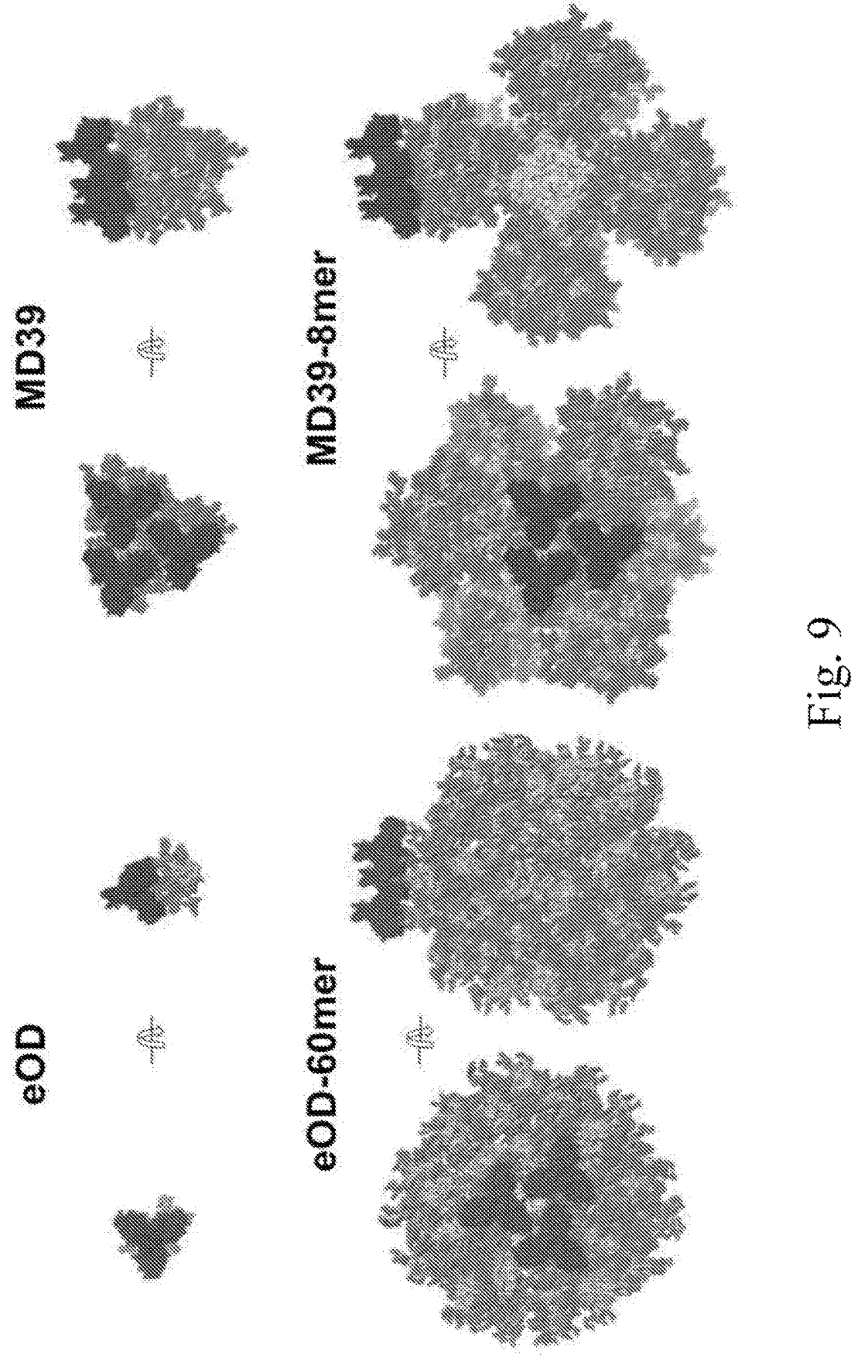
FIG. 9. Structural models of trimeric stalks of MBL carbohydrate binding domains interacting with the glycans of eOD or MD39 antigens. The crystal structure of the trimeric carbohydrate binding domain (CBD) from one stalk of mannose binding lectin (PDB: 1HUP) was oriented either alone or as a hypothetical arrangement of three stalks onto structural models of eOD, eOD-60mer, MD39, or MD39-8mer, to illustrate at scale potential interactions between one trimeric stalk or three trimeric stalks of MBL and the immunogens. The modeling suggested that the small size of eOD monomer prevents it from interacting with more than one stalk, whereas the MD39 trimer could potentially interact with several stalks (three are shown) and both eOD-60mer and MD39-8mer could potentially interact with an even larger number of trimeric stalks (only three are shown).
Figures 10A, 10B:
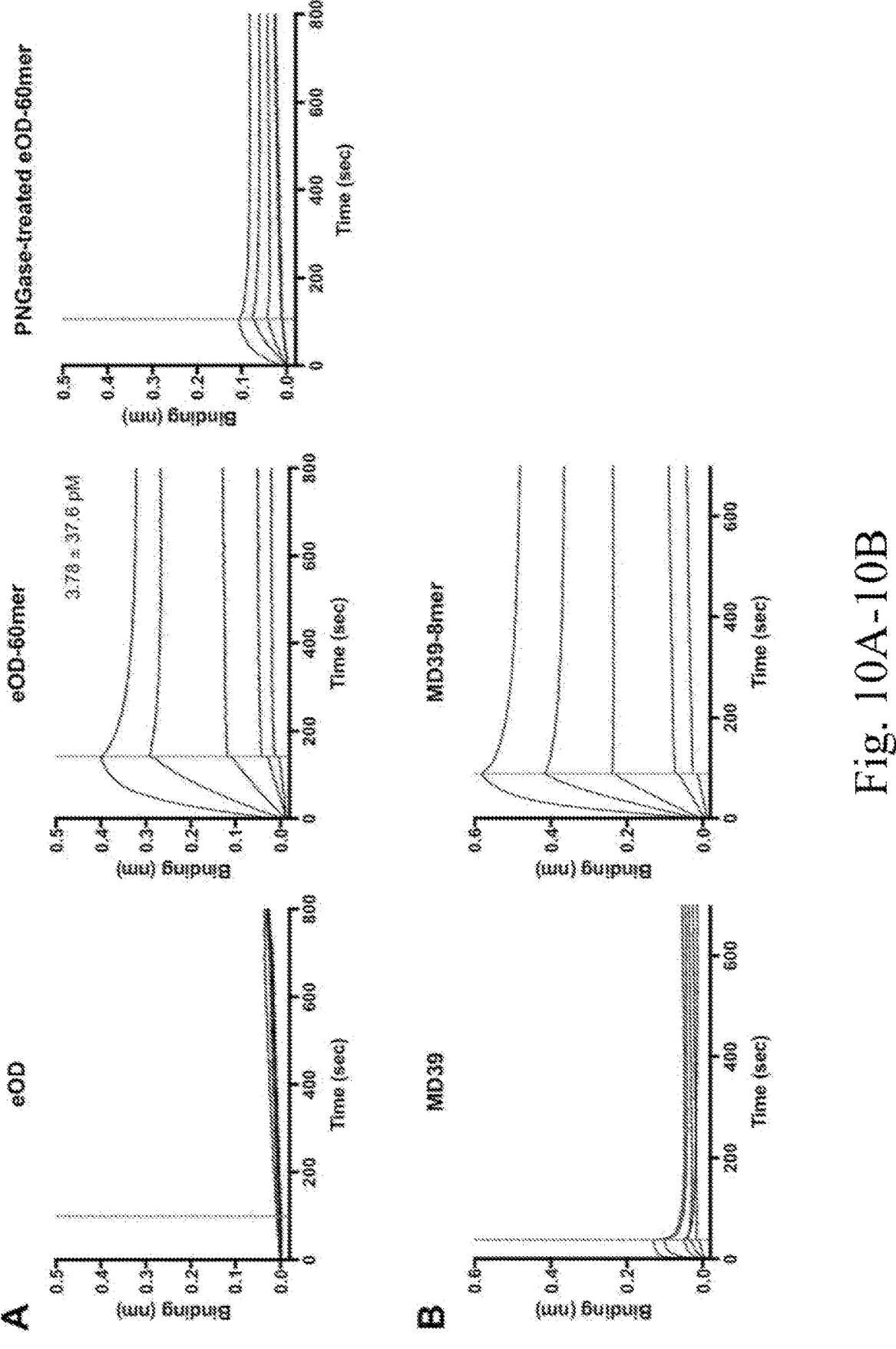
FIG. 10A-10B. MBL binds with high apparent affinity to nanoparticle eOD and MD39 immunogens. (A) Biolayer interferometry binding and unbinding curves for eOD, eOD-60mer, and PNGase-deglycosylated eOD-60mer binding to immobilized recombinant mouse MBL. The apparent affinity (KD) calculated for MBL binding to 60mer is shown on the graph. (B) Biolayer interferometry binding/unbinding curves for MD39 trimer or MD39-8mer to immobilized recombinant mouse MBL.

The mechanism of complement fixation by the nanoparticle immunogens was investigated. IgM from naïve animals did not bind eOD-60mer by ELISA (FIG. 8), suggesting that natural IgM is not involved. The lectin-mediated pathway activates complement in bacterial immunity; here, mannosebinding lectin (MBL) binds to glycosylated microbes and activates complement via MBL-associated serine proteases (27). MBL is a large macromolecular complex composed of multimers of trimeric lectin stalks, which achieve high-avidity binding to pathogens through multivalent engagement with large patches of dense sugars (27-29). Structural studies have shown that the three carbohydrate binding domains (CBDs) at the end of each stalk in the MBL multimer are arranged in a triangular configuration, separated by 4.5 nm (30); the distance between each stalk of MBL multimers is poorly defined but expected to be of similar order or larger (31). Each CBD recognizes mannose and other sugars with a very weak affinity of $K_d$ (dissociation constant) ~$10^{-3}$M, but stable binding to larger patches of glycans is thought to be achieved by the avidity effect of engaging multiple trimeric stalks of MBL multimers. These considerations suggest that MBL will be unable to bind multiple stalks to an eOD monomer (diameter, 7.5 nm) and may be capable of engaging only a few stalks on MD39 trimers (diameter, 15 nm) (FIG. 9). In agreement with these arguments, in an ELISA-type assay murine and human MBLs bound to immobilized eOD-60mer but exhibited only weak recognition of eOD-3mer and the eOD monomer (FIG. 4A). Biolayer interferometry measurements of eOD-60mer binding to immobilized MBL revealed an apparent affinity of ~4 pM, whereas binding by the eOD monomer was essentially undetectable; similarly, the nanoparticle MD39-8mer showed avid binding by MBL, whereas binding to the MD39 monomer was low (FIGS. 10, A and B).

Figures 11A, 11B, 11C:
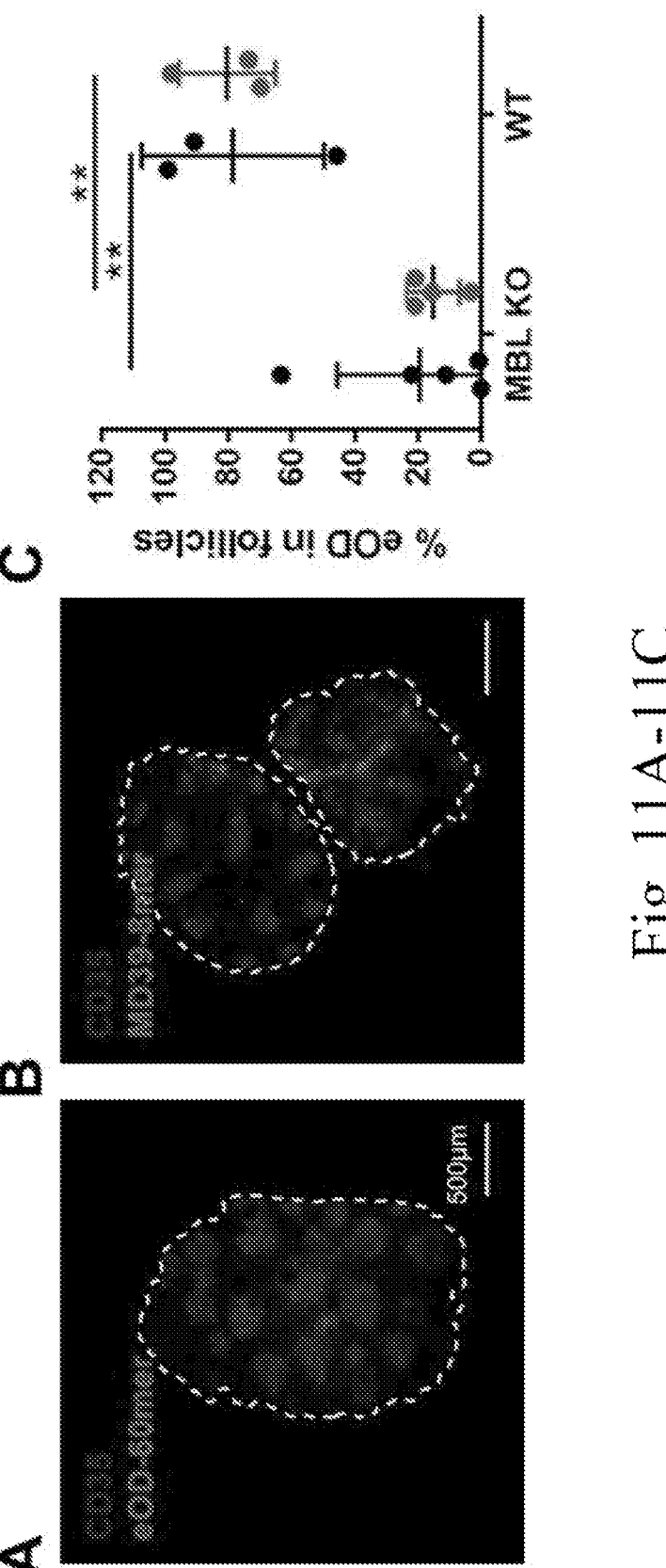
FIG. 11A-11C. Additional trafficking data in MBL KO animals. (A-B) MBL KO mice (n=3/group, 6 dLNs) were immunized with (A) 3.7 μg florescent eOD-60mer (equivalent to 2 μg eOD) or (B) 6.4 μg fluorescent MD39-8mer (equivalent to 5 μg trimer), dLNs were recovered after 7 days, cleared, and imaged by confocal microscopy. Nanoparticle brightness was increased to allow for visualization. (C) eOD localization in follicles in WT vs. knockout mice was quantified after 3 (black) and 7 (red) days. Shown are mean and SD.
Figure 12:
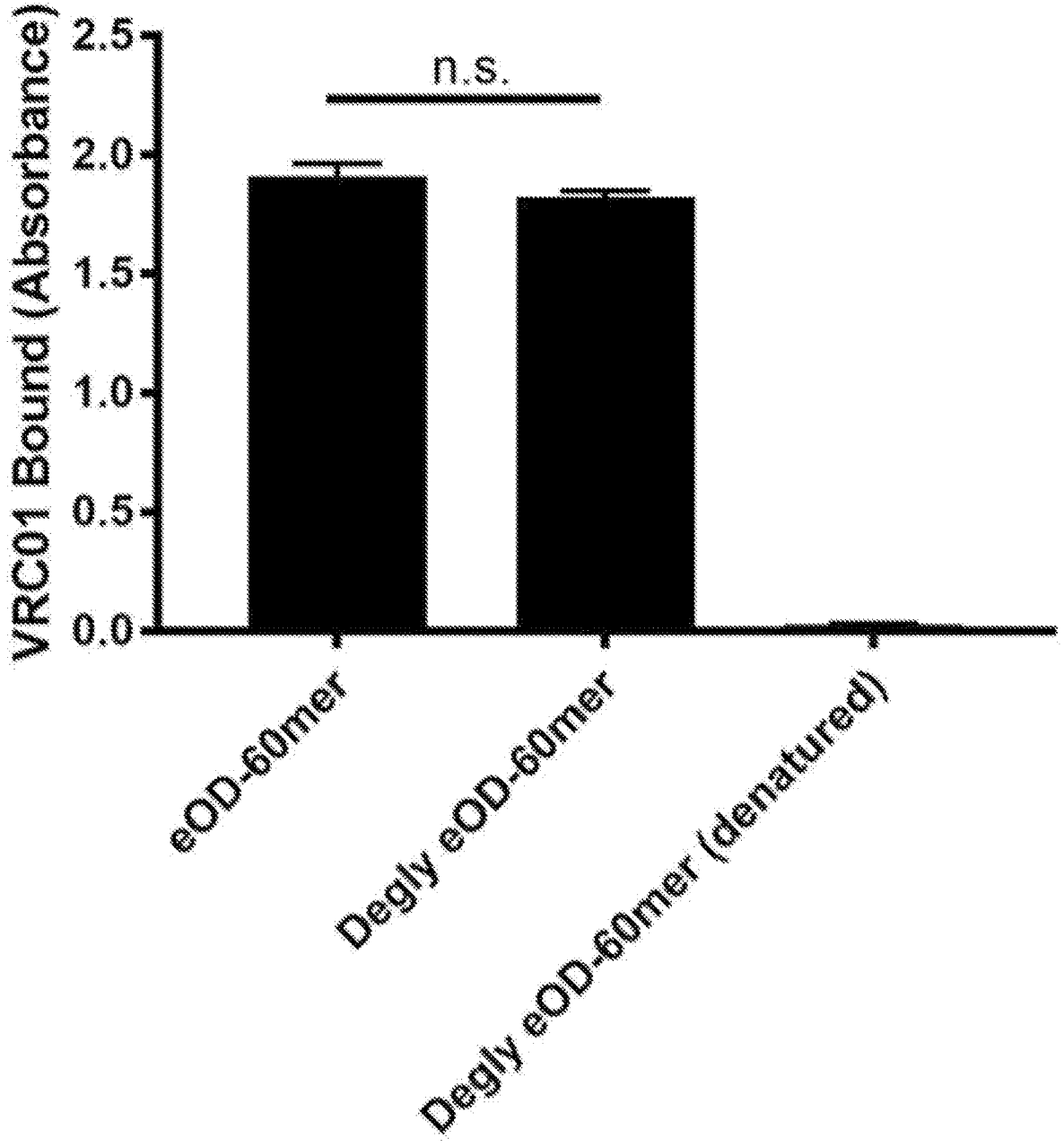
FIG. 12. The CD4 binding site antibody VRC01 retains recognition of deglycosylated eOD-60mer. eOD-60mer was deglycosylated (degly eOD-60mer) under non-denaturing conditions and denaturing conditions. Plates were coated in 2 μg/ml eOD-60mer, degly eOD-60mer, and denatured degly eOD-60mer and incubated with 1 μg/ml mouse VRC01. VRC01 binding was then detected with a secondary goat anti-mouse IgG-HRP antibody conjugate. Analyzed using t test on direct comparisons. Shown are mean and SD.
Figures 13A, 13B:
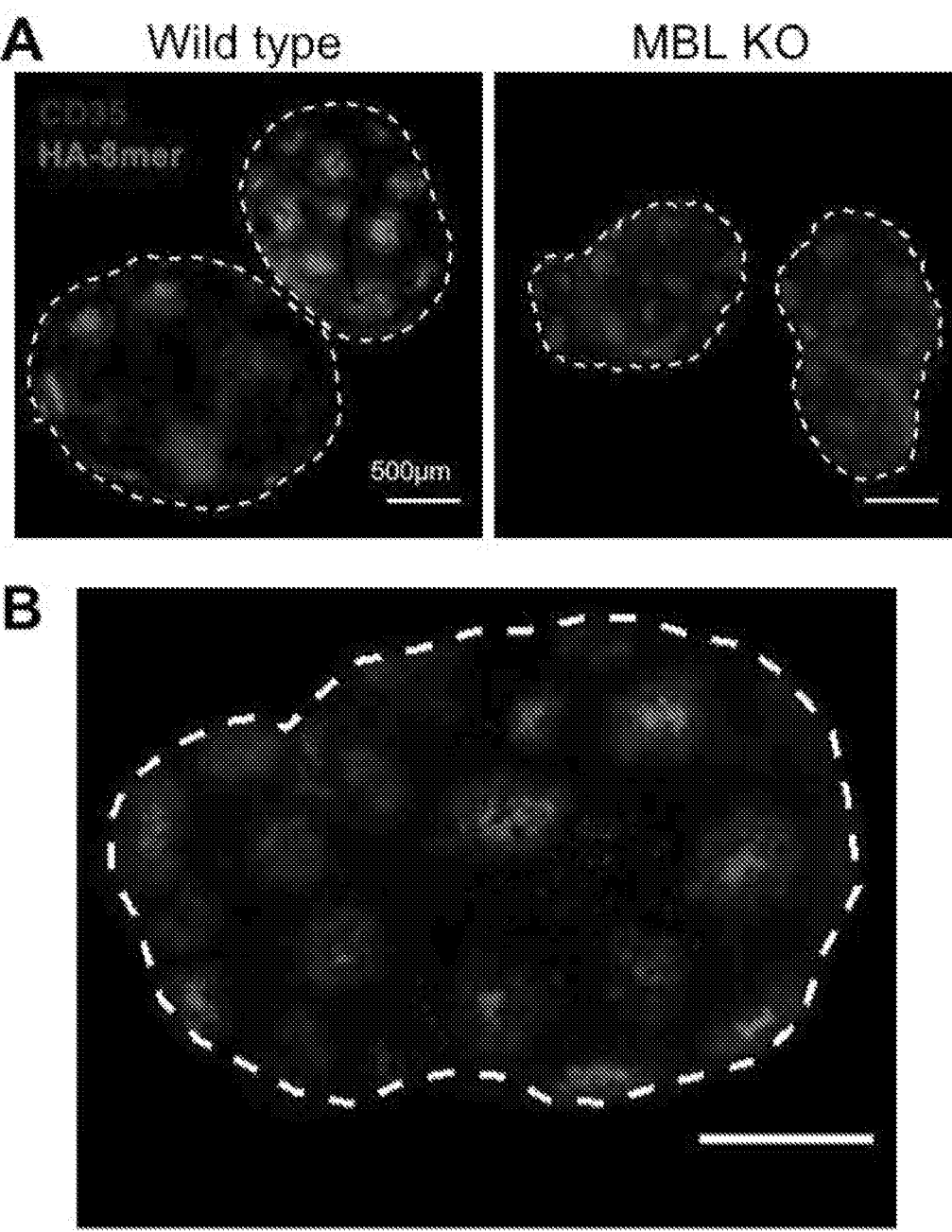
FIG. 13A-13B. Influenza HA-8mer and eOD-60mer bearing predominantly complex glycans also exhibit follicular targeting. (A, B) C57BL/6 or MBL KO mice (n=4/group, 8 dLNs) were immunized with 2 μg HA-8mer or eOD-60mer prepared in 293F cells. dLNs were recovered after 7 days, cleared, and imaged by confocal microscopy. Shown is (A) the trafficking of HA-8mer and (B) eOD-60mer prepared in 293F cells, bearing predominantly complex glycans. (Scale bars 500 μm).

To evaluate whether is involved in trafficking of nanoparticles to FDCs in vivo, MBL KO mice were immunized with eOD-60mer or MD39-8mer. dLiNs contained low levels of antigen with no accumulation on the FDC network (FIG. 4B and FIG. 11, A to C). To evaluate whether FDC localization was immunogen glycan-dependent, eOD-60mer was deglycosylated with peptide N-glycosidase F (PNGase F) and confirmed by light scattering, TEM, and ELBA analyses that the enzyme-treated protein retained its self-assembled particle structure and presentation of the key CD4 binding site epitope (FIG. 4,C to E, and FIG. 12). MBL bound at only low levels to deglycosyllated eOD-60mer in vitro (FIG. 10A), and deglycosylated particles exhibited low accumulation in LNs in WT mice, with no FDC localization (FIG. 4F). These data imply that dense arrays of glycans trigger MBL-mediated innate immune recognition of nanoparticles. To assess the generality of this concept, we assessed trafficking of another highly glycosylated nanoparticle immunogen, influenza hemagglutinin-ferritin 8-mer particles (HA-8mers) (4), which were also targeted to the FDC network in WT mice but not MBL KO mice (FIG. 13A).

Figure 14:
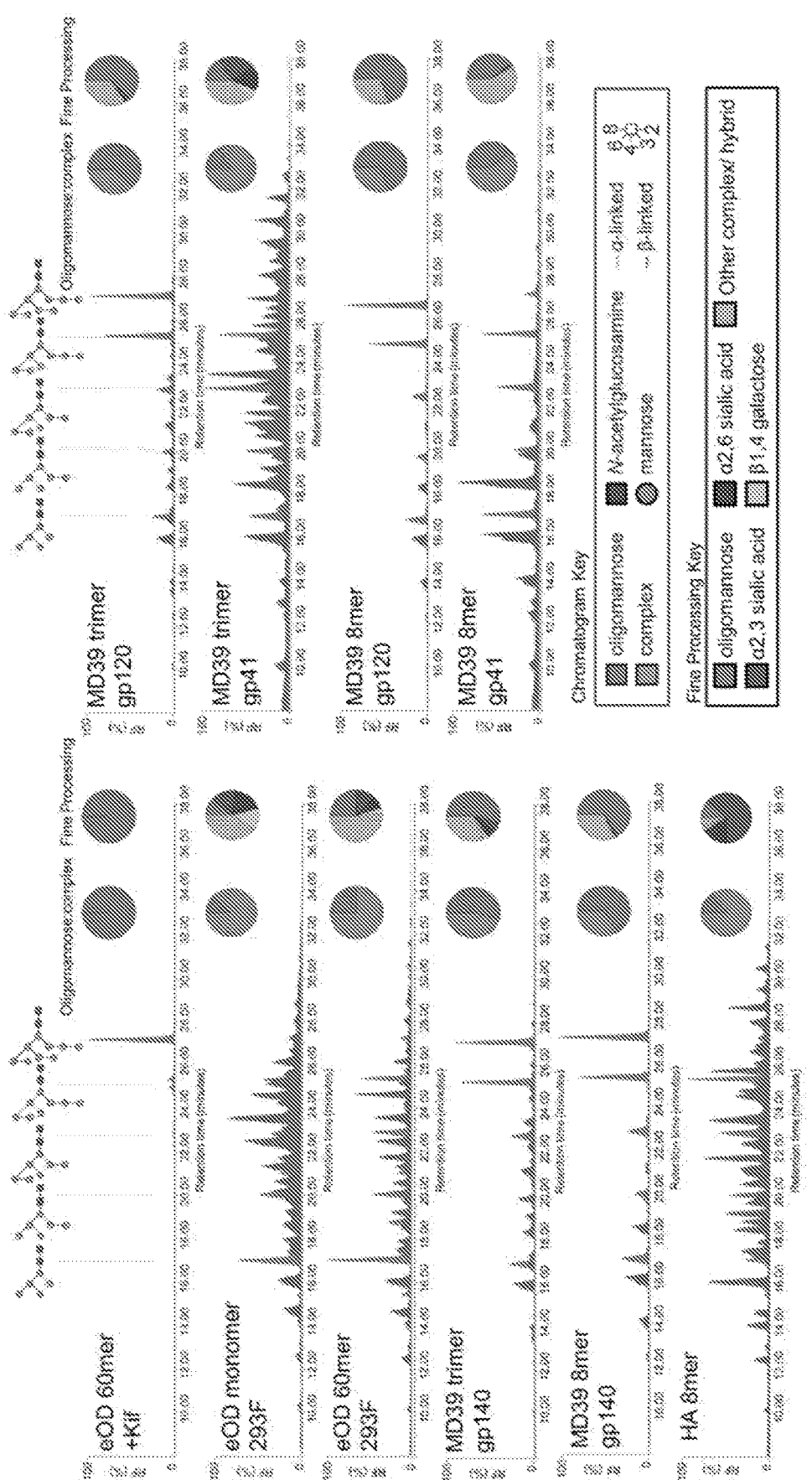
FIG. 14. Global glycan analysis of Env-based nanoparticles and unconjugated counterparts using ultra-high performance liquid chromatography (UPLC). UPLC chromatograms of N-glycans from eOD 60mer+Kif, eOD monomer.

To obtain insight into how the composition and density of glycans regulate MBL recognition of nanoparticles, the glycan profiles of each of the immunogens were characterized. eOD-60mer was typically prepared in the presence of kifunensine, such that its glycans were almost completely oligomannose (FIG. 14). By contrast, the eOD monomer (typically prepared in 293F cells) contained predominantly complex-type glycans (FIG. 14).

TABLE 1

|  | eOD monomer | eOD 60mer | MD39 trimer gp140 | MD39 8mer gp140 | HA 8mer |
| --- | --- | --- | --- | --- | --- |
| Total oligomannose | 11.72% | 24.72% | 54.27% | 66.78% | 14.75% |
| M9 | 0.00% | 0.75% | 19.31% | 25.13% | 0.00% |
| M8 | 0.00% | 4.98% | 18.15% | 19.46% | 5.77% |
| M7 | 2.61% | 5.41% | 6.99% | 7.78% | 5.44% |
| M6 | 2.58% | 4.40% | 4.05% | 4.68% | 2.35% |
| M5 | 6.52% | 9.18% | 5.77% | 9.73% | 1.19% |
| Total complex/hybrid | 88.28% | 75.28% | 45.73% | 33.22% | 85.25% |
| α2,3 sialic | 14.87% | 11.77% | 5.78% | 0.49% | 21.89% |
| α2,6 sialic | 19.03% | 8.41% | 5.87% | 0.52% | 2.73% |
| β1,4 gal | 14.25% | 3.70% | 2.80% | 0.85% | 8.52% |
| Other complex/hybrid | 40.13% | 51.40% | 31.28% | 31.36% | 52.11% |

|  | eOD 60mer + Kif | MD39 trimer gp120 | MD39 trimer gp41 | MD39 8mer gp120 | MD39 8mer gp41 |
| --- | --- | --- | --- | --- | --- |
| Total oligomannose | 100.00% | 63.18% | 17.17% | 69.90% | 39.76% |
| M9 | 84.64% | 25.19% | 0.00% | 28.22% | 2.35% |
| M8 | 12.68% | 21.59% | 3.98% | 20.30% | 9.84% |
| M7 | 2.68% | 6.69% | 6.50% | 7.27% | 9.29% |
| M6 | 0.00% | 3.86% | 2.93% | 4.80% | 6.35% |
| M5 | 0.00% | 5.85% | 3.77% | 9.30% | 11.93% |
| Total complex/hybrid | 0.00% | 36.82% | 82.83% | 30.10% | 60.24% |
| α2,3 sialic | 0.00% | 2.79% | 23.76% | 0.22% | 0.92% |
| α2,6 sialic | 0.00% | 0.80% | 16.06% | 0.00% | 0.54% |
| β1,4 gal | 0.00% | 2.51% | 6.13% | 0.00% | 0.74% |
| Other complex/hybrid | 0.00% | 30.72% | 36.88% | 29.88% | 58.04% |

To assess whether this difference in glycan composition affected in vivo antigen trafficking, eOD-60mer was prepared in 293F cells, which contained predominantly complex glycans mirroring the eOD monomer (FIG. 14). These eOD-60mer nanoparticles trafficked to FDCs in a manner identical to that of the eOD-60mer bearing only oligomannose glycans (FIG. 1313), suggesting that small levels of oligomannose glycans are sufficient to trigger MBL-mediated trafficking to follicles. In support of this argument, MD39-8mers and HA-8mers exhibited an ~50/50 complex/oligomannose ratio and a predominantly complex glycan profile, respectively, but the two nanoparticle immunogens showed similar FDC localization patterns in vivo. Similar immunogen trafficking patterns elicited by these distinct glycan profiles are consistent with the ability of MBL to bind to both complex and simple sugars.

Figures 4G, 4H, 4I, 4J, 4K, 4L:
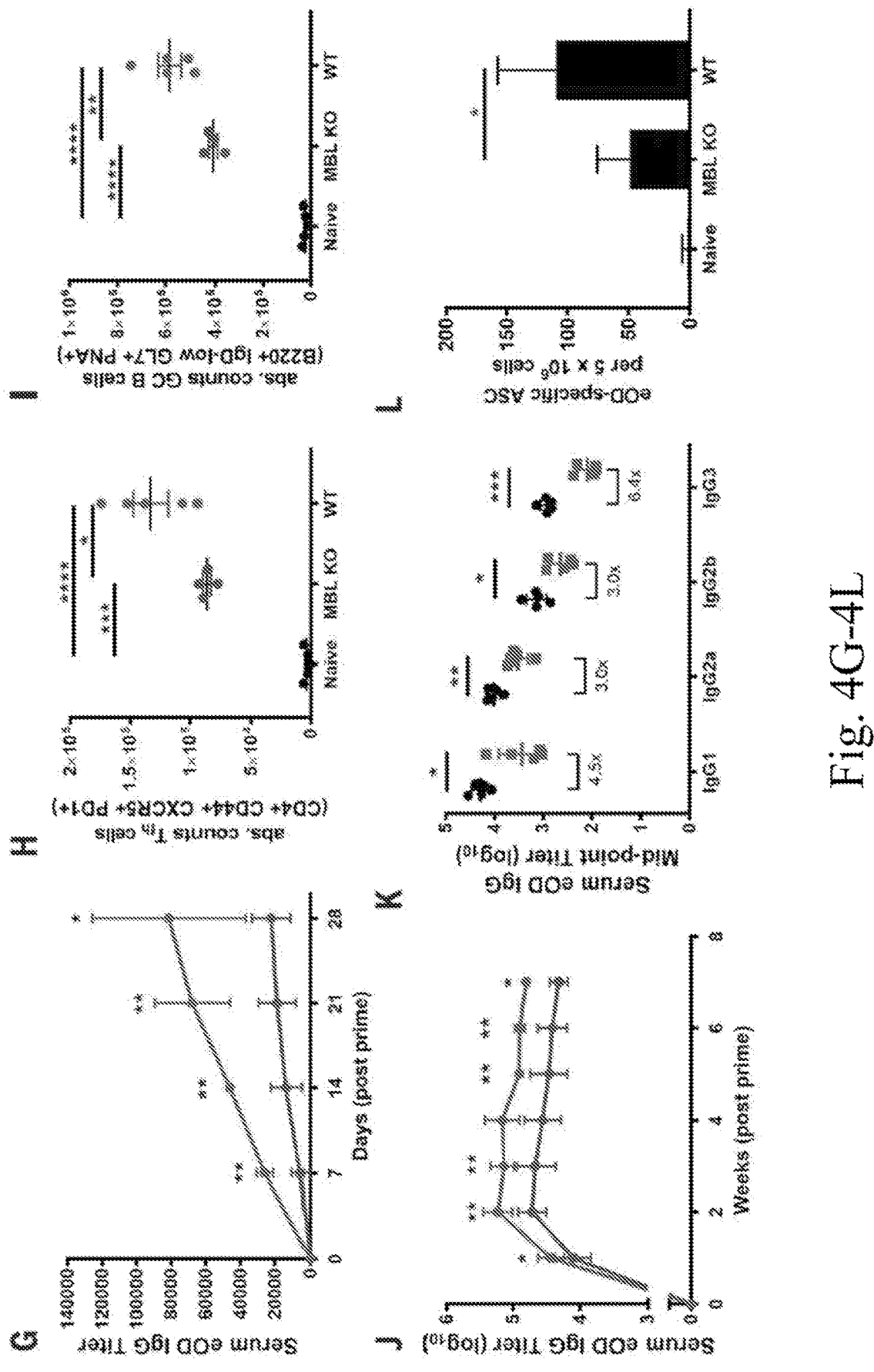

The immunological effects of MBL recognition and FDC targeting were assessed. WT mice immunized with nanoparticle eOD-60mer showed an IgG response two times that elicited by deglycosylated eOD-60mer (FIG. 4G). Further, responses to eOD-60mer were stronger in WT mice than in MBL KO mice by several measures, with 53% greater Miceli responses, 43% greater GC B cell responses, and IgG titers about five times as high across multiple antibody isotypes, irrespective of the adjuvant used (FIG. 4, H to K, and FIGS. 15, A and B). IgG binding to plates coated with a low versus high density of antigen was also proportionally weaker for sera from MBL KO animals than for sera from WT mice, suggesting a lower mean avidity of IgG elicited in MBL KO animals (FIG. 15C). Eight weeks postimmunization, WT mice also had approximately double the population of bone marrow-resident eOD-specific antibody-secreting cells compared with MBL KO animals (FIG. 4L). Notably, MBL binding to eOD did not obscure recognition of the CD4 binding site (FIG. 16), suggesting that innate recognition of Env glycans would not inhibit generation of on-target antibody responses. Thus, despite preserving high multivalency for B cell receptor triggering, nanoparticles lacking MBL-mediated FDC targeting elicit weaker humoral responses.

Figure 4M:
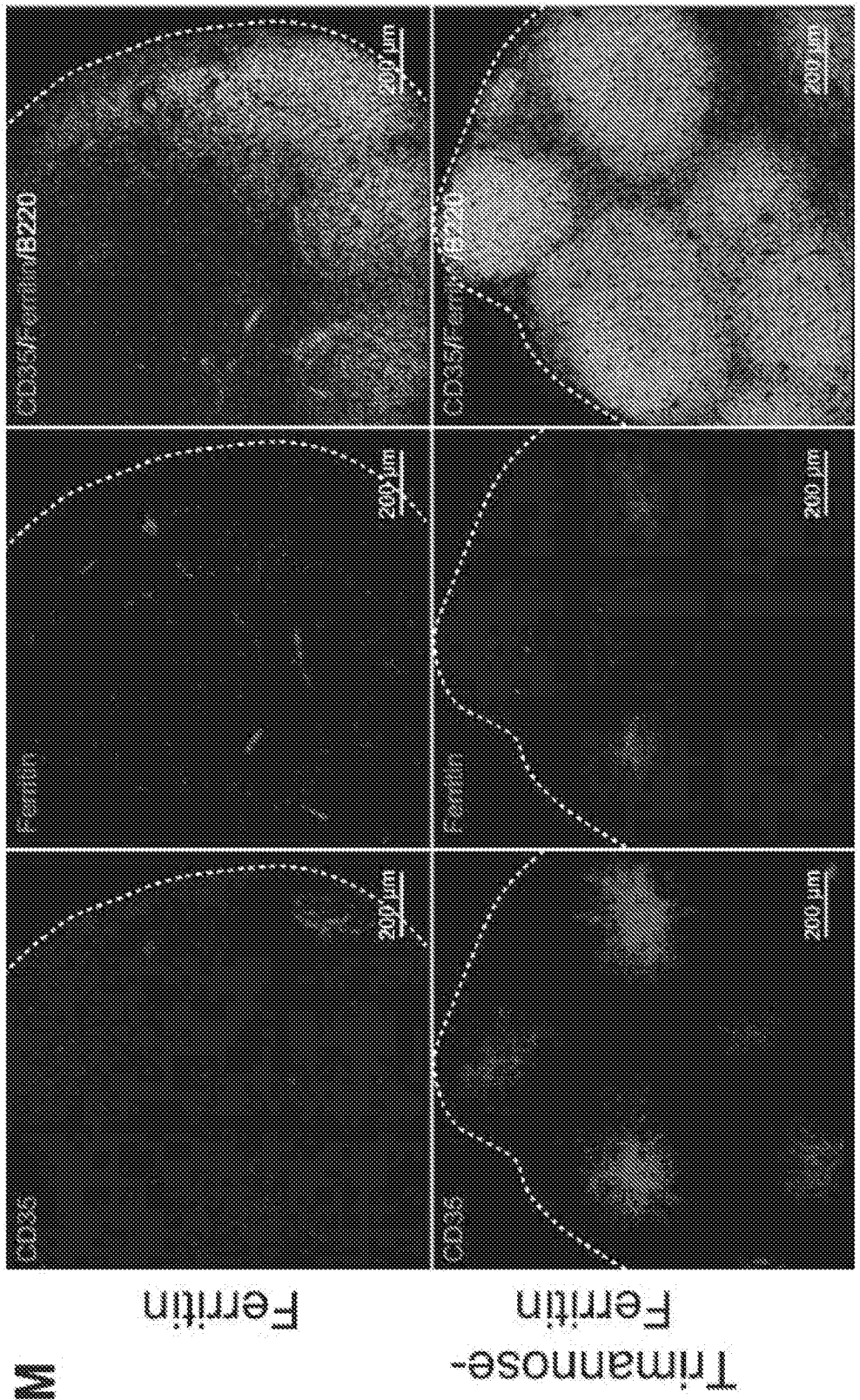

Lastly, whether synthetic introduction of glycans could be used to engineer the delivery of nanoparticles to follicles was examined, as a preliminary test of the utility of glycan engineering to alter the processing of nanoparticle vaccines in vivo. Bare ferritin nanoparticles lacking any glycosylation were expressed; these particles showed low overall accumulation in LNs and no colocalization with FDCs after the immunization of WT mice (FIG. 4M). By contrast, conjugation of a synthetic trimannose moiety to these nanoparticles led to pronounced accumulation on FDCs within 3 days of immunization (FIG. 4M and FIG. 17A); this FDC localization was glycan density dependent because ferritin nanoparticles functionalized with a lower density of trimannose groups (~25 versus ~96 trimannose groups per particle) did not localize to the FDC network (FIG. 17B). To determine whether glycan-mediated delivery to FDCs could be achieved with synthetic nanoparticles and to assess the effect of particle size, monodisperse polystyrene nanoparticles wree functionalized with the same trimannose groups at high density (FIG. 18A). Polystyrene nanoparticles 40 nm in diameter accumulated on FDCs (albeit with lower efficiency than the protein nanoparticles, possibly because of some level of aggregation in vivo), whereas 100- or 200-nm-diameter particles were excluded from follicles (FIG. 18B). Thus, synthetic introduction of even simple glycans through chemical or genetic approaches may provide a means to direct arbitrary vaccine nanoparticles of appropriate size to the FDC network.

Collectively, these data suggest that glycosylated nanoparticles trigger MBL-mediated innate immune recognition, leading to rapid complement-dependent transport to FDCs and subsequent concentration in GCs in vivo. This targeted trafficking was associated with enhanced antibody responses, suggesting that tuning immunogen glycosylation may be a key design criterion for future nanoparticulate vaccines or immunomodulators and providing an explanation for how FDC localization of immunogens can occur in the absence of preexisting antibody. These findings are especially interesting in the context of HIV vaccine development, where the dense envelope "glycan shield" is often viewed as a hurdle to achieving efficient antibody responses.

Example 3

The following table provides non-limiting examples of amino acid sequences that can be used in methods, compositions, preparations, and formulations according to the invention. SEQ ID NO:1 represents the MD39 nanoparticle exemplified above, comprising a GSG linker from a.a. 635-637 at the start of the ferritin sequence. The ferritin sequence of *Pyrococcus furiosus* is from PDB: 2JD6 (See also WP_011011871.1) but with the inclusion of a single R->K mutation at a.a. 701 to eliminate a potential cleavage site. SEQ ID NO:2 is an example of a variant of SEQ ID NO:1 which contains two additional glycans (NVS at aa. 211-213; NTS at aa. 259-261). SEQ ID NO:3 differs from SEQ ID NO:1 in that the furin cleavage site in MD39 is altered so as not to be cleavable by furin. SEQ ID NO:4 comprises a different ferritin (*Helicobacter pylori*; see WP_000949190.1) as compared to SEQ ID NO:1.

TABLE 2

| Sequences | |
|---|---|
| MD39-8mer<br>aka<br>BG505_SOSIP_MD39_<br>2JD6_m<br>SEQ ID NO: 1 | AENLWVTVYY GVPVWKDAET TLFCASDAKA YETEKHNVWA THACVPTDPN<br>PQEIHLENVT EEFNMWKNNM VEQMHEDIIS LWDQSLKPCV KLTPLCVTLQ<br>CTNVTNNITD DMRGELKNCS FNMTTELRDK KQKVYSLFYR LDVVQINENQ<br>GNRSNNSNKE YRLINCNTSA ITQACPKVSF EPIPIHYCAP AGFAILKCKD<br>KKFNGTGPCP SVSTVQCTHG IKPVVSTQLL LNGSLAEEEV IIRSENITNN<br>AKNILVQLNT PVQINCTRPN NNTVKSIRIG PGQAFYYTGD IIGDIRQAHC<br>NVSKATWNET LGKVVKQLRK HFGNNTIIRF AQSSGGDLEV TTHSFNCGGE<br>FFYCNTSGLF NSTWISNTSV QGSNSTGSND SITLPCRIKQ IINMWQRIGQ<br>AMYAPPIQGV IRCVSNITGL ILTRDGGSTN STTETFRPGG GDMRDNWRSE<br>LYKYKVVKIE PLGVAPTRCK RRVVGRRRRR RAVGIGAVSL GFLGAAGSTM<br>GAASMTLTVQ ARNLLSGIVQ QQSNLLRAPE PQQHLLKDTH WGIKQLQARV<br>LAVEHYLRDQ QLLGIWGCSG KLICCTNVPW NSSWSNRNLS EIWDNMTWLQ<br>WDKEISNYTQ IIYGLLEESQ NQQEKNEQDL LALDGSGGLS ERMLKALNDQ<br>LNRELYSAYL YFAMAAYFED LGLEGFANWM KAQAEEEIGH ALRFYNYIYD<br>KNGRVELDEI PKPPKEWESP LKAFEAAYEH EKFISKSIYE LAALAEEEKD<br>YSTRAFLEWF INEQVEEEAS VKKILDKLKF AKDSPQILFM LDKELSARAP<br>KLPGLLMQGG E** |
| BG505_MD39_G41_<br>2JD6_m<br>2 additional glycans<br>SEQ ID NO: 2 | AENLWVTVYY GVPVWKDAET TLFCASDAKA YETEKHNVWA THACVPTDPN<br>SSEIHLENVT EEFNMWKNNM VEQMHEDIIS LWDQSLKPCV KLTPLCVTLQ<br>CTNVTNNITD DMRGELKNCS FNMTTELRDK KQKVYSLFYR LDVVQINENQ<br>GNRSNNSNKE YRLINCNTSA ITQACPKVSF EPIPIHYCAP AGFAILKCKD<br>KKFNGTGPCQ NVSTVQCTHG IKPVVSTQLL LNGSLAEEEV IIRSENITNN<br>AKNILVQLNT SVQINCTRPN NNTVKSIRIG PGQAFYYTGD IIGDIRQAHC<br>NVSKATWNET LGKVVKQLRK HFGNNTIIRF AQSSGGDLEV TTHSFNCGGE<br>FFYCNTSGLF NSTWISNTSV QGSNSTGSND SITLPCRIKQ IINMWQRIGQ<br>AMYAPPIQGV IRCVSNITGL ILTRDGGSTN STTETFRPGG GDMRDNWRSE<br>LYKYKVVKIE PLGVAPTRCK RRVVGRRRRR RAVGIGAVSL GFLGAAGSTM<br>GAASMTLTVQ ARNLLSGIVQ QQSNLLRAPE PQQHLLKDTH WGIKQLQARV<br>LAVEHYLRDQ QLLGIWGCSG KLICCTNVPW NSSWSNRNLS EIWDNMTWLQ<br>WDKEISNYTQ IIYGLLEESQ NQQEKNEQDL LALDGSGGLS ERMLKALNDQ<br>LNRELYSAYL YFAMAAYFED LGLEGFANWM KAQAEEEIGH ALRFYNYIYD<br>KNGRVELDEI PKPPKEWESP LKAFEAAYEH EKFISKSIYE LAALAEEEKD<br>YSTRAFLEWF INEQVEEEAS VKKILDKLKF AKDSPQILFM LDKELSARAP<br>KLPGLLMQGG E** |
| BG505_MD39_link14_<br>2JD6_m<br>SEQ ID NO: 3 | AENLWVTVYY GVPVWKDAET TLFCASDAKA YETEKHNVWA THACVPTDPN<br>PQEIHLENVT EEFNMWKNNM VEQMHEDIIS LWDQSLKPCV KLTPLCVTLQ<br>CTNVTNNITD DMRGELKNCS FNMTTELRDK KQKVYSLFYR LDVVQINENQ<br>GNRSNNSNKE YRLINCNTSA ITQACPKVSF EPIPIHYCAP AGFAILKCKD<br>KKFNGTGPCP SVSTVQCTHG IKPVVSTQLL LNGSLAEEEV IIRSENITNN<br>AKNILVQLNT PVQINCTRPN NNTVKSIRIG PGQAFYYTGD IIGDIRQAHC<br>NVSKATWNET LGKVVKQLRK HFGNNTIIRF AQSSGGDLEV TTHSFNCGGE<br>FFYCNTSGLF NSTWISNTSV QGSNSTGSND SITLPCRIKQ IINMWQRIGQ<br>AMYAPPIQGV IRCVSNITGL ILTRDGGSTN STTETFRPGG GDMRDNWRSE<br>LYKYKVVKIE PLGVAPTRCK RRVVGSHSGS GGSGSGGHAA VGIGAVSLGF<br>LGAAGSTMGA ASMTLTVQAR NLLSGIVQQQ SNLLRAPEPQ QHLLKDTHWG<br>IKQLQARVLA VEHYLRDQQL LGIWGCSGKL ICCTNVPWNS SWSNRNLSEI<br>WDNMTWLQWD KEISNYTQII YGLLEESQNQ QEKNEQDLLA LDGSGGLSER<br>MLKALNDQLN RELYSAYLYF AMAAYFEDLG LEGFANWMKA QAEEEIGHAL<br>RFYNYIYDKN GRVELDEIPK PPKEWESPLK AFEAAYEHEK FISKSIYELA<br>ALAEEEKDYS TRAFLEWFIN EQVEEEASVK KILDKLKFAK DSPQILFMLD<br>KELSARAPKL PGLLMQGGE* * |
| BG505_MD39_3bve_m<br>different ferritin<br>SEQ ID NO: 4 | AENLWVTVYY GVPVWKDAET TLFCASDAKA YETEKHNVWA THACVPTDPN<br>PQEIHLENVT EEFNMWKNNM VEQMHEDIIS LWDQSLKPCV KLTPLCVTLQ<br>CTNVTNNITD DMRGELKNCS FNMTTELRDK KQKVYSLFYR LDVVQINENQ<br>GNRSNNSNKE YRLINCNTSA ITQACPKVSF EPIPIHYCAP AGFAILKCKD<br>KKFNGTGPCP SVSTVQCTHG IKPVVSTQLL LNGSLAEEEV IIRSENITNN<br>AKNILVQLNT PVQINCTRPN NNTVKSIRIG PGQAFYYTGD IIGDIRQAHC<br>NVSKATWNET LGKVVKQLRK HFGNNTIIRF AQSSGGDLEV TTHSFNCGGE<br>FFYCNTSGLF NSTWISNTSV QGSNSTGSND SITLPCRIKQ IINMWQRIGQ<br>AMYAPPIQGV IRCVSNITGL ILTRDGGSTN STTETFRPGG GDMRDNWRSE<br>LYKYKVVKIE PLGVAPTRCK RRVVGRRRRR RAVGIGAVSL GFLGAAGSTM<br>GAASMTLTVQ ARNLLSGIVQ QQSNLLRAPE PQQHLLKDTH WGIKQLQARV<br>LAVEHYLRDQ QLLGIWGCSG KLICCTNVPW NSSWSNRNLS EIWDNMTWLQ |

TABLE 2-continued

Sequences

|  |  |
|---|---|
|  | WDKEISNYTQ IIYGLLEESQ NQQEKNEQDL LALDGSGGLS KDIIKLLNEQ<br>VNKEMQSSNL YMSMSSWCYT HSLDGAGLFL FDHAAEEYEH AKKLIIFLNE<br>NNVPVQLTSI SAPEHKFEGL TQIFQKAYEH EQHISESINN IVDHAIKSKD<br>HATFNFLQWY VAEQHEEEVL FKDILDKIEL IGNENHGLYL ADQYVKGIAK<br>SRKS** |
| WP_011011871<br>ferritin [*Pyrococcus*<br>*furiosus*]<br>SEQ ID NO: 5 | MLSERMLKAL NDQLNRELYS AYLYFAMAAY FEDLGLEGFA NWMKAQAEEE<br>IGHALRFYNY IYDRNGRVEL DEIPKPPKEW ESPLKAFEAA YEHEKFISKS<br>IYELAALAEE EKDYSTRAFL EWFINEQVEE EASVKKILDK LKFAKDSPQI<br>LFMLDKELSA RAPKLPGLLM QGGE |
| WP_011011871<br>ferritin [*Pyrococcus*<br>*furiosus*]<br>SEQ ID NO: 6 | MLSKDIIKLL NEQVNKEMNS SNLYMSMSSW CYTHSLDGAG LFLFDHAAEE<br>YEHAKKLIIF LNENNVPVQL TSISAPEHKF EGLTQIFQKA YEHEQHISES<br>INNIVDHAIK SKDHATFNFL QWYVAEQHEE EVLFKDILDK IELIGNENHG<br>LYLADQYVKG IAKSRKS |
| P02794 (UNIPROT-KB)<br>Human ferritin<br>heavy chain<br>SEQ ID NO: 7 | MTTASTSQVR QNYHQDSEAA INRQINLELY ASYVYLSMSY YFDRDDVALK<br>NFAKYFLHQS HEEREHAEKL MKLQNQRGGR IFLQDIKKPD CDDWESGLNA<br>MECALHLEKN VNQSLLELHK LATDKNDPHL CDFIETHYLN EQVKAIKELG<br>DHVTNLRKMG APESGLAEYL FDKHTLGDSD NES |

1. M. F. Bachmann, G. T. Jennings, Vaccine delivery: A matter of size, geometry, kinetics and molecular patterns. *Nat. Rev. Immunol.* 10, 787-796 (2010). doi: I 0.1038/nri2868 Medline 2. P. S. Naud, C. M. Roteli-Martins, N. S. De Carvalho, J. C. Teixeira, P. C. de Borba, N. Sanchez, T. Zahaf, G. Catteau, B. Geeraerts, D. Descamps, Sustained efficacy, immunogenicity, and safety of the HPV-16/18 AS04-adjuvanted vaccine. *Hum. Vaccin. Immunother.* 10, 2147-2162 (2014). doi:10.4161/Iw.29532 Medline 3. Y. Jackson, F. Chappuis, N. Mezger, K. Kanappa, L. Loutan, High immunogenicity of delayed third dose of hepatitis B vaccine in travellers. Vaccine 25, 3482-3484 (2007). doi:10.1016/j.vaccine.2006.12.053 Medline 4. M. Kanekiyo, C.-J. Wei, H. M. Yassine, P. M. McTamney, J. C. Boyington, J. R. R. Whittle, S. S. Rao, W.-P. Kong, L. Wang, G. J. Nabel, Self-assembling influenza nanoparticle vaccines elicit broadly neutralizing H1N1 antibodies. Nature 499, 102-106 (2013). doi: 10.1038/nature12202 Medline 5. M. Kanekiyo, W. Bu, M. G. Joyce, G. Meng, J. R. R. Whittle, U. Baxa, T. Yamamoto, S. Narpala, J.-P. Todd, S. S. Rao, A. B. McDermott, R. A. Koup, M. G. Rossmann, J. R. Mascola, B. S. Graham, J. I. Cohen, G. J. Nabel, Rational design of an Epstein-Barr virus vaccine targeting the receptor-binding site. Cell 162, 1090-1100 (2015). doi:10.1016j.cell.2015.07.043 Mediine 6. J. Jardine, J.-P. Julien, S. Menis, T. Ota, O. Kalyuzhniy, A. McGuire, D. Sok, P.-S. Huang, S. MacPherson, M. Jones, T. Nieusma, J. Mathison, D. Baker, A. B. Ward, D. R. Burton, L. Stamatatos, D. Nemazee, I. A. Wilson, W. R. Schief, Rational HIV immunogen design to target specific germline B cell receptors. *Science* 340, 711-716 (2013). doi:10.1126/science.1234150 Medline 7. R. K. Abbott, J. H. Lee, S. Menis, P. Skog, M. Rossi, T. Ota, D. W. Kulp, D. Bhullar, O. Kalyuzhniy, C. Havenar-Daughton, W. R. Schief, D. Nemazee, S. Crotty, Precursor frequency and affinity determine B cell competitive fitness in germinal centers, tested with germline-targeting HIV vaccine immunogens. *Immunity* 48, 133-146.e6 (2018). doi. 10.1016/j.immuni.2017.11.023 Medline 8. J. M. Steichen, D. W. Kulp, T. Tokatlian, A. Escolano, P. Dosenovic, R. L. Stanfield, L. E. McCoy, G. Ozorowski, X. Hu, O. Kalyuzhniy, B. Briney, T. Schiffner, F. Garces, N. T. Freund, A. D. Gitlin, S. Menis, E. Georgeson, M. Kubitz, Y. Adachi, M. Jones, A. A. Mutafyan, D. S. Yun, C. T. Mayer, A. B. Ward, D. R. Burton, I. A. Wilson, D. J. Irvine, M. C. Nussenzweig, W. R. Schief, HIV vaccine design to target germline precursors of glycan-dependent broadly neutralizing antibodies. *Immunity* 45, 483-496 (2016). doi: 10.1016j.immuni.2016.08.016 Medline 9. J. Ingale, A. Stano, J. Guenaga, S. K. Sharma, D. Nemazee, M. B. Zwick, R. T. Wyatt, High density array of well-ordered HIV-1 spikes on synthetic liposomal nanoparticles efficiently activate B cells. *Cell Rep.* 15, 1986-1999 (2016). doi:10.1016j.celrep.2016.04.078 Medline 10. S. Bale, G. Goebrecht, A. Stano, R. Wilson, T. Ota, K. Tran, J. Ingale, M. B. Zwick, R. T. Wyatt, Covalent linkage of HIV-1 trimers to synthetic liposomes elicits improved B cell and antibody responses. *J. Viral.* 91, e00443-17 (2017). doi:10.1128./JVI.00443-17 Medline 11. T. Tokatlian, D. W. Kulp, A. A. Mutafyan, C. A. Jones, S. Menis, E. Georgeson, M. Kubitz, M. H. Zhang, M. B. Melo, M. Silva, D. S. Yun, W. R. Schief, D. J. Irvine, Enhancing humoral responses against HIV envelope trimers via nanoparticle delivery with stabilized synthetic liposomes. *Sci. Rep.* 8, 16527 (2018). doi: 10.1038/s41598-018-34853-2 Medline 12. P. Martinez-Murillo, K. Tran, J. Guenaga, G. Lindgren, M. Àdori, Y. Feng, G. E. Phad, N. Vázquez Bernat, S. Bale, J. Ingale, V. Dubrovskaya, S. O'Dell, L. Pramanik, M. Spångberg, M. Corcoran, K. Loré, J. R. Mascola, R. T. Wyatt, G. B. Karlsson Hedestam, Particulate array of well-ordered HIV clade C Env trimers elicits neutralizing antibodies that display a unique V2 cap approach. *Immunity* 46, 804-817.e7 (2017). doi: 10.1016/j.immuni.2017.04.021 Medline 13. K. Sliepen, G. Ozorowski, J. A. Burger, T. van Montfort, M. Stunnenberg, C. LaBranche, D. C. Montefiori, J. P. Moore, A. B. Ward, R. W. Sanders, Presenting native-like HIV-1 envelope trimers on ferritin nanoparticles improves their immunogenicity. *Retrovirology* 12, 82 (2015). doi:10.1186/s12977-015-02104 Medline 14. J. G. Jardine, T. Ota, D. Sok, M. Pauthner, D. W. Kulp, O. Kalyuzhniy, P. D. Skog, T. C. Thinnes, D. Bhullar, B. Briney, S. Menis, M. Jones, M. Kubitz, S. Spencer, Y. Adachi, D. R. Burton, W. R. Schief, D. Nemazee, Priming a broadly neutralizing antibody response to HIV-1 using a germline-targeting immunogen. *Science* 349, 156-161 (2015). doi:10.1126/science.aac5894 Medline 15. J. G. Jardine, D. W. Kulp, C. Havenar-Daughton, A. Sarkar, B. Briney, D. Sok, F. Sesterhenn, J. Ereño-Orbea, O. Kalyuzhniy, I. Deresa, X. Hu, S. Spencer, M. Jones, E. Georgeson, Y. Adachi, M. Kubitz, A. C. deCamp, J.-P. Julien, I. A. Wilson, D. R. Burton, S. Crotty, W. R. Schief, HIV-1 broadly neutralizing antibody precursor B cells revealed by germline-targeting immunogen. *Science* 351, 1458-1463 (2016). doi: 10.1126/science.aad9195 Medline 16. D. Sok, B. Briney, J. G. Jardine, D. W. Kulp, S. Menis, M. Pauthner, A. Wood, E.-C. Lee, K. M. Le, M. Jones, A. Ramos, O. Kalyuzhniy, Y. Adachi, M. Kubitz, S. MacPherson, A. Bradley, G. A. Friedrich, W. R. Schief, D. R. Burton, Priming HIV-1 broadly neutralizing antibody precursors in human Ig loci transgenic mice. *Science* 353, 1557-1560 (2016). doi: 10. 1126/science.aah3945 Medline 17. D. W. Kulp, J. M. Steichen, M. Pauthner, X. Hu, T. Schiffner, A. Liguori, C. A. Cottrell, C. Havenar-Daughton, G. Ozorowski, E. Georgeson, O. Kalyuzhniy, J. R. Willis, M. Kubitz, Y. Adachi, S. M. Reiss, M. Shin, N. de Val, A. B. Ward, S. Crotty, D. R. Burton, W. R. Schief, Structure-based design of native-like HIV-1 envelope trimers to silence nonneutralizing epitopes and eliminate CD4 binding. *Nat. Commun.* 8, 1655 (2017). doi: 10.1038/s41467-017-01549-6 Medline 18. L. He, N. de Val, C. D. Morris, N. Vora, T. C. Thinnes, L. Kong, P. Azadnia, D. Sok, B. Zhou, D. R. Burton, I. A. Wilson, D. Nemazee, A. B. Ward, J. Zhu, Presenting native-like trimeric HIV-1 antigens with self-assembling nanoparticles. *Nat. Commun.* 7, 12041 (2016). doi 10.1038/ncomms12041 Medline 19. C. Park, J. Arthos, C. Cicala, J. H. Kehrl, The HIV-1 envelope protein gp120 is captured and displayed for B cell recognition by SIGN-R1+lymph node macrophages. *eLife* 4, e06467 (2015). doi:10.7554/eLife.06467 Medline 20. V. Manolova, A. Flace, M. Bauer, K. Schwarz, P. Saudan, M. F. Bachmann, Nanoparticles target distinct dendritic cell populations according to their size. *Eur. J. Immunol.* 38, 1404-1413 (2008). doi:10.1002/eji 0.200737984 Medline 21. J. J. Moon, H. Suh, A. V. Li, C. F. Ockenhouse, A. Yadava, D. J. Irvine, Enhancing humoral responses to a malaria antigen with nanoparticle vaccines that expand Tfh cells and promote germinal center induction. *Proc. Natl. Acad. Sci. U.S.A.* 109, 1080-1085 (2012). doi:10.1073/pnas.1112648109 Medline 22. S. T. Reddy, A. Rehor, H. G. Schmoekel, J. A. Hubbell, M. A. Swartz, In vivo targeting of dendritic cells in lymph nodes with poly(propylene sulfide) nanoparticles. *J. Controlled Release* 112, 26-34 (2006). doi:10.1016/j jconrel.2006.01.006 Medline 23. S. Shukla, J. T. Myers, S. E. Woods, X. Gong, A. E. Czapar, U. Commandeur, A. Y. Huang, A. D. Levine, N. F. Steinmetz, Plant viral nanoparticles-based HER2 vaccine: Immune response influenced by differential transport, localization and cellular interactions of particulate carriers. Biomaterials 121, 15-27 (2017). doi: 10.1016/j.biomaterials.2016.12.030 Medline 24. T. G. Phan, I. Grigorova, T. Okada, J. G. Cyster, Subcapsular encounter and complement dependent transport of immune complexes by lymph node B cells. *Nat. Immunol.* 8, 992-1000 (2007). doi:10.1038/ni1494 Medline 25. T. G. Phan, J. A. Green, E. E. Gray, Y. Xu, J. G. Cyster, Immune complex relay by subcapsular sinus macrophages and noncognate B cells drives antibody affinity maturation. *Nat. Immunol.* 10, 786-793 (2009). doi: 10.1038/ni.1745 Medline 26. Y. R. Carrasco, F. D. Batista, B cells acquire particulate antigen in a macrophage-rich area at the boundary between the follicle and the subcapsular sinus of the lymph node. *Immunity* 27, 160-171 (2007). doi: 10.1016/j.immuni.2007.06.007 Mediine 27. P. Garred, N. Genster, K. Pilely, R. Bayarri-Olmos, A. Rosbj erg, Y. J. Ma, M.-O. Skjoedt, A journey through the lectin pathway of complement-MBL and beyond. *Immunol. Rev.* 274, 74-97 (2016). doi:10.1111/imr.12468 Medline 28. W. K. Eddie Ip, K. Takahashi, R. A. Ezekowitz, L. M. Stuart, Mannose-binding lectin and innate immunity. *Immunol. Rev.* 230, 9-21 (2009). doi:10.1111/j.1600-065X.2009.00789.x Medline 29. M. Howard, C. A. Farrar, S. H. Sacks, Structural and functional diversity of collectins and ficolins and their relationship to disease. *Semin. Immunopathol.* 40, 75-85 (2018). doi:10.1007/s00281-017-0642-0 Medline 30. S. Sheriff, C. Y. Chang, R. A. Ezekowitz, Human mannose-binding protein carbohydrate recognition domain trimerizes through a triple alpha-helical coiled-coil. *Nat. Struct. Biol.* 1, 789-794 (1994). doi:10.1038/nsb1194-789 Medline 31. M. W. Turner, Mannose-binding lectin: The pluripotent molecule of the innate immune system. *Immunol. Today* 17, 532-540 (1996). doi:10.1016/S0167-5699 (96)80908-X Medline 32. X. Wu, Z.-Y. Yang, Y. Li, C.-M. Hogerkorp, W. R. Schief, M. S. Seaman, T. Zhou, S. D. Schmidt, L. Wu, L. Xu, N. S. Longo, K. McKee, S. O'Dell, M. K. Louder, D. L. Wycuff, Y. Feng, M. Nason, N. Doria-Rose, M. Connors, P. D. Kwong, M. Roederer, R. T. Wyatt, G. J. Nabel, J. R. Mascola, Rational design of envelope identifies broadly neutralizing human monoclonal antibodies to HIV-1. *Science* 329, 856-861 (2010). doi:10.1126/science.1187659 Medline 33. D. H. Barouch, Z. Y. Yang, W. P. Kong, B. Korioth-Schmitz, S. M. Sumida, D. M. Truitt, M. G. Kishko, J. C. Arthur, A. Miura, J. R. Mascola, N. L. Letvin, G. J. Nabel, A human T cell leukemia virus type 1 regulatory element enhances the immunogenicity of human immunodeficiency virus type 1 DNA vaccines in mice and nonhuman primates. *J. Virol.* 79, 8828-8834 (2005). doi:10.1128/JVI.79.14.8828-8834.2005 Medline 34. K. Lövgren-Bengtsson, B. Morein, in *Methods in Molecular Medicine*, vol. 42*, Vaccine Adjuvants: Preparation Methods and Research Protocols*, D. T. O'Hagan, Ed. (Humana Press, 2000), pp. 239-258.

35. D. Suan, A. Nguyen, I. Moran, K. Bourne, J. R. Hermes, M. Arshi, H. R. Hampton, M. Tomura, Y. Miwa, A. D. Kelleher, W. Kaplan, E. K. Deenick, S. G. Tangye, R. Brink, T. Chtanova, T. G. Phan, T follicular helper cells have distinct modes of migration and molecular signatures in naive and memory immune responses. *Immunity* 42, 704-718 (2015). doi.10.1016/j.immuni.2015.03.002 Medline 36. C. Havenar-Daughton, S. M. Reiss, D. G. Carnathan, J. E. Wu, K. Kendric, A. Torrents de la Peña, S. P. Kasturi, J. M. Dan, M. Bothwell, R. W. Sanders, B. Pulendran, G. Silvestri, S. Crotty, Cytokine-independent detection of antigen-specific germinal center T follicular helper cells in immunized nonhuman primates using a live cell activation-induced marker technique. *J. Immunol.* 197, 994-1002 (2016). doi:10.4049/jimmunol.1600320 Medline 37. J. M. Dan, C. S. Lindestam Arlehamn, D. Weiskopf, R. da Silva Antunes, C. Havenar-Daughton, S. M. Reiss, M. Brigger, M. Bothwell, A. Sette, S. Crotty, A cytokineindependent approach to identify antigen-specific human germinal center T follicular helper cells and rare antigen-specific CD4$^+$ T cells in blood. *J. Immunol.* 197, 983-993 (2016). doi:10.4049/jimmunol.1600318 Medline 38. T. Zhou, J. Zhu, Y. Yang, J. Gorman, G. Ofek, S. Srivatsan, A. Druz, C. Lees, G. Lu, C. Soto, J. Stuckey, D. Burton, W. Koff, M. Connors, P. Kwon, Transplanting supersites of HIV-1 vulnerability. PLoS One, 9 (2014), p. e99881. https://doi.org/10.1371/journal.pone.0099881

39. T. Granier, B. Langlois d'Estaintot, B. Gallois, J. M. Chevalier, G. Precigoux, P. Santambrogio, et al., Structural description of the active sites of mouse L-chain ferritin at 1.2 A resolution. J Biol Inorg Chem, 8 (2003), pp. 105-111

(40) D. M. Lawson, P. J. Artymiuk, S. J. Yewdall, J. M. Smith, J. C. Livingstone, A. Treffry, et al., Solving the structure of human H ferritin by genetically engineering intermolecular crystal contacts. Nature, 349 (1991), pp. 541-544

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A synthetic peptide which comprises a glycosylated Env peptide of HIV and a support peptide, wherein the synthetic peptide forms a self-assembling nanoparticle, wherein the nanoparticle is transported to the follicular dendritic cell (FDC) network and by complement-dependent, mannose-binding-lectin (MBL)-dependent, and/or immunogen-glycan-dependent transport to germinal centers, wherein the synthetic peptide has the sequence of BG505_MD39_G41_2JD6 (SEQ ID NO:2), BG505_MD39_link14_2JD6 (SEQ ID NO: 3), or BG505_MD39_3bve_m (SEQ ID NO:4), wherein the Env peptide is glycosylated with oligomannose, and wherein the support peptide is a ferritin based support peptide.

2. The synthetic peptide of claim 1, wherein the support peptide comprises at least 25 contiguous residues having a sequence that is identical to a sequence of at least 25 contiguous amino acids in Pyrococcus furiosus ferritin (SEQ ID NO:5).

3. A nanoparticle which comprises a plurality of the synthetic peptides of claim 1.

4. A nucleic acid encoding the synthetic peptide of claim 1.

5. A vector comprising a regulatory element operable in a eukaryotic cell operably linked to the nucleic acid of claim 4.

6. The vector of claim 5, wherein the vector comprises a viral vector.

7. The vector of claim 6, wherein the vector comprises Adeno-associated virus (AAV).

8. A method of eliciting an immune response in a mammal comprising administering the nanoparticle of claim 3.

9. The method of claim 8, wherein the mammal is a human.

10. The method of claim 8, wherein the mammal is a non-human primate.

11. The method of claim 8, wherein the mammal is a mouse.

12. The method of claim 8, wherein the mammal comprises elements of a human immune system.

13. The method of claim 8, wherein the method comprises administering two or more of the nanoparticles.

14. The method of claim 13, wherein the two or more nanoparticles are administered sequentially.

15. The method of claim 13, wherein the two or more nanoparticles are administered together.

16. The method of claim 8, wherein the nanoparticle is administered with an adjuvant.

17. The method of claim 16, wherein the adjuvant comprises a lecithin.

18. The method of claim 17, wherein the lecithin is (a) combined with an acrylic polymer, (b) in a coated oil droplet in an oil-in-water emulsion or (c) in an acrylic polymer in an oil-in-water emulsion.

19. The method of claim 16, wherein the adjuvant comprises alum.

20. The method of claim 8, wherein the nanoparticle is fixed.

21. The method of claim 20, wherein the nanoparticle is fixed in glutaraldehyde.

22. The method of claim 8, wherein the nanoparticle is quenched with glycine.

* * * * *